(12) United States Patent
Montarou et al.

(10) Patent No.: US 7,224,457 B2
(45) Date of Patent: *May 29, 2007

(54) PERFORMING RETARDATION MEASUREMENTS

(75) Inventors: Carole C. Montarou, Marietta, GA (US); Thomas K. Gaylord, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 181 days.

This patent is subject to a terminal disclaimer.

(21) Appl. No.: 10/949,855

(22) Filed: Sep. 24, 2004

(65) Prior Publication Data

US 2005/0068530 A1    Mar. 31, 2005

Related U.S. Application Data

(60) Provisional application No. 60/506,381, filed on Sep. 27, 2003, provisional application No. 60/506,014, filed on Sep. 25, 2003, provisional application No. 60/506,037, filed on Sep. 25, 2003.

(51) Int. Cl.
    *G01J 4/00*    (2006.01)
(52) U.S. Cl. ..................................... 356/364
(58) Field of Classification Search ............ None
    See application file for complete search history.

(56) References Cited

U.S. PATENT DOCUMENTS

| | | |
|---|---|---|
| 4,749,854 A | 6/1988 | Martens |
| 4,801,798 A | 1/1989 | Lange |
| 4,973,163 A | 11/1990 | Sakai et al. |
| 5,257,092 A | 10/1993 | Noguchi et al. |
| 5,406,371 A | 4/1995 | Sakai et al. |
| 5,450,200 A | 9/1995 | Imagawa |
| 5,504,581 A | 4/1996 | Nagata et al. |
| 5,825,492 A | 10/1998 | Mason |
| 5,864,403 A | 1/1999 | Ajji et al. |
| 5,917,598 A | 6/1999 | Mason |
| 6,034,774 A | 3/2000 | Marcus et al. |
| 6,219,139 B1 * | 4/2001 | Lesniak ............... 356/366 |
| 6,268,914 B1 | 7/2001 | Wang |
| 6,473,179 B1 | 10/2002 | Wang et al. |
| 6,473,181 B1 | 10/2002 | Oakberg |
| 6,697,157 B2 | 2/2004 | Wang et al. |
| 6,704,106 B2 * | 3/2004 | Anderson et al. ........ 356/367 |
| 6,738,137 B2 | 5/2004 | Oakberg |

* cited by examiner

*Primary Examiner*—Tu T. Nguyen
(74) *Attorney, Agent, or Firm*—Thomas, Kayden, Horstemeyer & Risley LLP

(57) ABSTRACT

Some embodiments include a system having a polarizer and an analyzer to define a light transmission axis. Both the polarizer and the analyzer have a polarization transmission direction, which is substantially perpendicular to the light transmission axis. A first waveplate and a second waveplate are is interposed between the polarizer and the analyzer, such that both waveplates are located along the light transmission axis. Both waveplates have a slow axis, which is substantially perpendicular to the light transmission axis. The first waveplate is rotated about the light transmission axis, such that the slow axis of the first waveplate is at an angle with a polarization transmission direction of the polarizer. The analyzer is rotated about the light transmission axis until the light transmitted through the system is minimized. The first waveplate and the analyzer are recursively rotated until an extinction angle is determined.

13 Claims, 40 Drawing Sheets

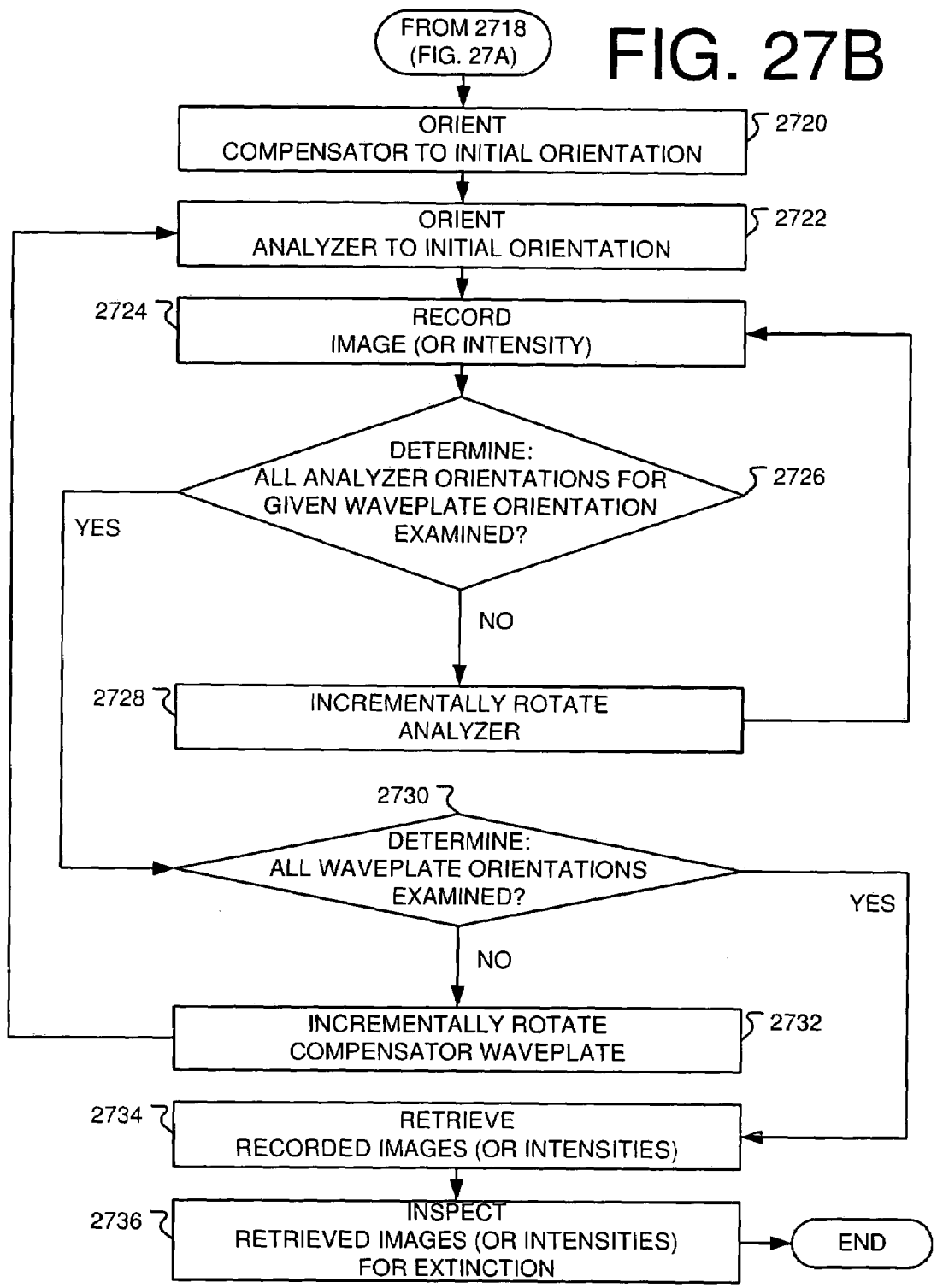

PERFORMING RETARDATION MEASUREMENTS

CROSS REFERENCE TO RELATED APPLICATIONS

This application claims the benefit of U.S. provisional patent application Ser. No. 60/506,037, having the title "High-Accuracy Single-Point and Full-Field Phase-Stepping Two-Waveplate Compensator for Optical Retardation, Magnitude, Retardation Orientation, Thickness, and Refractive Index Measure," filed on Sep. 25, 2003, which is incorporated herein by reference in its entirety.

This application also claims the benefit of U.S. provisional patent application Ser. No. 60/506,014, having the title "Full-Field Automated Two-Waveplate Compensator for Optical Retardation Magnitude, Retardation Orientation, Thickness, and Refractive Index Measurement," filed on Sep. 25, 2003, which is incorporated herein by reference in its entirety.

This application also claims the benefit of U.S. provisional patent application Ser. No. 60/506,381, having the title "Single-Point Two-Waveplate Compensator for Optical Retardation, Thickness, and Refractive Index Measurement," filed on Sep. 27, 2003, which is incorporated herein by reference in its entirety.

This application also incorporates by reference, in its entirety, United States patent application Ser. No. 10/950,048, having the title "Performing Retardation Measurements," filed on Sep. 24, 2004.

This application also incorporates by reference, in its entirety, United States patent application Ser. No. 10/949,602, having the title "Performing Retardation Measurements," filed on Sep. 24, 2004.

FIELD OF THE DISCLOSURE

The present disclosure relates generally to optics and, more particularly, to optical measurements.

BACKGROUND

For various reasons, birefringent properties of materials is of great interest in the scientific and engineering community. One conventional method for measuring birefringence is the Brace-Kohler compensator method, which is widely used in the industry to measure low levels of birefringence. Unfortunately, due to the system model for Brace-Kohler compensators, that method introduces measurement errors that are inherent to the presumptions underlying the model.

For at least this reason, a need exists in the industry for measuring birefringence with greater accuracy.

SUMMARY

The present disclosure provides systems and methods for measuring retardation in various materials.

Some embodiments include a system having a polarizer and an analyzer. The polarizer and the analyzer define a light transmission axis. The polarizer has a polarization transmission direction, which is substantially perpendicular to the light transmission axis. Similarly, the analyzer has a polarization transmission direction, which is also substantially perpendicular to the light transmission axis. A first waveplate is interposed between the polarizer and the analyzer, such that the first waveplate is located along the light transmission axis. The first waveplate has a slow axis, which is substantially perpendicular to the light transmission axis. A second waveplate is also interposed between the polarizer and the analyzer, such that the second waveplate is located along the light transmission axis. The second waveplate also has a slow axis, which is substantially perpendicular to the light transmission axis. The second waveplate is rotated about the light transmission axis, such that the slow axis of the second waveplate is at an angle with the transmission polarization transmission direction of the polarizer. The analyzer is rotated about the light transmission axis until the light transmitted through the system is minimized. The second waveplate and the analyzer are recursively rotated until light extinction is obtained.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 27A through 27B are flowcharts illustrating another embodiment of a method for measuring birefringence.

DETAILED DESCRIPTION OF THE EMBODIMENTS

Figure 1:
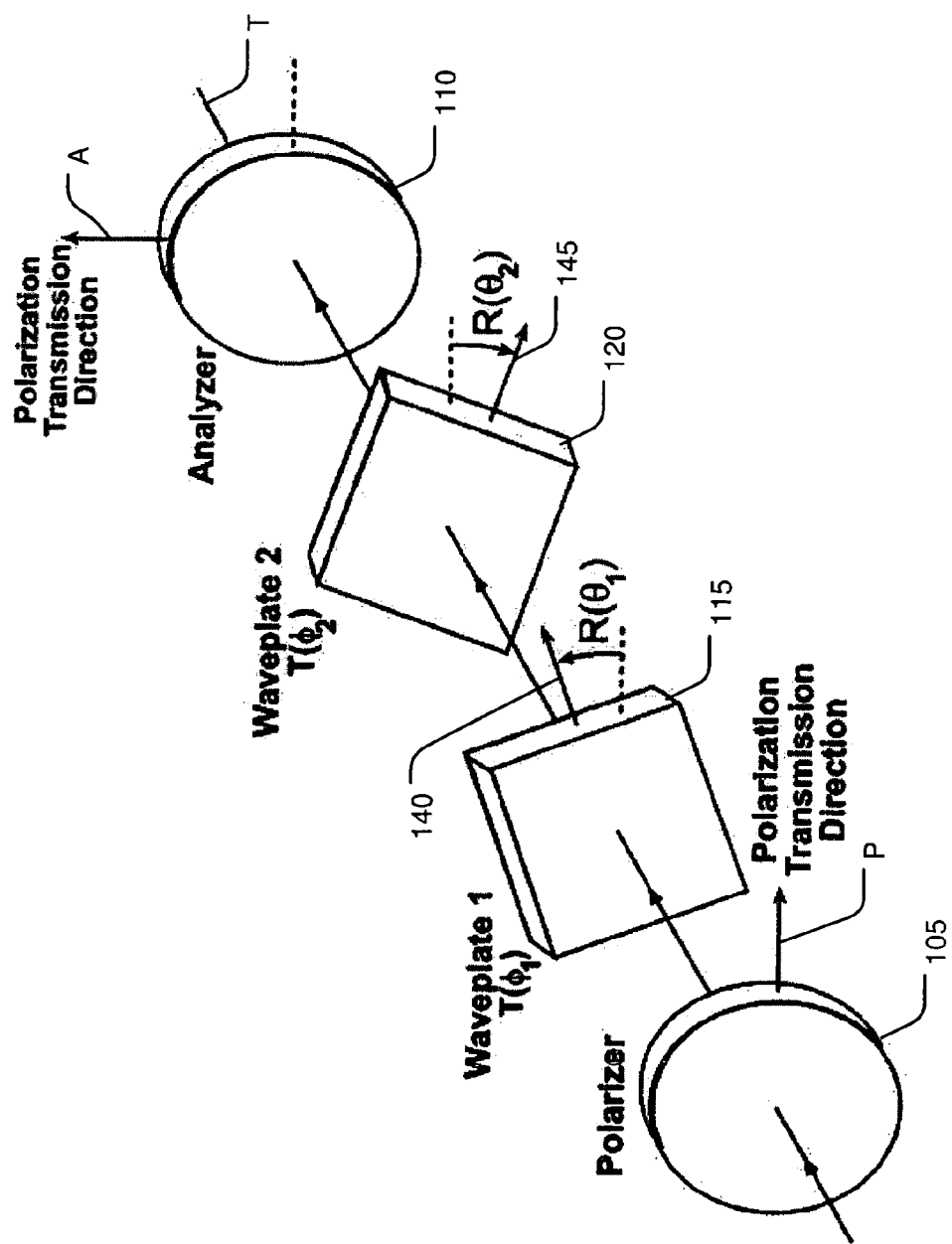
FIG. 1 is a schematic showing one embodiment, among others, of components in a system for measuring retardation.

Reference is now made in detail to the description of the embodiments as illustrated in the drawings. While several embodiments are described in connection with these drawings, there is no intent to limit the various inventions to the embodiment or embodiments disclosed herein. On the contrary, the intent is to cover all alternatives, modifications, and equivalents.

The transmitted polarization of light conveys information about the transmitting medium. For example, in the case of a bee, retinotopic vision allows it to learn and recognize the state of partial polarization of the skylight depending on the sun position, therefore allowing the bee to assess and communicate the locations of vital resources. When light travels through anisotropic media, its polarization state is modified due to natural and/or induced birefringence whose magnitude and orientation is often directly related to characteristics of devices or of living cells. Knowing the polarization state of the light incident upon a sample, the detection and analysis of the polarization state of the transmitted light allow for determination of the sample birefringence distribution. This motivates the need for developing quantitative techniques which enable the accurate measurement of the retardation magnitude and orientation leading to the determination of a sample's physical properties.

In crystallography, growth-induced birefringence arises from lattice mismatch in rare-earth garnets grown from the melt. This is an undesirable attribute for crystals that are to be used as substrates for magnetic devices or laser host crystals. This motivates the need for measuring and monitoring the growth-induced birefringence.

In fluid mechanics, using a differential interference polarization interferometer, white light interference colors are produced due to refractive index variations in a two-dimensional flow. Analysis of the white light interference colors leads to the quantitative determination of the fluid temperature and density gradient.

In biology, birefringence imaging has become a powerful tool for the dynamic observation of the growth cones of developing neurites and of the bundled microtubules in living cells. Birefringence imaging using polarization interference microscopy reveals details about the cell structure during the various stages of transformation. More recently, birefringence has been related to the retinal nerve fiber layer in the human eye and its measurement may lead to an early detection of glaucoma.

In thin films, the reflection or transmission of polarized light introduces a phase shift whose accurate measurement can allow the determination of the film thickness, refractive index, and extinction coefficient.

In transparent materials such as glass and plastic, birefringence is induced by residual stress. Using the stress-optic effect, stress-induced birefringence measurements are used for quality control and quality enhancement by monitoring the amount of stress in selected locations.

Residual stress also significantly impacts the lifetime, reliability, and failure modes of micromachined and microelectronic devices. High levels of residual stress may lead to cracking and delamination in thin films and interconnects, thus motivating the need for measuring and controlling the level of stress in those devices. In technologies such as Micro Electrical Mechanical Systems (MEMS), parameters such as mirror curvature may be controlled by adjusting the amount of residual stress in electropated nickel films adding one more degree of freedom to the system.

In optical communications, residual stress affects the performance of optical fibers and planar waveguides. For example, residual stress determines the amount of Polarization Mode Dispersion (PMD) in optical fibers. Stress-induced birefringence measurements in optical fibers delineate the roles of thermal and mechanical stress. These measurements also allow the influence of OH impurity on the total residual stress to be quantified. They also allow the residual stress to be related to the refractive index change. Stress-induced birefringence measurements are useful to understand the mechanisms of stress relaxation occurring during the fabrication of long-period fiber gratings using $CO_2$ laser irradiation. Stress-induced birefringence measurements are also useful in the design of polarization-maintaining optical fibers and waveguides, which can lead to the fabrication of fiber gyroscopes, polarization-maintaining fiber amplifiers, PMD emulators, PMD compensators, and polarization-insensitive arrayed waveguide gratings routers.

Several techniques have been developed to measure retardation magnitude and orientation. Photoelastic measurements involve the use of circular polariscopes, i.e., polarizers and quarter waveplates, together with intensity measurements to retrieve the retardation magnitude of a sample. The use of quarter waveplates affects the accuracy of the technique especially when it is used in white light.

Based on the photoelasticity principle, Spectral Content Analysis (SCA) uses a circular polariscope and a CCD camera in white-light to allow full-field retardation measurements. This technique is also subject to error due to the use of quarter waveplates and often only takes into account a finite number of wavelengths of the transmitted light discriminating most of the optical signal. Further, these techniques typically can not detect very-low level birefringence such as that present in optical fibers and waveguides.

Recently, photoelastic modulators have been used to modulate the polarization state of the light traveling through an optical system composed of polarizers and the sample under investigation. It has been shown that the frequency demodulation of the transmitted optical signal leads to accurate measurements of the low-level retardation magnitude and orientation of the sample. This technique however possesses a low spatial resolution on the order of a millimeter which renders virtually impossible the profiling of devices such as optical fibers and waveguides.

In biology, polarization microscopy has proven to be very effective in detecting very-low level birefringence in living cells. The use of compensators allows the detection of very low-level birefringence. More recently, a new liquid-crystal-based compensator has been added to a polarization microscope to allow the detection of low-level retardation magnitude and orientation in living cells. A finite number of sample images are recorded for various birefringence settings of the compensator. For each pixel, the different intensities recorded allow a system of intensity equations to be solved for the two unknowns corresponding to the retardation magnitude and orientation of the sample. The technique relies, however, on the accurate measurement of the light intensity and the compensator used is not a conventional, simple, commercially-available compensator.

Another well-known technique to measure low-level birefringence is based on the Brace-Köhler compensator. The method includes finding a minimum of intensity by rotating a compensator plate when a sample is observed between crossed polarizers. The measured compensator angle relative to the compensator extinction position when no sample is in the light path allows the determination of the unknown retardation. The technique however uses a small retardation approximation and an intensity minimum is found rather than complete extinction. This may adversely affect the accuracy of the measurement. Furthermore, the Brace-Köhler compensator technique assumes that the sample retardation orientation is known.

When using monochromatic light for low-level retardation measurements, there is a need for a method based on finding a null of intensity (or extinction) which is more accurately measurable than a light intensity minimum or the absolute light intensity. A retardation measurement technique is presented for full-field evaluation. In monochromatic light, the Automated Two-Waveplate Compensator (ATWC) technique is developed. It is based on rotating a waveplate of known retardation to produce linearly polarized light when a sample is placed between polarizers. Extinction is obtained by rotating the analyzer so it is perpendicular to the polarization direction. The ATWC technique is implemented by using a polarization microscope, a mercury arc source, and a waveplate of known retardation. The sample's retardation orientation is first determined at all points of the image by rotating the microscope stage to determine which orientation produces extinction. The sample's retardation magnitude is then determined at all points by finding which compensator angle produces linearly polarized light as previously described.

The Brace-Köhler compensator retardation measurement method, also known as the elliptic compensator method, includes finding a minimum of intensity by rotating a compensator waveplate in order to determine a sample retardation. The two waveplates are placed between crossed polarizers. With the sample at 45 degrees from extinction, the compensator angle producing a minimum, and measured from the compensator extinction position, allows the calculation of the sample retardation Rs, $$Rs = -Rc \sin(2\theta c) \quad (1)$$

with $R_C$ the compensator retardation, and $\theta c$ the compensator angle. Eq. (1) is valid if the compensator retardation is greater than the sample retardation. When the sample retardation is greater, the role of both waveplates are inverted and the sample is rotated until an intensity minimum is obtained in which case the sample retardation is computed using, $$R_s = -\frac{R_c}{\sin(2\theta_s)} \quad (2)$$

Figure 2:
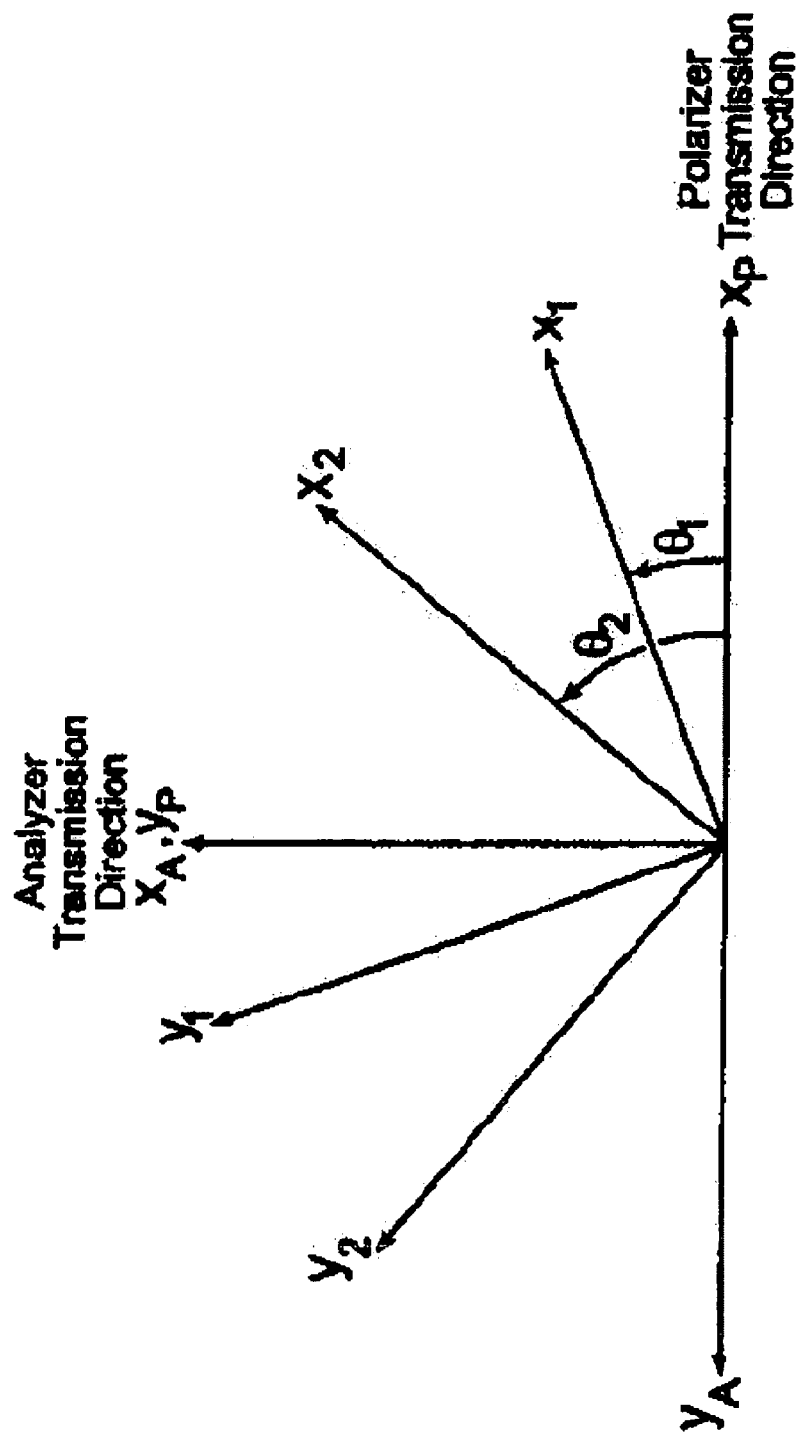
FIG. 2 is a graph illustrating the polarization directions of the polarizer and analyzer of FIG. 1, in addition to the slow and fast axes of the waveplates of FIG. 1.

The analysis and the understanding of the working principle of the Brace-Köhler compensator leads to a development of a numerical tool to calculate the light intensity transmitted through the optical system. The optical elements to be considered in the Brace-Köhler compensator case are represented in FIG. 1. Two waveplates 115, 120 producing respectively retardations $\phi_1$ and $\phi_2$ are placed between crossed polarizers. The orientations of their slow axes 140, 145 relative to the polarizer transmission direction, T, are respectively $\theta_1$ and $\theta_2$. Jones calculus is used to determine the output intensity. The Jones transmission matrices of Waveplate 1 and Waveplate 2 are respectively $T(\phi_1)$ and $T(\phi_2)$ in FIG. 1, and the Jones rotation matrices corresponding to the angle between the polarizer transmission direction, T, and the slow axes 140, 145 of Waveplate 1 and Waveplate 2 are $R(\theta_1)$ and $R(\theta_2)$. The different systems of axes for each optical element are represented in FIG. 2. The polarization transmission directions of the polarizer and the analyzer are respectively $x_P$ and $x_A$ whereas the slow axes of the waveplates of retardation $\phi 1$ and $\phi 2$ are respectively $x_1$ and $x_2$ in FIG. 2.

The output light intensity is computed by calculating first the Jones vector, $\vec{\epsilon}_A$ in the system of the analyzer after traveling through the optical system $$\vec{\varepsilon}_A = R\left(\frac{\pi}{2} - \theta_2\right) T(\phi_2) R(\theta_2 - \theta_1) T(\phi_1) R(\theta_1) \begin{pmatrix} 1 \\ 0 \end{pmatrix} \quad (3)$$

with rotation matrices $R(\theta_1)$, $R(\theta_2 - \theta_1)$ and $$R\left(\frac{\pi}{2} - \theta_2\right)$$

representing respectively rotations of angle $\theta_1$, $\theta_2$, $\theta_1$, and $$\frac{\pi}{2} - \theta_2,$$

transmission matrices $T(\theta_1)$ and $T(\theta_2)$ representing transmission through the waveplates of retardations $\phi_1$ and $\phi_2$. Normalizing the Jones vector exiting the first polarizer, the Jones vector $\vec{\varepsilon}_A$ exiting the analyzer is given by $$\vec{\varepsilon}_A = \begin{pmatrix} \sin\theta_2 & \cos\theta_2 \\ -\cos\theta_2 & \sin\theta_2 \end{pmatrix} \begin{pmatrix} 1 & 0 \\ 0 & \exp^{j\phi_2} \end{pmatrix} \begin{pmatrix} \cos(\theta_2-\theta_1) & \sin(\theta_2-\theta_1) \\ -\sin(\theta_2-\theta_1) & \cos(\theta_2-\theta_1) \end{pmatrix} \quad (4)$$

$$\begin{pmatrix} 1 & 0 \\ 0 & e^{j\phi_1} \end{pmatrix} \begin{pmatrix} \cos\theta_1 & \sin\theta_1 \\ -\sin\theta_1 & \cos\theta_1 \end{pmatrix} \begin{pmatrix} 1 \\ 0 \end{pmatrix}$$

Performing the matrix multiplication, $$\vec{\varepsilon}_A = \begin{pmatrix} \sin\theta_2\cos\theta_1\cos(\theta_2-\theta_1) - \sin\theta_2\sin\theta_1\sin(\theta_2-\theta_1)e^{j\phi_1} - \\ \cos\theta_2\cos\theta_1\sin(\theta_2-\theta_1)e^{j\phi_2} - \cos\theta_2\sin\theta_1\cos(\theta_2-\theta_1)e^{j(\phi_1\phi_2)} - \\ \cos\theta_2\cos\theta_1\sin(\theta_2-\theta_1) + \cos\theta_2\sin\theta_1\sin(\theta_2-\theta_1)e^{j\phi_1} - \\ \sin\theta_2\cos\theta_1\sin(\theta_2-\theta_1)e^{j\phi_2} - \sin\theta_2\sin\theta_1\cos(\theta_2-\theta_1)e^{j(\phi_1+\phi_2)} \end{pmatrix} \quad (5)$$

The component of the Jones vector corresponding to the analyzer transmission direction is the component along the $x_A$ axis of the analyzer system according to the convention defined in FIG. 2. The intensity $I_A$ transmitted through the analyzer can thus be computed $$I_A = \varepsilon_{Ax}\varepsilon_{Ax}^* \quad (6)$$

$$= \sin^2\theta_2\left\{\cos^2\theta_2\cos^2\frac{\phi_1}{2} + \cos^2(2\theta_1-\theta_2)\sin^2\frac{\phi_1}{2}\right\} +$$

$$\cos^2\theta_2\left\{\sin^2\theta_2\cos^2\frac{\phi_1}{2} + \sin^2(2\theta_1-\theta_2)\sin^2\frac{\phi_1}{2}\right\} -$$

$$\frac{1}{2}\sin 2\theta_2\left\{\sin 2\theta_2\cos^2\frac{\phi_1}{2}\cos\phi_2 - \sin(4\theta_1 - 2\theta_2)\cos\phi_2\sin^2\frac{\phi_1}{2} - \sin 2\theta_1\sin\phi_1\sin\phi_2\right\}$$

The above expression represents the intensity transmitted through an optical system composed of two waveplates arbitrarily oriented and placed between crossed polarizers. Having normalized the Jones vector characteristic of the electric field transmitted through the first polarizer, Eq. (6) allows the computation of the intensity transmitted through the optical elements relative to that exiting the first polarizer.

In the particular case of the Brace-Köhler compensator, the fixed waveplate is oriented at 45 degrees from extinction. Assuming the fixed waveplate produces the phase-shift $\phi_1$ in FIG. 1 and the rotating waveplate produces the phase-shift $\phi_2$, the relative intensity $I_{BK}$ transmitted in the case of the Brace-Köhler compensator can be computed by substituting $\theta_1$ equal $\pi/4$ in Eq. (6)

$$I_{BK} = I_A\left(\theta_1 = \frac{\pi}{4}\right) \quad (7)$$

$$= 2\sin^2\theta_2\cos^2\frac{\phi_1}{2} + \sin^2\frac{\phi_1}{2}\{\sin^4\theta_2 + \cos^4\theta_2\} -$$

-continued $$\frac{1}{2}\sin 2\theta_2\left\{\sin 2\theta_2\cos^2\frac{\phi_1}{2}\cos\phi_2 - \sin 2\theta_2\cos\phi_2\sin^2\frac{\phi_1}{2} - \sin\phi_1\sin\phi_2\right\}$$

Using trigonometric identities, Eq. (7) can be simplified to $$I_{BK\perp} = \sin^2 2\theta_2\cos\phi_1\sin^2\frac{\phi_2}{2} + \frac{1}{2}\sin 2\theta_2\sin\phi_1\sin\phi_2 + \sin^2\frac{\phi_1}{2} \quad (8)$$

where the subscript $\perp$ indicates that the polarizers are crossed. A similar approach allows the derivation of the intensity between parallel polarizers by considering the Jones vector component along the $y_A$ axis of the analyzer system $$I_{BK\parallel} = \sin^2 2\theta_2\cos\phi_1\sin^2\frac{\phi_2}{2} - \frac{1}{2}\sin 2\theta_2\sin\phi_1\sin\phi_2 + \sin^2\frac{\phi_1}{2} \quad (9)$$

Assuming no reflection or absorption of the optical system, both intensities satisfy $$I_{BK\perp} + I_{BK\parallel} = 1 \quad (10)$$

The Brace-Köhler compensator retardation measurement method assumes that the retardations of the sample and the compensator are small. Under the small retardation approximation, Eq. (8) leads to the following intensity $$I_{APX} = \left(\frac{\phi_1}{2} + \frac{\phi_2}{2}\sin 2\theta_2\right)^2 \quad (11)$$

with $I_{APX}$ representing the transmitted intensity under the small retardation approximation. Under this approximation, a null of intensity is obtained when $$\frac{\phi_1}{2} + \frac{\phi_2}{2}\sin 2\theta_2 = 0 \quad (12)$$

$$\phi_1 = -\phi_2\sin 2\theta_2$$

Note that Eq. (12) is valid only if $\phi_1 \leq \phi_2$, i.e. the retardation of the fixed waveplate is less than or equal to the retardation of the rotating waveplate. When the sample retardation is less than or equal to the compensator retardation, the sample waveplate is fixed at 45 degrees from extinction and the compensator waveplate is rotated. The phase shift $\phi_1$ produced by the sample is then given by Eq. (12). When the sample retardation is greater than the compensator retardation, the compensator waveplate is fixed at 45 degrees from extinction and the sample waveplate is rotated. The phase shift $\phi_2$ produced by the sample is then given by $$\phi_2 = -\frac{\phi_1}{\sin 2\theta_2} \quad (13)$$

The transmitted intensities calculated using Eq. (8) and Eq. (11) are plotted in FIG. 3. The compensator retardation $\phi_2$ is equal to $\lambda/10$ as it is the value of a commercially available Brace-Köhler compensator manufactured by Olympus. The sample retardation $\phi_1$ is arbitrarily chosen to be equal to $\lambda/18$. The intensity minima produced when the compensator is rotated are not nulls of intensity. The reason complete extinction can not readily be produced with the Brace-Köhler compensator can be understood by determining the successive polarization states of the light in the two-waveplate system of FIG. 3. It will be seen later how the compensator angle producing minimum of intensity is calculated analytically. The successive polarization states when the compensator waveplate is rotated to produce an intensity minimum are shown in FIG. 4. These polarization states have been determined using the waveplates retardations values of FIG. 3. After traveling through the sample, the light is elliptically polarized and the principal axes of the ellipse traced by the electric field coincide with the polarization transmission directions of the crossed polarizers. This ellipse of polarization is represented by the dashed line in FIG. 4. The compensator angle for obtaining a minimum of intensity along the transmission direction of the analyzer for $\phi_1=\lambda/18$ and $\phi_2=\lambda/10$ is equal to $-17.03°$. The electric field exiting the compensator is calculated using Jones calculus and the corresponding ellipse of polarization is shown as a solid line 410 in FIG. 4. The electric field exiting the compensator is elliptically polarized. The major axis of the ellipse traced by the electric field incident upon the analyzer makes an angle equal to $2.4°$ with respect to the polarizer transmission direction. In the Brace-Köhler configuration, the minimum of intensity which is obtained by rotating the compensator plate, corresponds to the case in which the ellipse traced by the electric field transmitted by the two waveplates produces the smallest component along the analyzer transmission direction.

Further analysis reveals the conditions that govern the existence and location of the intensity minima observed as the compensator is rotated. The first and second derivatives of the intensity as a function of the rotating waveplate orientation $\theta_2$ are obtained from Eq. (8) as $$\frac{\partial I_{BK}}{\partial \theta_2} = \cos 2\theta_2 \{2\sin 2\theta_2 \cos\phi_1(1-\cos\phi_2) + \sin\phi_1 \sin\phi_2\} \quad (14)$$

and $$\frac{\partial^2 I_{BK}}{\partial \theta_2^2} = 8 \cos\phi_1 \sin^2\frac{\phi_2}{2} - 16\sin^2 2\theta_2 \cos\phi_1 \sin^2\frac{\phi_2}{2} - 2\sin 2\theta_2 \sin\phi_1 \sin\phi_2 \quad (15)$$

Figure 3:
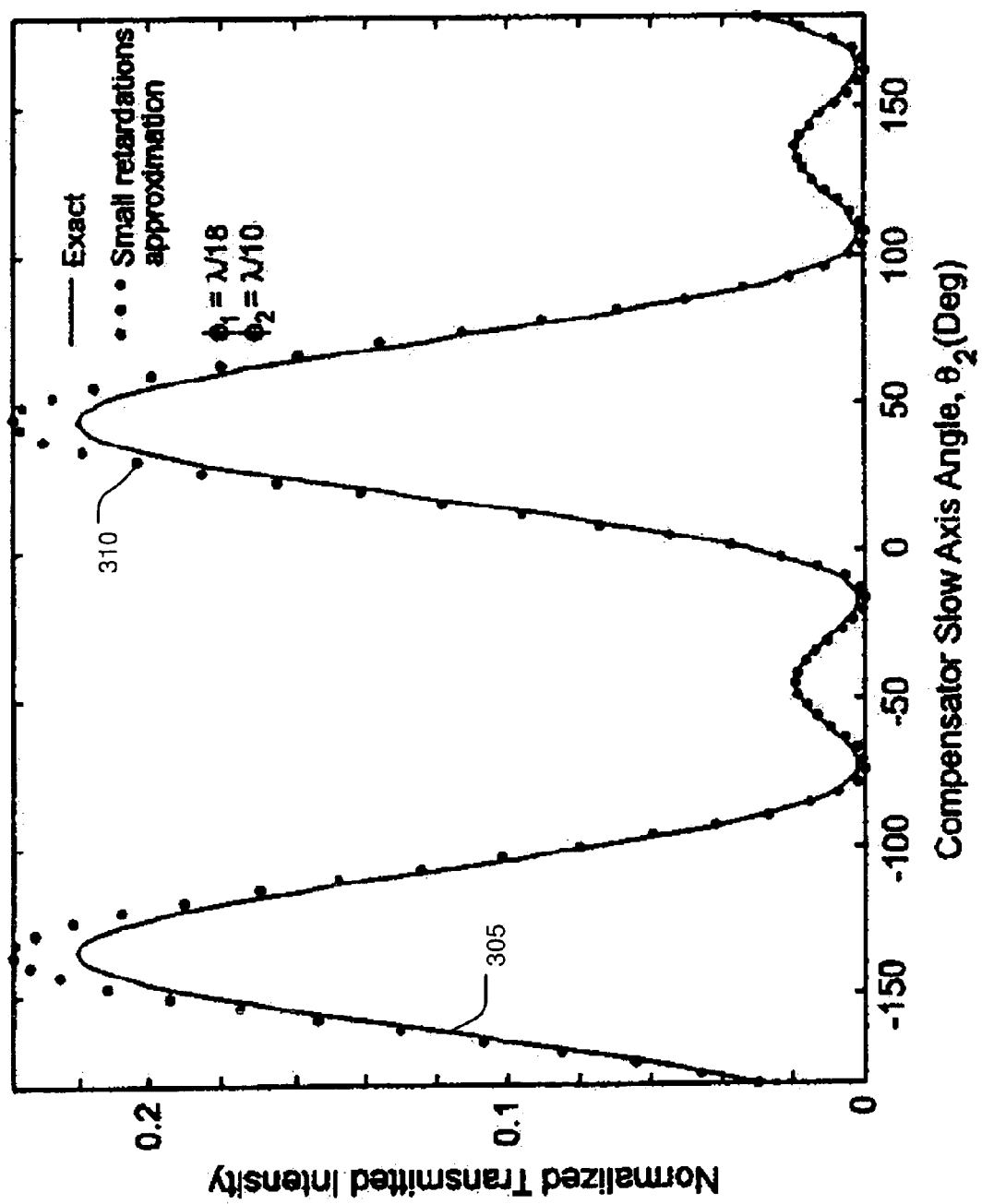
FIG. 3 is a graph illustrating the difference between calculated transmission intensities using both a small retardation approximation and an exact mathematical computation.
Figure 4:
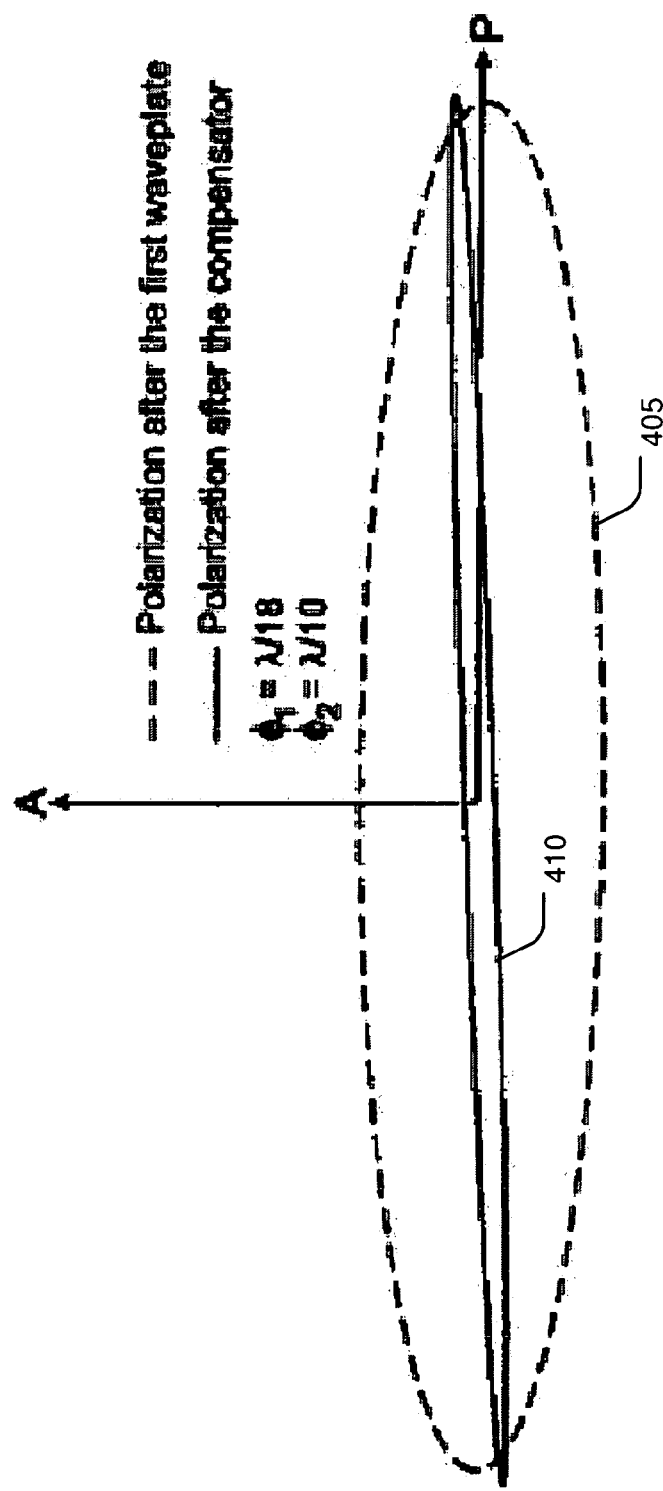
FIG. 4 is a graph illustrating a particular polarization that results from a given sample retardation and a given compensator retardation.
Figure 5A:
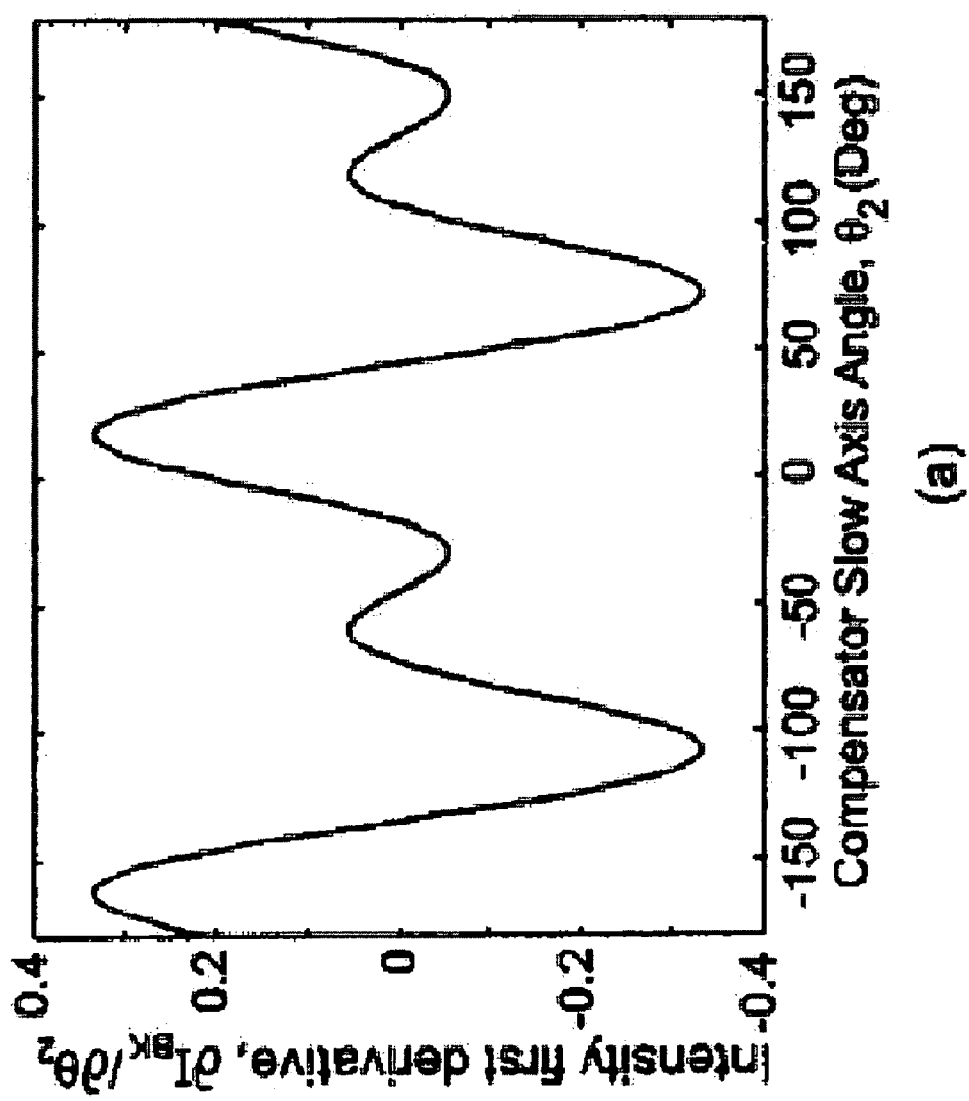
FIGS. 5A and 5B are graphs illustrating the first and second derivatives of the graph of FIG. 3.
Figure 5B:
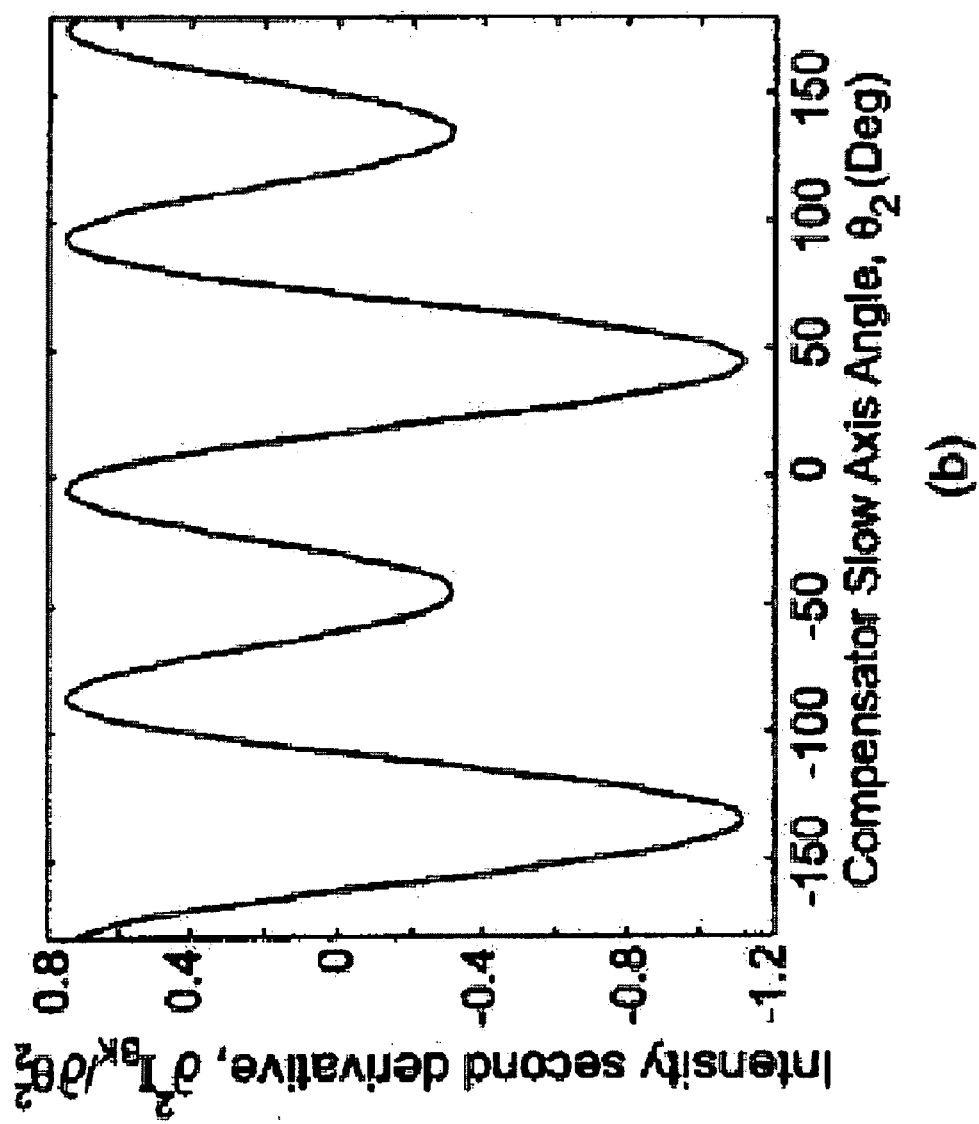

The first and second derivatives of the intensity $I_{BK}$ represented in FIG. 3 are plotted in FIG. 5. The locations of the extrema of intensity are given by Eq. (14) when $$0 = \cos 2\theta_2 \{2 \sin 2\theta_2 \cos \phi_1(1-\cos \phi_2)+\sin \phi_1 \sin \phi_2\} \quad (16)$$

There is a first group of intensity extrema which occur for $\cos \theta_2 = 0$, i.e., $\theta_2 = (2n+1)\times 45$ degrees where n is an integer. For the case represented in FIG. 3, these correspond to the global and local intensity maxima observed at $-135$, $-45$, $+45$ and, $+135$ degrees. These maxima positions are also seen in FIG. 5(a) of the first intensity derivative. These intensity extrema, whether they are minima or maxima, are "non-retardation-based" extrema as they are observed for $\theta_2=(2n+1)\times 45$ degrees independently of the retardation values $\phi_1$ and $\phi_2$. As a consequence, finding the rotating waveplate angle for which they occur does not bring any quantitative information about the waveplates retardations. Substituting $\theta_2$ to equal 45 and $-45$ degrees in Eq. (8), the normalized transmitted intensity of the non-retardation-based extrema is given as a function of $\phi_1$ and $\phi_2$ $$I_{NRBI}(\theta_2 = +45°) = \sin^2\left(\frac{\phi_1 + \phi_2}{2}\right) \quad (17)$$

$$I_{NRBI}(\theta_2 = -45°) = \sin^2\left(\frac{\phi_1 - \phi_2}{2}\right) \quad (18)$$

The second group of intensity extrema occur for the second factor in Eq. (14) equal to zero. The analytical expression of the rotating waveplate angle $\theta_2$ to produce these intensity extrema is given by $$\sin 2\theta_2 = \frac{\sin\phi_1 \sin\phi_2}{2\cos\phi_1(\cos\phi_2 - 1)} \quad (19)$$

Unlike the non-retardation-based extrema, this second group of extrema occur if $$\left\|\frac{\sin\phi_1 \sin\phi_2}{2 \cos\phi_1(\cos\phi_2 - 1)}\right\| \quad (20)$$

Provided that the retardations $\phi_1$ and $\phi_2$ satisfy Eq. (20), four "retardation-based" intensity extrema occur as the rotating plate is rotated from 0 to 360 degrees and their angular position is given by $$\sin\{2\theta_2\}=\sin\{2(\theta_2+180°)\}=\sin\{2(90°-\theta_2)\}=\sin\{2(-90°-\theta_2)\} \quad (21)$$

In the case represented in FIG. 3, these extrema are intensity minima and occur for $\theta_2$ equal to $-72.97$, $-17.03$, $107.03$, and $162.97$ degrees. The angle $\theta_2$ for which they are observed is a function of the retardation values $\phi_1$ and $\phi_2$. As a consequence, varying the angle $\theta_2$ until these retardation-based extrema are observed and knowing one waveplate retardation $\phi_1$ or $\phi_2$ allows the determination of the other waveplate retardation respectively $\phi_1$ or $\phi_2$ using Eq. (19). It can be shown that for small retardations $\phi_1$ and $\phi_2$, Eq. (19) leads to the small retardation approximation formulas Eqs. (1) and (2). Eq. (19) provides an exact formula for the calculation of the unknown retardation when using the Brace-Köhler compensator technique, without restricting it to small retardations. It can therefore not only lead to more accurate retardation measurements, but also extend the range of compensator and sample retardations over which the Brace-Köhler compensator technique is applicable. Substituting Eq. (19) in Eq. (8), the normalized intensity of the retardation-based extrema can be computed as a function of $\phi_1$ and $\phi_2$ as $$I_{RB} = \sin^2\frac{\phi_1}{2} - \frac{\sin^2\phi_1 \sin^2\phi_2}{16 \cos\phi_1 \sin^2\left(\frac{\phi_2}{2}\right)} \quad (22)$$

Figure 6:
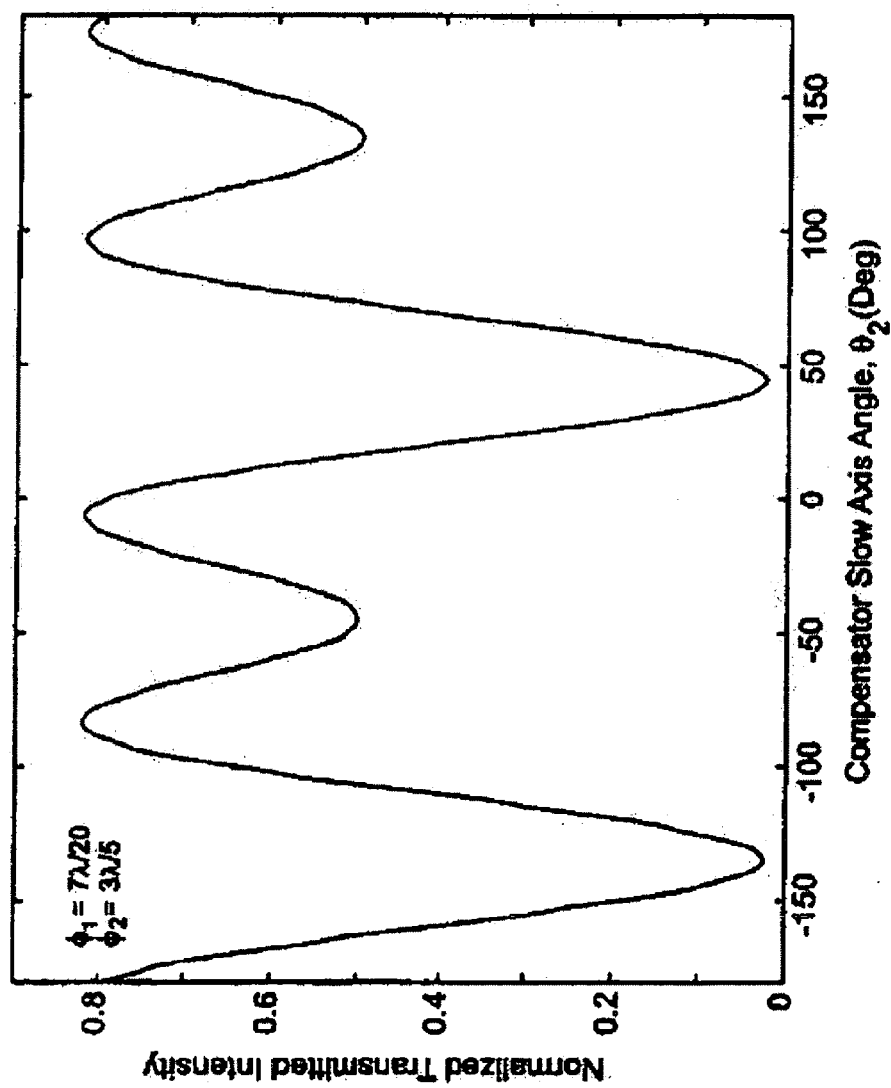
FIG. 6 is a graph illustrating a particular normalized transmitted intensity that results from a given sample retardation and a given compensator retardation.

If the intensity of the retardation-based extrema is greater than that of the non-retardation-based extrema, global intensity maxima are observed whenever $\theta_2$ satisfies Eq. (19) and local and global minima are observed for $\theta_2=(2n+1)\times 45$ degrees. This is illustrated in FIG. 6 for which the fixed waveplate retardation $\phi_1=7\lambda/20$ and the rotating waveplate retardation $\phi_2=3\lambda/5$. The retardation-based extrema are maxima and occur for $\theta_2$ equal to $-83.54$, $-6.46$, $96.46$, and $173.54$ degrees. For these retardations, the Brace-Köhler compensator technique is inapplicable since the intensity minima are non-retardation-based extrema.

Figure 7:
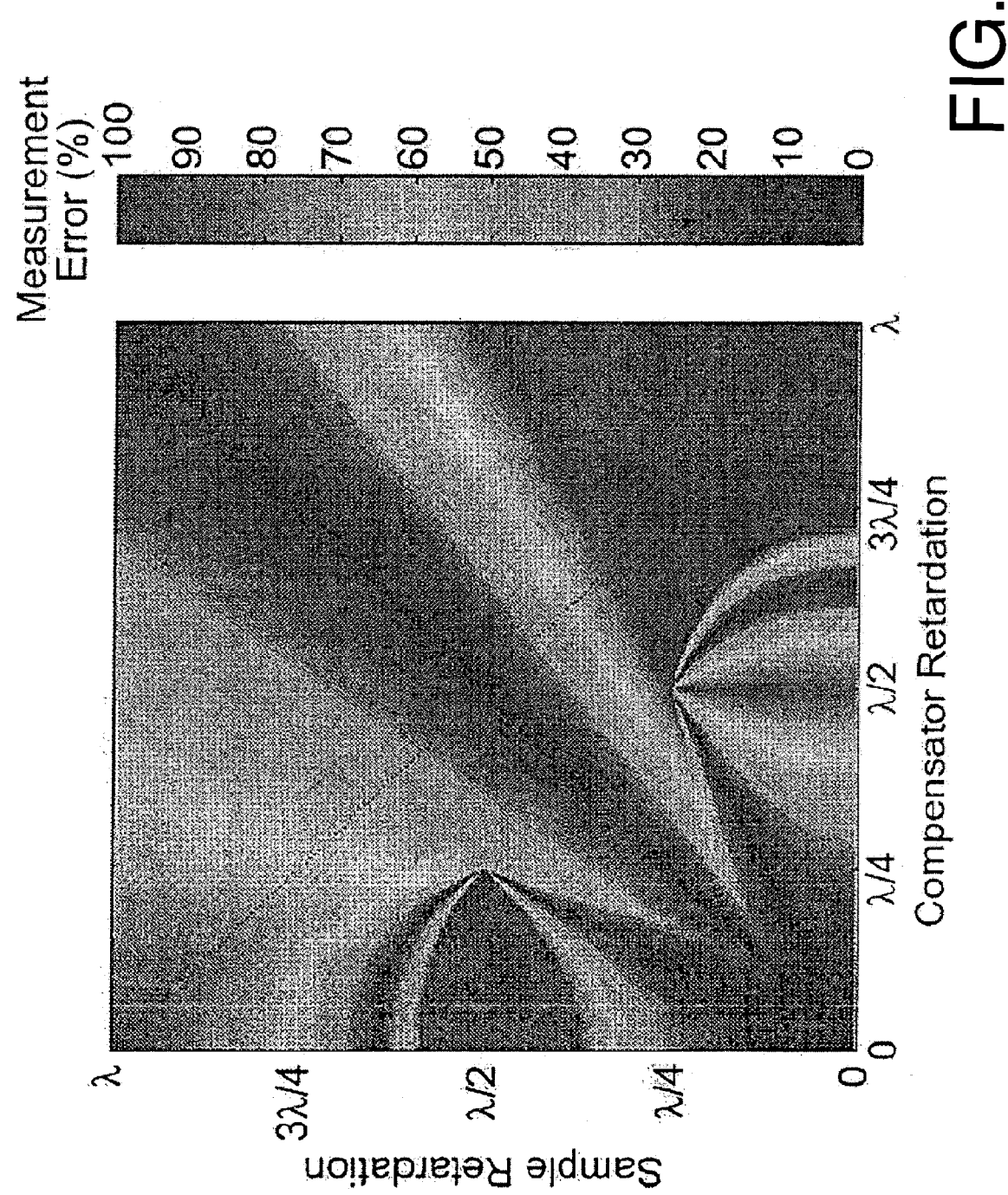
FIG. 7 is a graph illustrating errors introduced by using a small retardation approximation approach.

Having derived the expression of the intensity transmitted through a two-waveplate system placed between crossed polarizers, and the expression of the location and magnitude of the retardation-based extrema as Waveplate 2 is rotated (FIG. 1), the error due to the small retardation approximation in the Brace-Köhler compensator formula can be calculated. This error is represented in FIG. 7 for sample and compensator retardations ranging from 0 to $\lambda$. To generate FIG. 7, it was first determined, for each pair of sample and compensator, which of the two waveplates was to be rotated in the Brace-Köhler compensator sense, i.e., the rotating waveplate retardation must be greater than that of the fixed plate. The angles $\theta_2$ producing global retardation-based intensity minima respectively maxima and the angles $\theta_2$ producing global and local non-retardation-based intensity maxima respectively minima are determined using Eqs. (17), (18), (19), (20), and (22). Having found the location of the intensity minimum and knowing the retardation of the compensator which is on the x-axis of FIG. 7, the sample retardation is calculated using Eqs. (1) or (2). The calculated value is compared to the true value of the sample and the relative error is plotted as a percentage of the true value. The error remains low for relatively small retardations as expected. For compensator and sample retardations less than a quarter of a wavelength, the error remains lower than 20%. The error is zero for particular cases. When both waveplates have equal retardations, the intensity minimum occurs when the rotating waveplate slow axis is parallel to the fixed waveplate fast axis. Having for convention that the fixed waveplate slow axis is at 45 degrees from the polarizer transmission direction, the rotating waveplate should be at $-45$ degrees to obtain extinction. In this case, the Brace-Köhler compensator formula Eq. (1) calculates accurately the sample retardation. Another particular case occurs when the rotating waveplate has twice the retardation than that of the fixed waveplate. By substituting $\phi_1$ and $\phi_2$ in the derivative of the intensity with respect to $\theta_2$, Eq. (14), it can be shown that an extremum occurs for the following condition $$\sin(2\theta_2) = \frac{\sin\phi_1 \sin(2\phi_1)}{2\cos\phi_1[\cos(2\phi_1)-1]} = -\frac{1}{2} \qquad (23)$$

Figure 8:
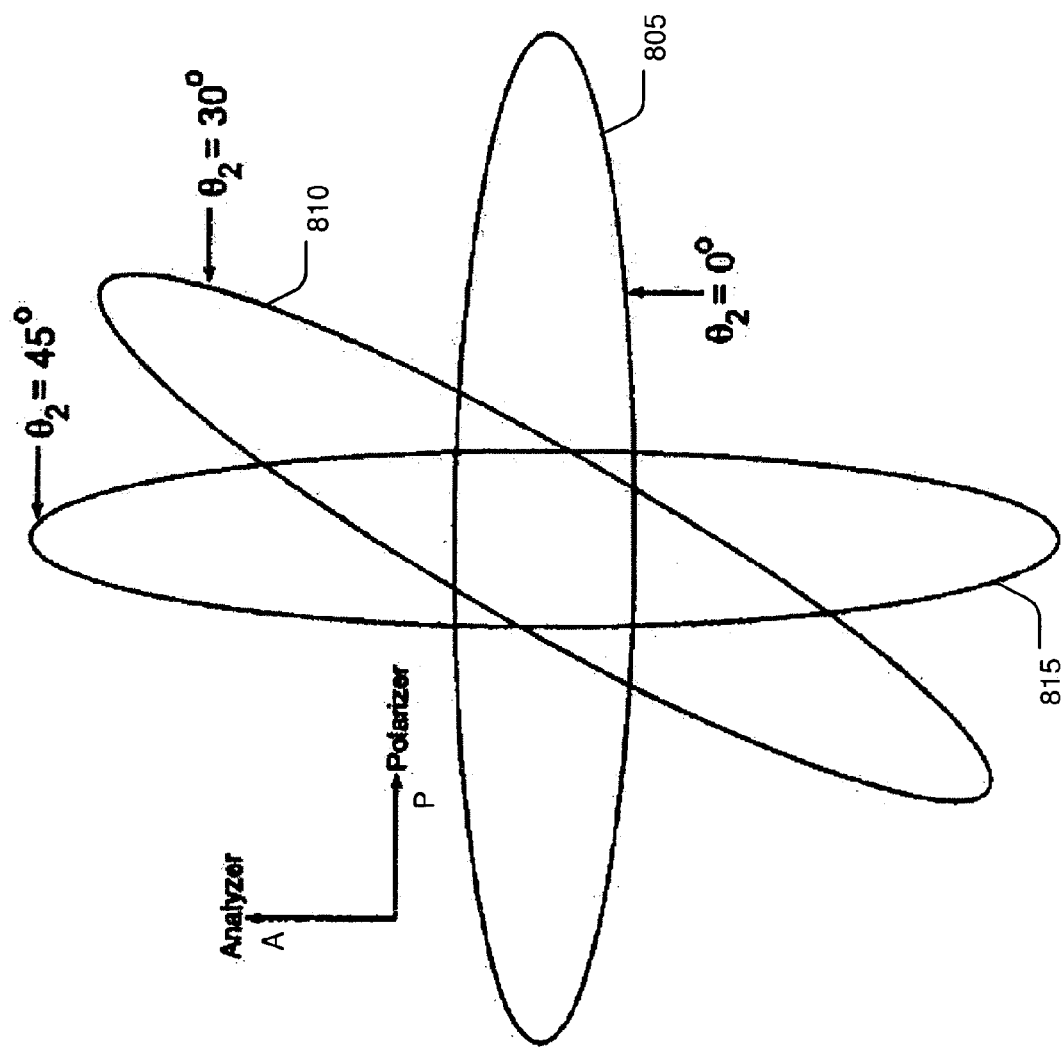
FIG. 8 is a graph illustrating polarization of light for various values of $\theta_2$.

The angles $\theta_2$ producing intensity minimum are given by the equation above and are equal to $-75$, $-15$, $105$, and $165$ degrees. Substituting these values of $\theta_2$ in the Brace-Köhler formulas Eqs. (1) and (2) lead to $R_c=2R_s$ or vice versa rendering the small retardation approximation formulas accurate. Note also that the error peaks for either waveplate retardation equal to a half-wavelength. This can be understood with the aid of FIG. 8, which represents the ellipse traced by the electric field traveling through a two-waveplate system when the rotating waveplate is a half-waveplate. The different orientations of the rotating waveplate are indicated by $\theta_2$ and the polarization ellipses are represented in the system defined by the polarization transmission directions of the crossed polarizers. The half-waveplate has for effect of rotating the ellipse of polarization produced after the first waveplate. As a matter of fact, for a given orientation $\xi$ of the half-waveplate, the ellipse of polarization after the first waveplate is rotated by $2\xi$. The first waveplate being oriented at 45 degrees from extinction, the polarization transmission directions of the crossed polarizers are parallel to the principal axes of the ellipse of polarization traced by the electric field transmitted by the first waveplate. Consequently, the minimum of intensity is obtained when the ellipse minor axis of the light transmitted by the second waveplate is parallel to the analyzer polarization transmission direction. This is the case for $\theta_2$ equal to zero as shown in FIG. 8. When $\theta_2=0$ is substituted in the Brace-Köhler compensator formulas Eqs. (1) and (2), it results to relative errors respectively equal to 100% and $\phi$.

Experimentally, a commercial Brace-Köhler compensator is not rotatable over a full 360 degree revolution. Since all four retardation-based minima are analytically equivalent, only one needs to be found to determine the unknown retardation. The compensator manufactured by Olympus is rotatable from approximately $-50$ degrees to $+50$ degrees. Over this range, three extrema are observed provided that the compensator and sample retardations satisfy Eq. (20): two non-retardation-based maxima (respectively minima) for $\theta_2$ equal to $-45$ degrees and $+45$ degrees, and one retardation-based minimum (respectively maximum) for $\theta_2$ given by Eq. (19). However, for a given retardation $\phi_2$ there is a maximum retardation $\phi_1$ beyond which Eq. (20) is not satisfied and the retardation-based extremum located between $\theta_2$ equal $-45$ and $+45$ degrees collapses into one of these latter extrema. This maximum value $\phi_{L1}$ can be computed with Eq. (20) by substituting $\theta_2=\pi/4$ $$\phi_{L1} = \arctan\left\{2\frac{1-\cos\phi_2}{\sin\phi_2}\right\} \qquad (24)$$

Figure 9:
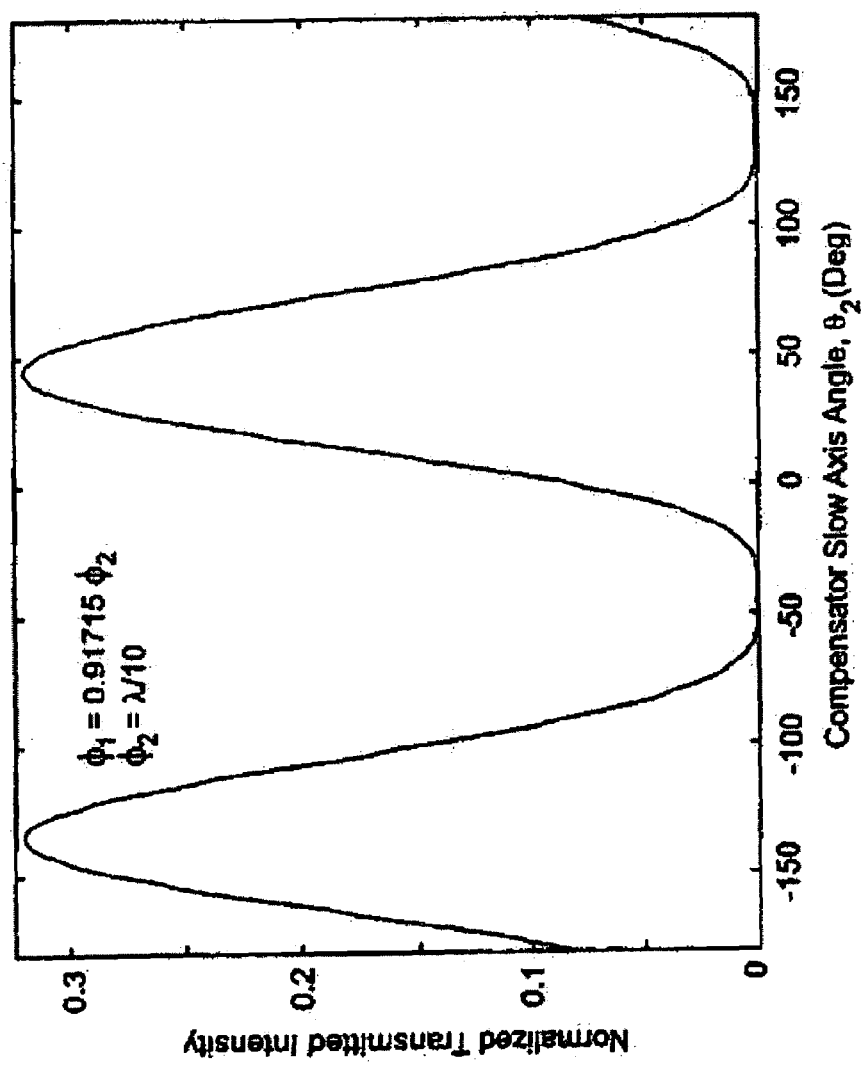
FIG. 9 is a graph illustrating normalized transmitted intensity for a particular configuration.
Figure 10A:
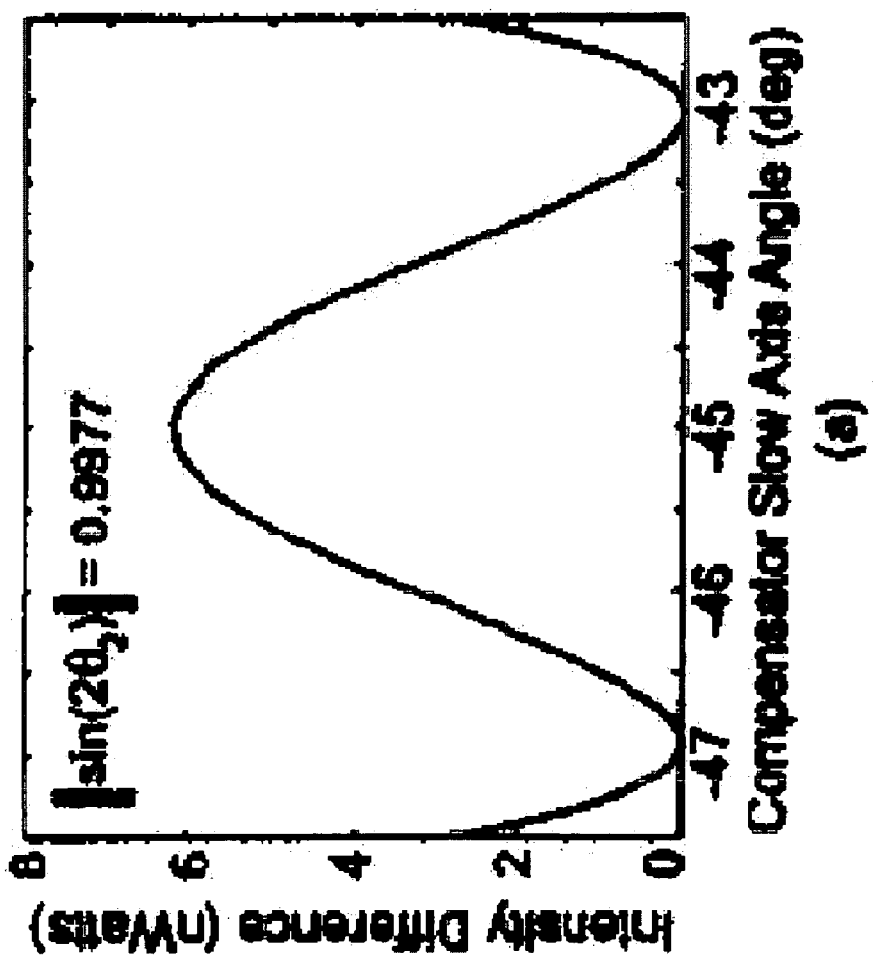
FIGS. 10A through 10E are graphs illustrating resolvability for a particular system configuration in a Brace-Köhler compensator technique.
Figure 10B:
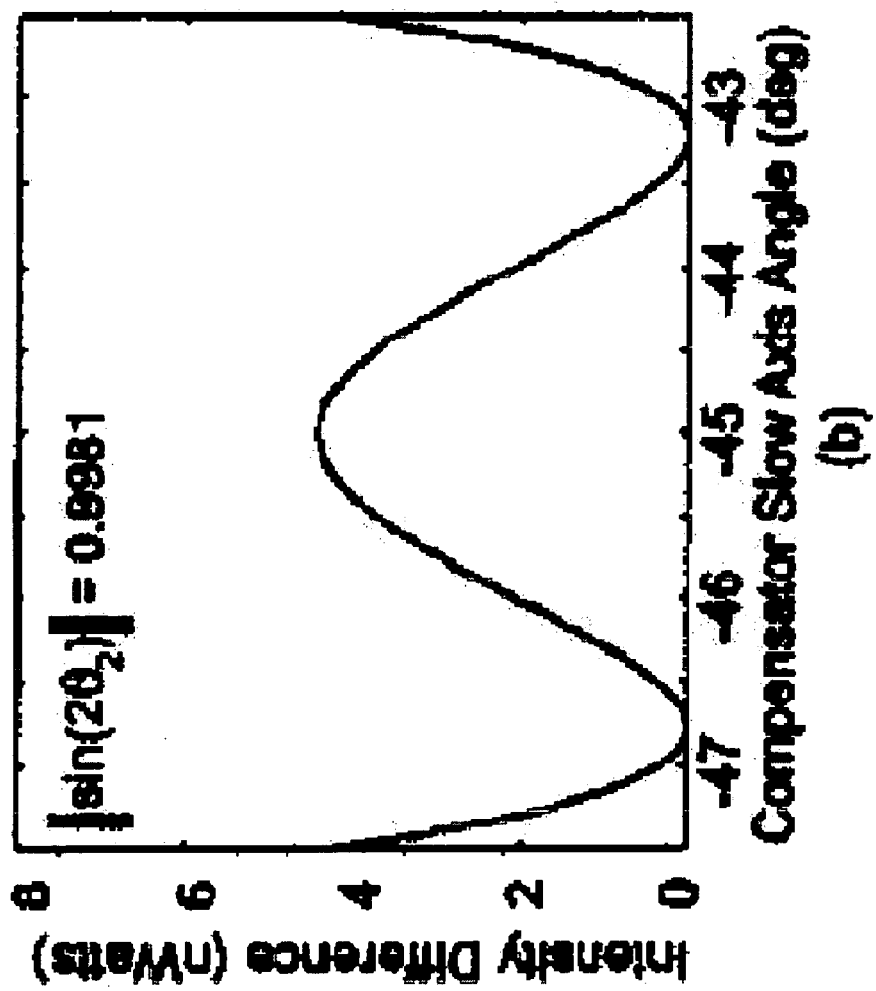
Figure 10C:
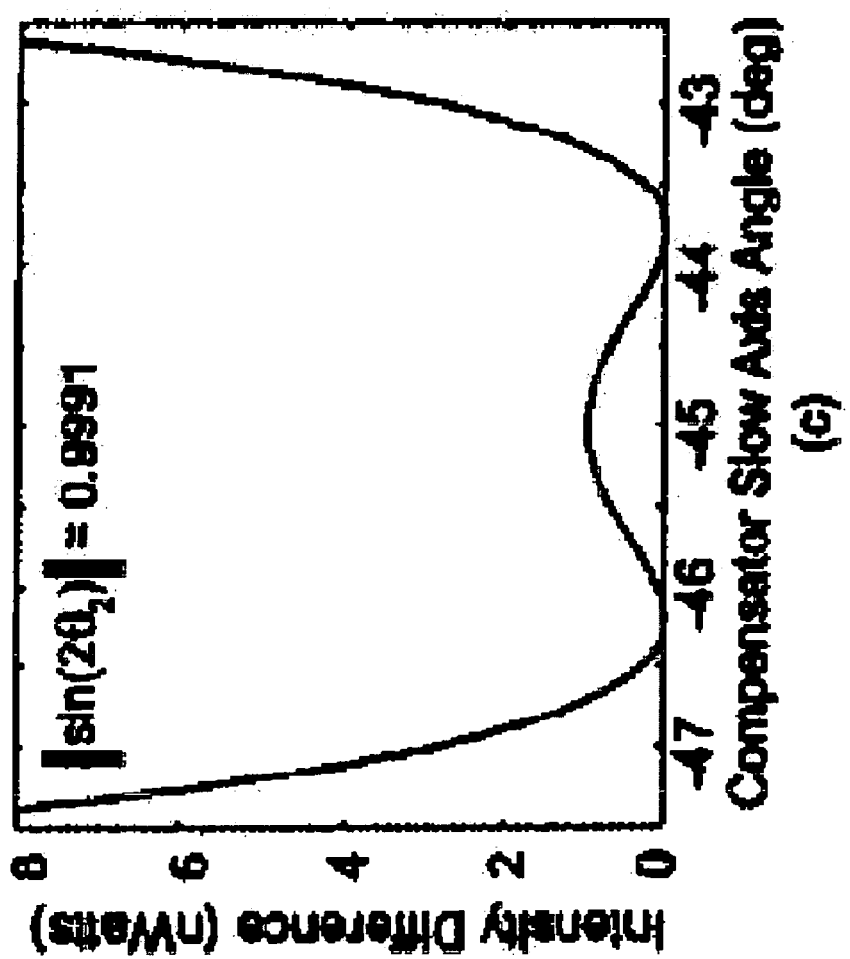
Figure 10D:
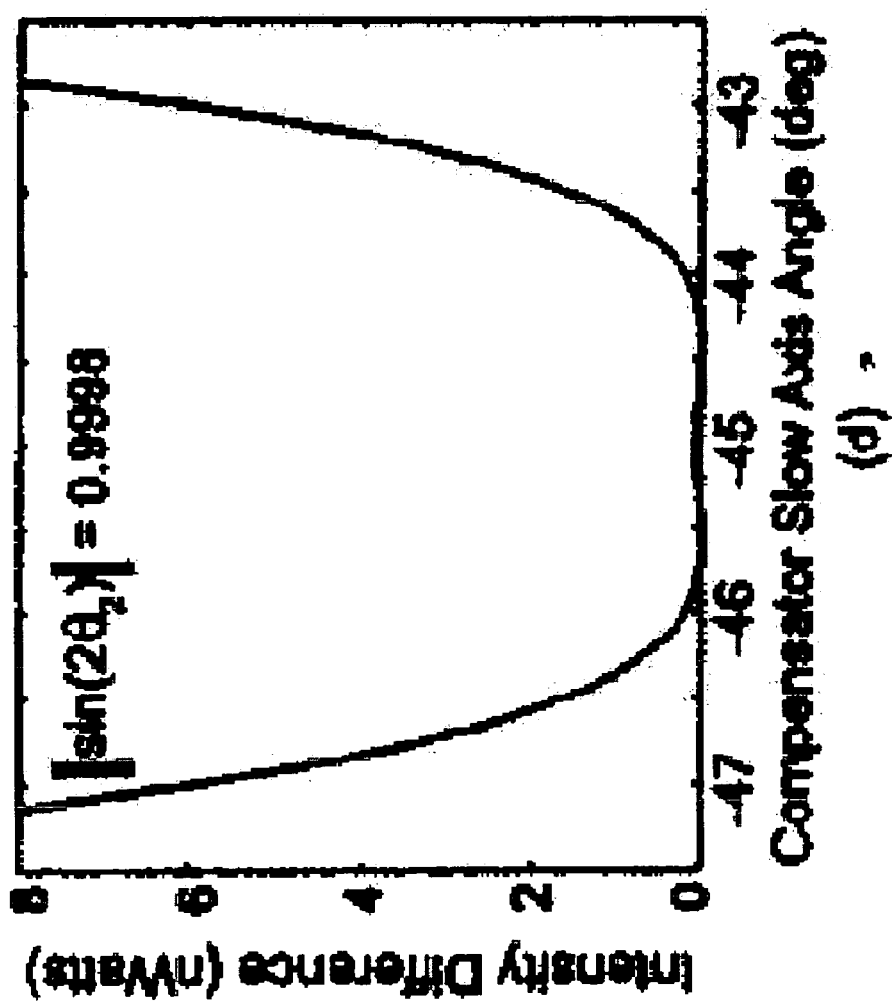
Figure 10E:
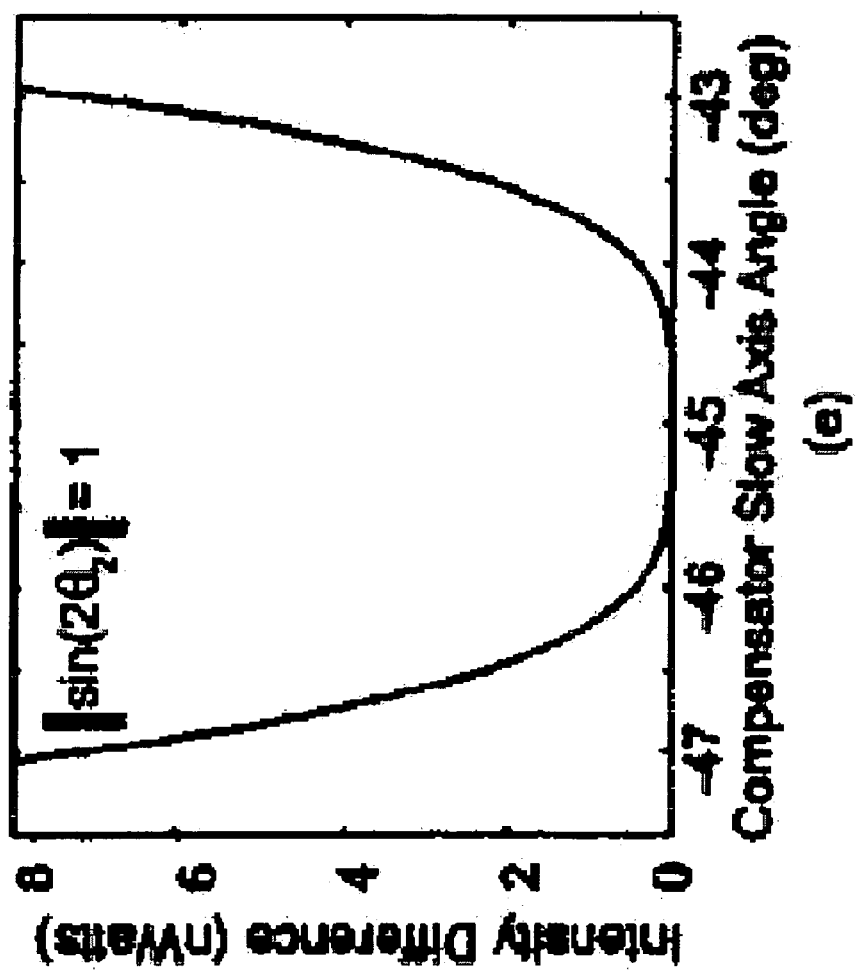

For the retardation of the commercial Brace-Köhler compensator $\phi_1=\lambda/10$, the maximum sample retardation $\phi_{L1}$ is approximately equal to $0.91715\,\phi_2$. The corresponding normalized transmitted intensity is calculated and represented as a function of the compensator orientation $\theta_2$ in FIG. 9. The retardation-based minimum that occurred for the previous value of $\phi_2$ between $\theta_2=-45°$ and $\theta_2=45°$ is not observed and a minimum is now observed for $\theta_2=-45°$ instead of a local non-retardation-based maximum previously. The applicability range of the Brace-Köhler compensator technique can be judged based on its ability to resolve the retardation-based intensity minimum from the closest non-retardation-based intensity maximum that occurs at $\theta_2=\pm 45°$. This is illustrated in FIG. 10 where the transmitted intensity variations relative to the minimum intensity are plotted for different values of $\|\sin 2\theta_2\|$ as it approaches unity. The rotating waveplate retardation $\phi_2$ is equal to $\lambda/10$. The sample retardation is calculated for different values of $\|\sin 2\theta_2\|$ using Eq. (19). The successive values of $\|\sin 2\theta_2\|$ are indicated on each plot. To determine the value of $\|\sin 2\theta_2\|$ for which the retardation-based intensity minimum can usually be resolved from the adjacent intensity maximum, the intensity variations relative to the intensity minimum are plotted as a function of the compensator orientation $\theta_2$. To generate the plots in FIG. 10, it is assumed that the power of the light incident upon the first polarizer is 15 mwatts, which corresponds to the power of the Spectra Physics Model 120S He—Ne laser that is used to test the different retardation measurement techniques. The resolution of the technique can be defined as the smallest intensity variation between a minimum and an adjacent maximum that can be detected by the photodetector. It is assumed that this smallest intensity variation is approximately 1 nwatts. The intensity minimum is resolvable for $\|\sin 2\theta_2\|$ equal to 0.9977, 0.9981 and 0.9991 respectively in FIGS. 10(*a*), 10(*b*), and 10(*c*) as the intensity maximum is larger than the intensity minimum of at least 1 nwatt. However, the minimum is not resolvable for $\|\sin 2\theta_2\|$ equal to 0.9998 in FIG. 10(*d*) as the intensity difference between the maximum and the minimum is much smaller than 1 nwatt. As a result, the condition of applicability of the Brace-Köhler compensator technique defined by the ability to resolve the minimum intensity from the adjacent maximum is mathematically given by $$\|\sin 2\theta_2\| < 0.999 \tag{25}$$

$$\left\| \frac{\sin\phi_1 \sin_2}{2\cos\phi_1(\cos\phi_2 - 1)} \right\| < 0.999 \tag{26}$$

The applicability range of the Brace-Köhler compensator technique is defined and expressed below in terms of sample and compensator retardations. The applicability condition of the technique can be stated simply: for any given pair of sample and compensator retardations, retardation-based minima exists when one or the other plate is rotated. This can be expressed as three mathematical inequalities $$\left\| \frac{\sin\phi_1 \sin\phi_2}{2\cos\phi_1(\cos\phi_2 - 1)} \right\| < 1 \tag{27}$$

$$\sin^2\frac{\phi_1}{2} - \frac{\sin^2\phi_1 \sin^2\phi_2}{16\cos\phi_1 \sin^2\frac{\phi_2}{2}} < \sin^2\left(\frac{\phi_1 + \phi_2}{2}\right) \tag{28}$$

$$\sin^2\frac{\phi_1}{2} - \frac{\sin^2\phi_2 \sin^2\phi_2}{16\cos\phi_1 \sin^2\frac{\phi_2}{2}} < \sin^2\left(\frac{\phi_1 - \phi_2}{2}\right) \tag{29}$$

The first inequality represents the condition for the existence of retardation-based intensity extrema. The two other inequalities are the condition for these retardation-based intensity extrema to be global minima, i.e., the retardation-based intensity extrema are less than the non-retardation-based intensity extrema. If either of these conditions is not satisfied, no minima of intensity satisfying Eq. (19) can be found by either rotating the compensator or rotating the sample and, thus, the Brace-Köhler compensator method can not be applied. The three inequalities (27), (28), and (29) constrain the value of the magnitude of the retardation-based minima. It can be shown that if Eq. (27) is not satisfied, the transmitted intensity calculated using Eq. (22) is negative. Further, it can also be shown that if Eq. (28) is satisfied, Eq. (29) is also satisfied. This means that if the retardation-based extrema is less than either of the non-retardation-based extrema, it is in fact less than both of the non-retardation-based extrema. The condition of existence of the retardation-based minima can be expressed as one unique mathematical inequality by constraining their magnitude to be greater than zero and less than the non-retardation-based intensity extrema $$0 \leq \sin^2\frac{\phi_1}{2} - \frac{\sin^2\phi_1 \sin^2\phi_2}{16\cos\phi_1 \sin^2\frac{\phi_2}{2}} \leq \sin^2\left(\frac{\phi_1 + \phi_2}{2}\right) \tag{30}$$

Figure 11:
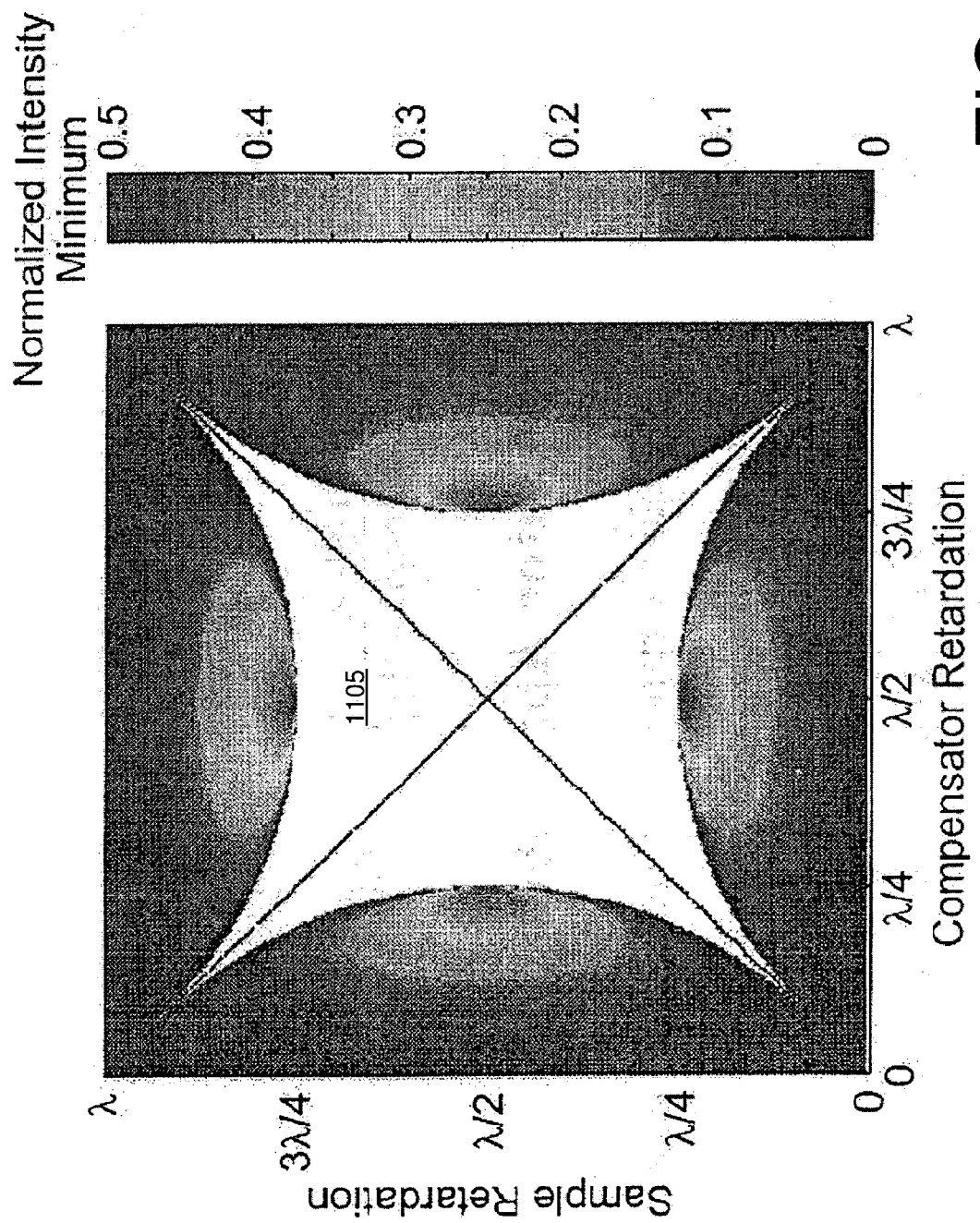
FIG. 11 is a graph illustrating normalized intensity minima for Brace-Köhler compensator applicability range between crossed polarizers.

This condition is represented in FIG. 11 as a function of sample, and compensate retardations ranging from 0 to λ. FIG. 11 represents the normalized transmitted intensity of the retardation-based minima for any given pair of sample and compensator retardations. The white region 1105 represents sample and compensator retardations for which the Brace-Köhler compensator technique is inapplicable to measure the sample retardation.

As was shown earlier in FIG. 6, retardation-based maxima may occur instead of minima. According to Eq. (10), whenever retardation-based maxima occur between crossed polarizers, then non-retardation-based minima occur between parallel polarizers, and conversely. As a result, the Brace-Köhler compensator applicability range may be increased by simply introducing the possibility of making the measurement between parallel polarizers.

The expressions for the retardation-based and non-retardation-based extrema between parallel polarizers are derived using Eqs. (10), (17), (18), and (22)

$$I_{NRB1\|} = \cos^2\left(\frac{\phi_1 + \phi_2}{2}\right) \tag{31}$$

$$I_{NRB2\|} = \cos^2\left(\frac{\phi_1 - \phi_2}{2}\right) \tag{32}$$

$$I_{RB\|} = \cos^2\frac{\phi_1}{2} + \frac{\sin^2\phi_1 \sin^2\phi_2}{16\cos\phi_1 \sin^2\frac{\phi_2}{2}} \tag{33}$$

Figure 12:
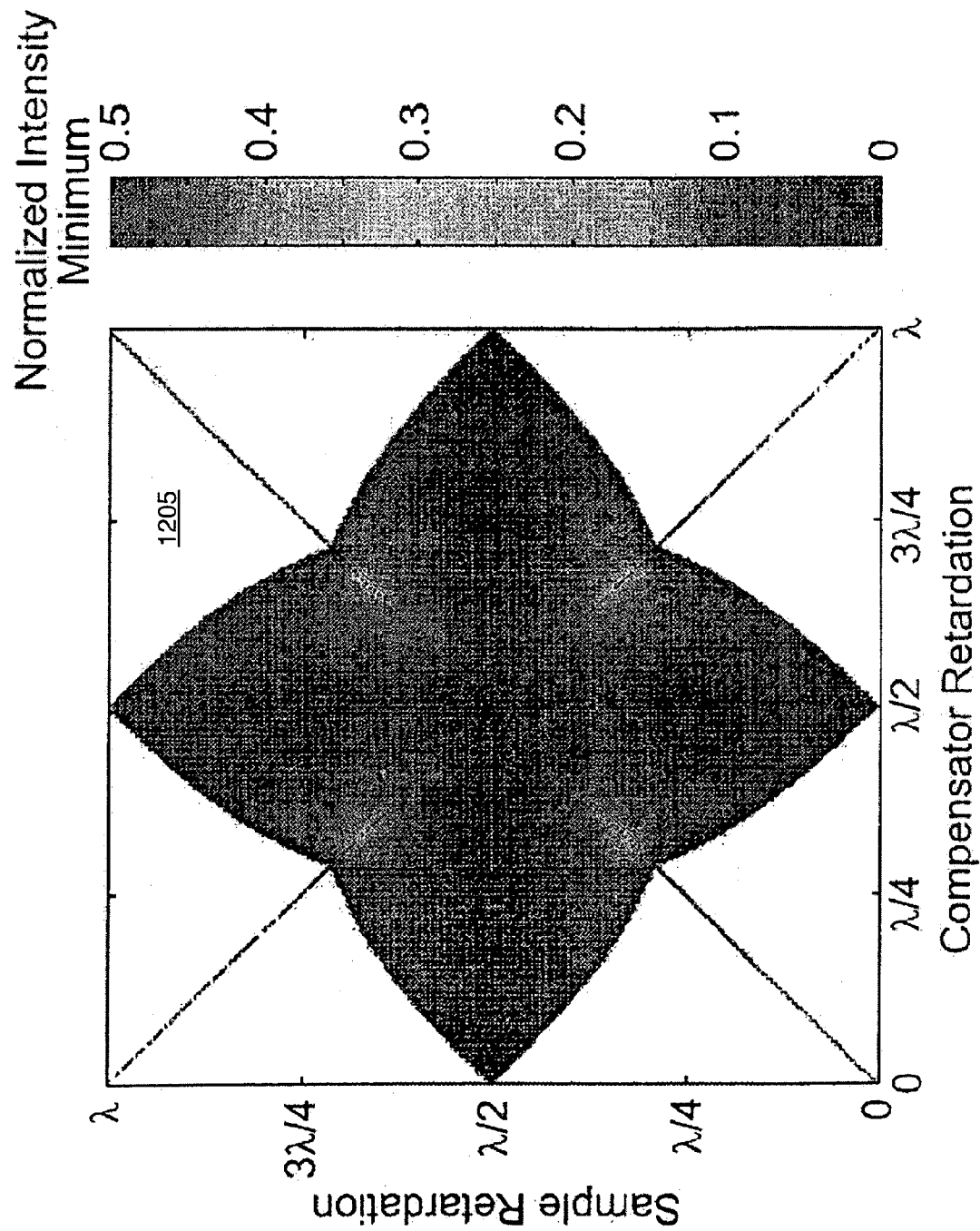
FIG. 12 is a graph illustrating normalized intensity minima for Brace-Köhler compensator applicability range between parallel polarizers.

Similar to the case between crossed polarizers, retardation-based minima between parallel polarizers exist whenever the inequality $$0 \leq \cos^2\frac{\phi_1}{2} + \frac{\sin^2\phi_1 \sin^2\phi_2}{16\cos\phi_1 \sin^2\frac{\phi_2}{2}} \leq \cos^2\left(\frac{\phi_1 + \phi_2}{2}\right) \tag{34}$$

is satisfied. The magnitude of the retardation-based minima between parallel polarizers is represented in FIG. 12 as a function of the sample and compensator retardations. The white region 1205 represents sample and compensator retardations for which the Brace-Köhler compensator technique is inapplicable between parallel polarizers.

Figure 13A:
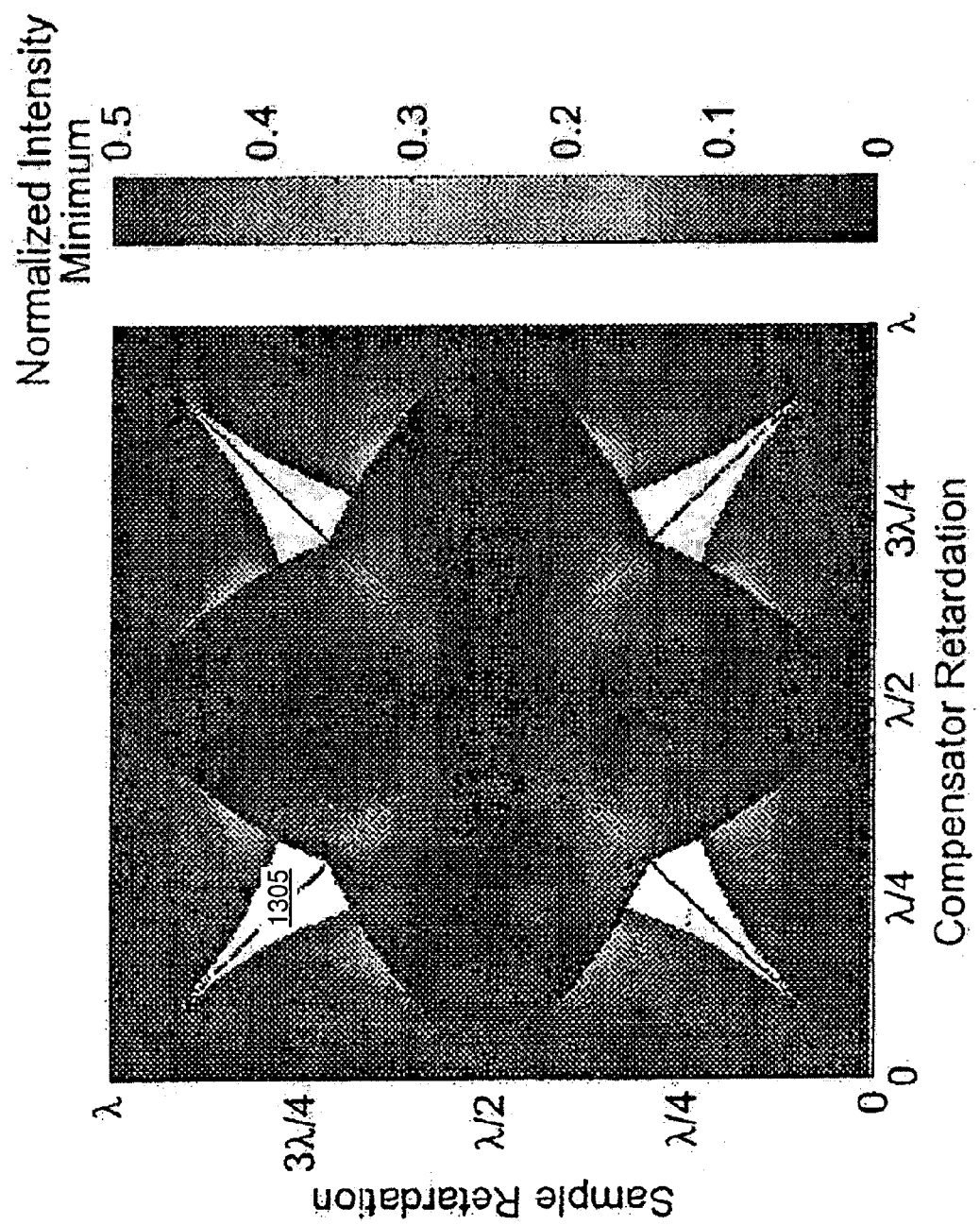
FIGS. 13A and 13B are graphs illustrating the superposition of the graphs of FIGS. 11 and 12.
Figure 13B:
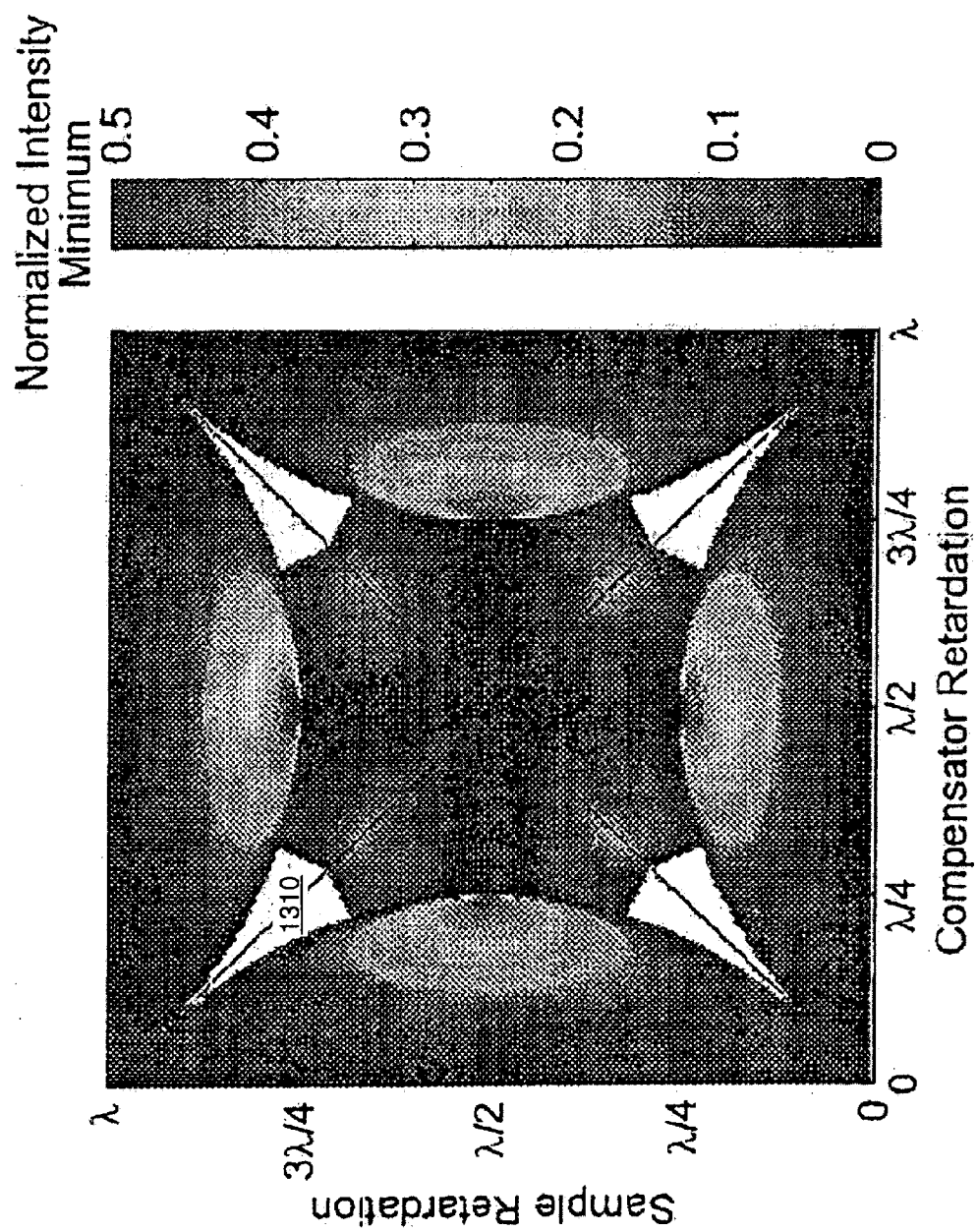

By superimposing FIGS. 11 and 12, sample and compensator retardations for which retardation-based minima can be observed and, therefore, the Brace-Köhler compensator technique applied are determined. This is shown in FIGS. 13(*a*) and 13(*b*). In FIG. 13(*a*), the retardation-based minima magnitudes between parallel polarizers are superimposed onto the retardation-based minima magnitudes between crossed polarizers whereas in FIG. 13(*b*), the retardation-based minima magnitudes between crossed polarizers are superimposed onto the retardation-based minima magnitudes between parallel polarizers. Sample and compensator retardations for which retardation-based minima exist between crossed polarizers and parallel polarizers do not produce equal intensity. Although it is possible to observe retardation-based minima in both cases, the rotating waveplate is different and this produces a different intensity. The white region in FIGS. 13(*a*) and 13(*b*) correspond to sample and compensator retardations producing no retardation-based extrema regardless of which waveplate is rotated and regardless of the polarizers being crossed or parallel.

The Brace-Köhler compensator technique has numerous shortcomings that limit its applicability range and its accuracy. It typically only minimizes the transmitted electric field component along the analyzer transmission direction, as shown in FIG. 4. Overall, it minimizes the phase-shift introduced between the input electric field component along the first polarizer transmission direction and output electric field component along the analyzer transmission direction. It is therefore not a rigorous compensation method and does not always produce extinction as is the case for example with the Senarmont compensator technique.

Two extreme configurations may be considered when one waveplate is rotated and the other remains fixed: 1) the slow axis of the rotating waveplate may be parallel to the slow axis of the fixed waveplate, in which case both retardations are added; and 2) the slow axis of the rotating waveplate may be parallel to the fast axis of the fixed waveplate, in which case both retardations are subtracted. In between these two extremes, there exists a relative orientation of the waveplates resulting in a total retardation equal to 0 or λ producing a linearly polarized output. The retardation between the components along the slow and fast axes of the second waveplate in FIG. 1 is now considered as opposed to that between the components along the polarizers transmission direction. If this linearly polarized output exists, it is not parallel to the polarizers transmission directions and extinction is obtained if the analyzer is rotated so as to be perpendicular to the linear polarization direction of the electric field exiting the second waveplate. This is the basis for the development of a Two-Waveplate-Compensator (TWC) technique. The analysis of the relative orientation of both waveplates producing linearly polarized output, and the development of an experimental procedure to determine this orientation by rotating successively one waveplate and the analyzer, is provided below.

An analytical expression of the rotating waveplate angle for obtaining a linearly polarized output is desired. This can be done using Jones calculus as it was done in previously for the Brace-Kohler compensator system. FIG. 2 can also be used to illustrate the various systems of axes in which the electric field is expressed. The Jones vector expressed in the system of axes associated with the second waveplate and characteristic of the electric field transmitted through the first fixed waveplate of retardation $\phi_1$ and the second rotating waveplate of retardation $\phi_2$ (FIG. 2) is given by $$\vec{\varepsilon_2} = T(\phi_2)R(\theta_2)\begin{pmatrix} a \\ be^{j\frac{\pi}{2}} \end{pmatrix} \quad (35)$$

where $T(\phi_2)$ is the transmission matrix of retardation, $\phi_2$, $R(\theta_2)$ is the rotation matrix of angle $\theta_{2r}$, and a and b are the components magnitudes of the Jones vector characteristic of the electric field exiting the first waveplate expressed in the system of axes of the crossed polarizers. These last Jones vector components can be calculated as follows $$\begin{pmatrix} a \\ be^{j\frac{\pi}{2}} \end{pmatrix} = R(-\theta_1)T(\phi_1)R(\theta_1)\begin{pmatrix} 1 \\ 0 \end{pmatrix} = \quad (36)$$

$$\begin{pmatrix} \cos\theta_1 & -\sin\theta_1 \\ \sin\theta_1 & \cos\theta_1 \end{pmatrix}\begin{pmatrix} 1 & 0 \\ 0 & e^{j\phi_1} \end{pmatrix}\begin{pmatrix} \cos\theta_1 & \sin\theta_1 \\ -\sin\theta_1 & \cos\theta_1 \end{pmatrix}\begin{pmatrix} 1 \\ 0 \end{pmatrix}$$

The fixed waveplate slow axis being at 45 degrees from the polarizer transmission direction, the components a and b can be computed as a function of $\phi_x$ by substituting $$\theta_1 = \frac{\pi}{4}$$

in Eq. (36). It can be shown that the major and minor axes, respectively a and b, of the ellipse traced by the electric field exiting the first waveplate are given by $$a = \cos\phi_1 \quad (37)$$

$$b = -\sin\phi_1 \quad (38)$$

Substituting Eq. (38) in Eq. (35) and carrying out the matrix multiplication, $\vec{\varepsilon}_2$ can be written in the form $$\vec{\varepsilon_2} = \begin{pmatrix} a_1 e^{j\delta_1} \\ a_2 e^{j(\delta_2+\phi_2)} \end{pmatrix} \quad (39)$$

with $$a = \cos\phi_1 \quad (40)$$

$$b = -\sin\phi_1 \quad (41)$$

$$a_1 = (a^2\cos^2\theta_2 + b^2\sin^2\theta_2)^{\frac{1}{2}} \quad (42)$$

$$a_2 = (a^2\sin^2\theta_2 + b^2\cos^2\theta_2)^{\frac{1}{2}} \quad (43)$$

$$\delta_1 = \arctan\left(\frac{b\sin\theta_2}{a\cos\theta_2}\right) \quad (44)$$

$$\delta_2 = \arctan\left(\frac{b\cos\theta_2}{-a\sin\theta_2}\right) \quad (45)$$

The condition for the electric field to be linearly polarized after passing through the two waveplates is given by, $$\delta_2 + \phi_2 = \delta_1 + k\pi \quad (46),$$

with k being an integer value.

Substituting the expressions of $\delta_1, \delta_2$ in Eq. (46), $$\arctan\left[\tan\left(\frac{\phi_1}{2}\right)\cot(\theta_2)\right] + \phi_2 = -\arctan\left[\tan\left(\frac{\phi_1}{2}\right)\tan(\theta_2)\right] \quad (47)$$

Using the trigonometric identity $$\tan(r+t) = \frac{\tan(r) + \tan(t)}{1 - \tan(r)\tan(t)}$$

and simplifying gives $$\cot(\theta_2) + \tan(\theta_2) = \frac{\tan(\phi_2)}{\tan\left(\frac{\phi_1}{2}\right)}\left(\tan^2\left(\frac{\phi_1}{2}\right) - 1\right) \quad (48)$$

Using trigonometric identities leads to the condition for linearly polarized light as $$\sin 2\theta_2 = -\frac{\tan \phi_1}{\tan \phi_2} \quad (49)$$

Figure 14A:
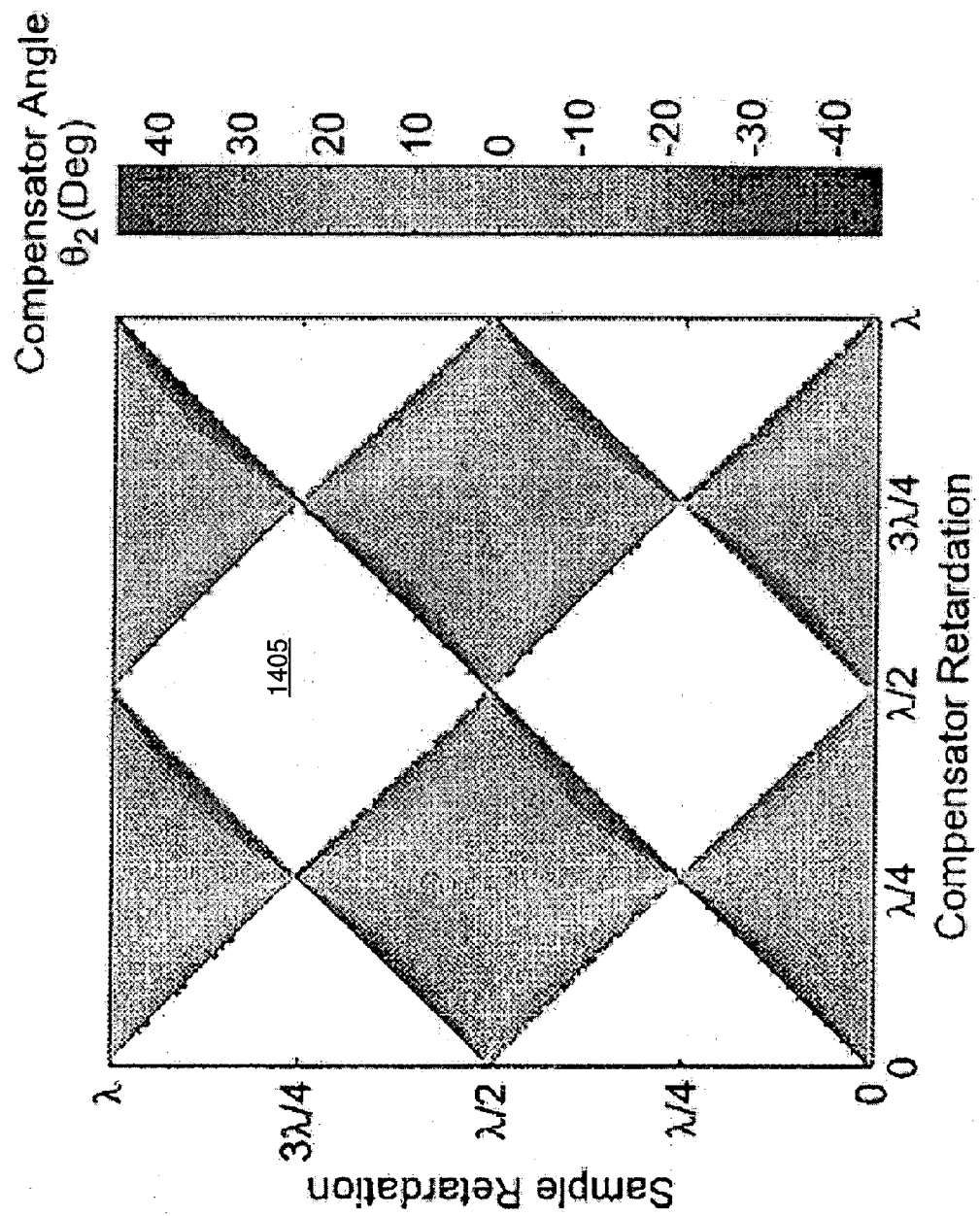
FIG. 14 is a graph illustrating the magnitude of $\theta_2$ producing extinction in a two-waveplate compensator (TWC) technique for when the compensator is rotated.
FIG. 14B is a graph illustrating the magnitude of $\theta_2$ producing extinction in a TWC technique for when the sample is rotated.
Figure 14B:
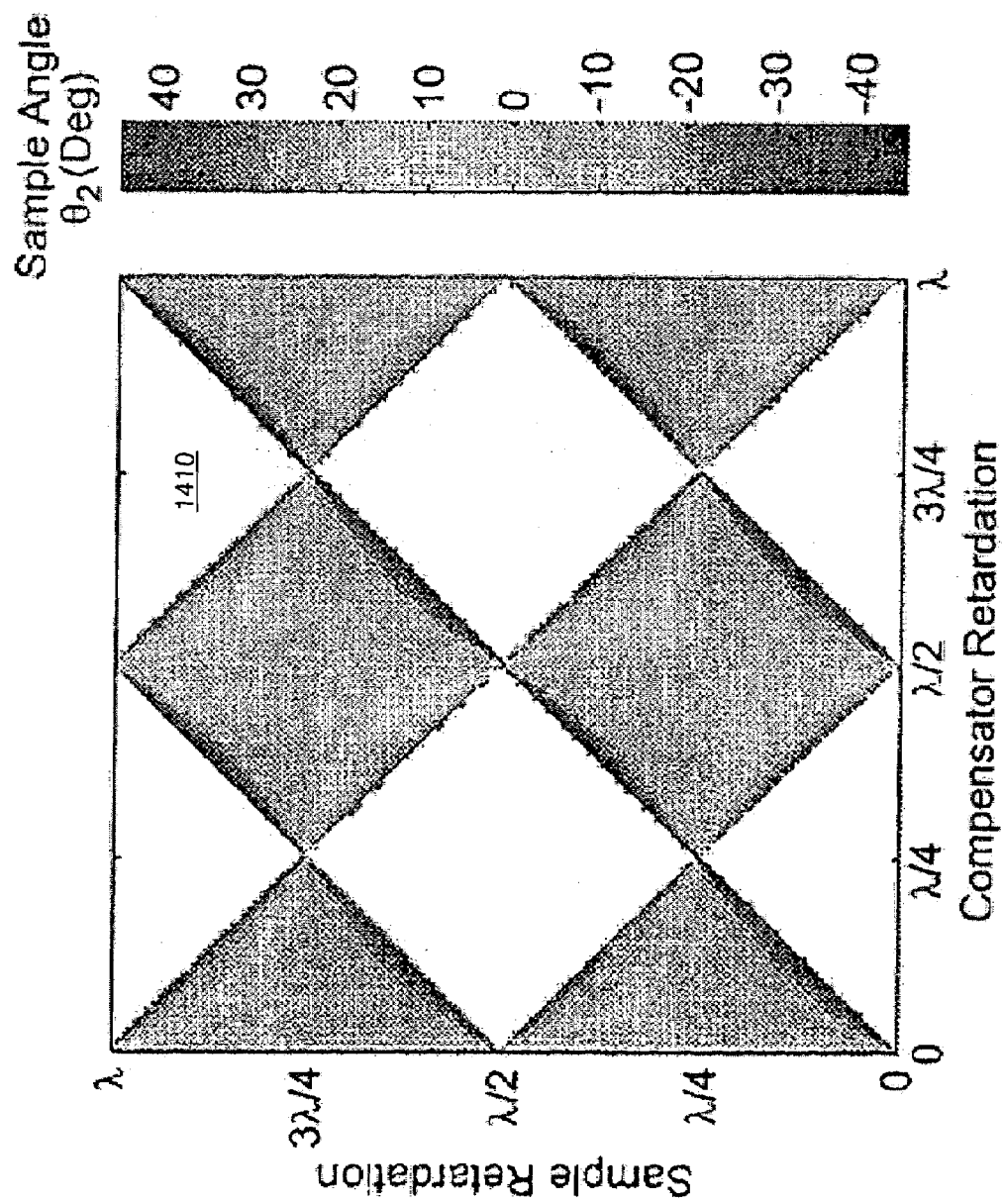

In Eq. (49), the angle $\theta_2$ is the angle of the rotating waveplate producing linearly polarized light. Similar to the Brace-Kohler technique, the angle $\theta_2$ depends upon the retardations $\phi_1$ and $\phi_2$ The condition of existence of the angle $\theta_2$ is given by $$\left\| -\frac{\tan \phi_1}{\tan \phi_2} \right\| \leq 1 \quad (50)$$

with $\phi_1$ the retardation produced by the first waveplate at 45 degrees from extinction between crossed polarizers, $\phi_2$ the retardation of the rotating waveplate whose initial orientation is at extinction between crossed polarizers, and $\theta_2$ the rotating waveplate angle producing linearly polarized light. For any given sample and compensator retardations, Eq. (50) allows one to determine which waveplate is to be rotated to obtain linearly polarized light. Contrary to the Brace-Köhler compensator technique, whose retardation-based minima does not exist for all sample and compensator retardations (FIG. 13), the TWC technique is produces linearly polarized output provided that Eq. (50) is satisfied. The applicability range of the TWC technique can be represented using Eq. (50) as a function of the sample and compensator retardations. FIG. 14 represents the magnitude of the angle $\theta_2$ in degrees for different sample and compensator retardations. For any given sample and compensator retardations, the angle $\theta_2$ is calculated using Eq. (49). Depending on the retardation values, either the compensator is rotated to obtain linearly polarized light, which is represented in FIG. 14(a), or the sample is rotated, which is represented in FIG. 14(b). The fixed and rotating waveplates are chosen according to Eq. (50). For any given pair of sample and compensator retardations, a linearly polarized output can be obtained, provided that the fixed and rotating waveplate roles are assigned so that Eq. (50) is satisfied. If by rotating the compensator (or the sample) Eq. (50) is not satisfied, i.e., $\|\sin 2\theta_2\| > 1$, the sample (or the compensator) then satisfies Eq. (50), since inverting the roles of the two waveplates results in inverting the ratio $$\frac{\tan \phi_1}{\tan \phi_2}.$$

FIG. 14 allows one to determine which of the sample or compensator waveplate is rotated to obtain linearly polarized light. However, with no prior knowledge of the sample retardation, it is important to develop an experimental procedure allowing the determination of the configuration that produces a linearly polarized output. The polarization state of the output light is studied for given pairs of sample and compensator retardations for the two different configurations for which, on one hand, the compensator is rotated, and on the other hand, the sample is rotated. Depending on the retardation values of the sample and the compensator, one of these configurations is such that Eq. (50) is satisfied, and linearly polarized light is produced whereas the other configuration is such that Eq. (50) is not satisfied, and linearly polarized light is not produced.

Figure 15A:
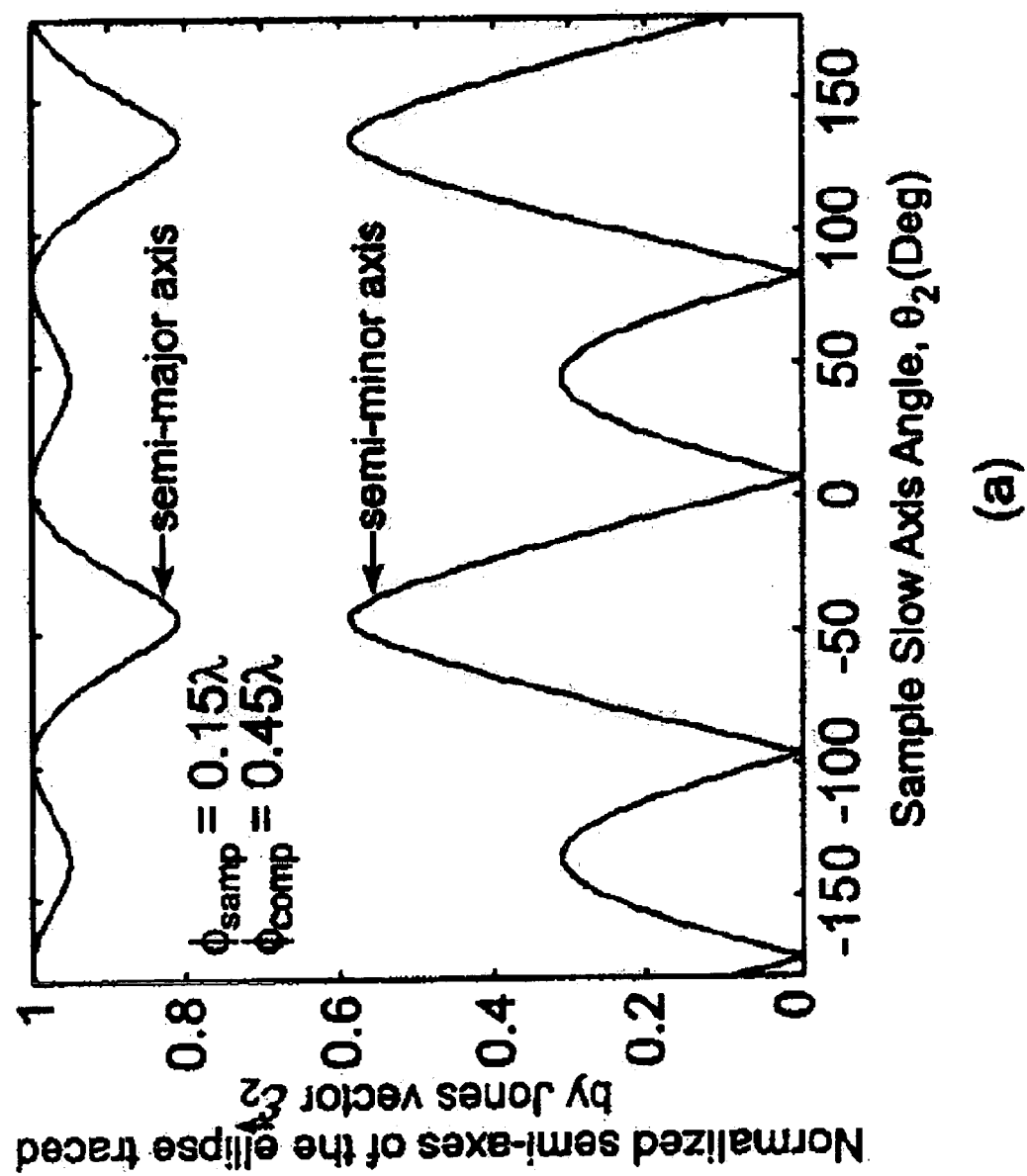
FIGS. 15A and 15B are graphs illustrating the semi-minor axis, the semi-major axis, and the ellipticity of the transmitted light polarization ellipse as a function of a sample slow axis angle for particular experimental setup.
Figure 15B:
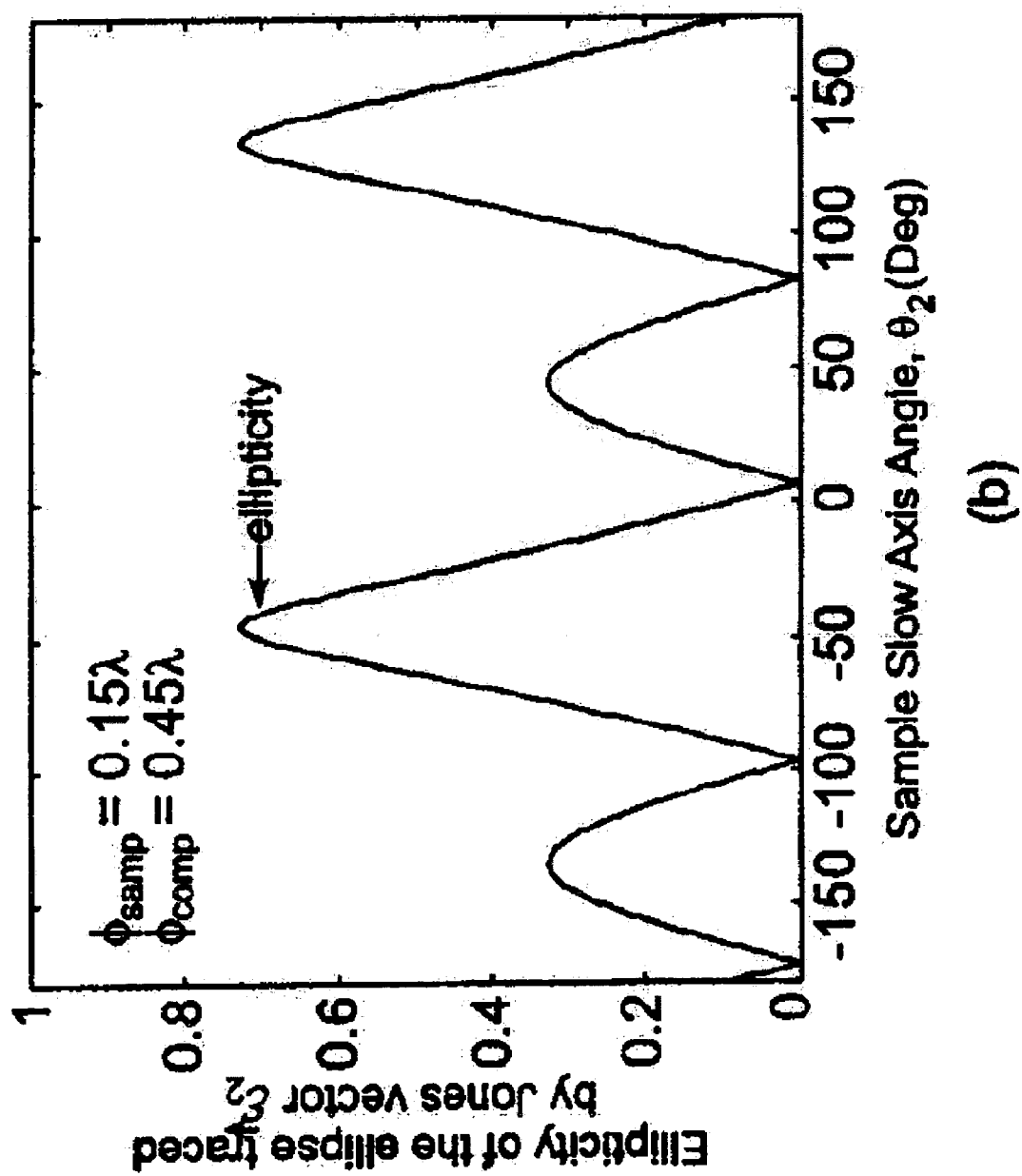
Figure 16A:
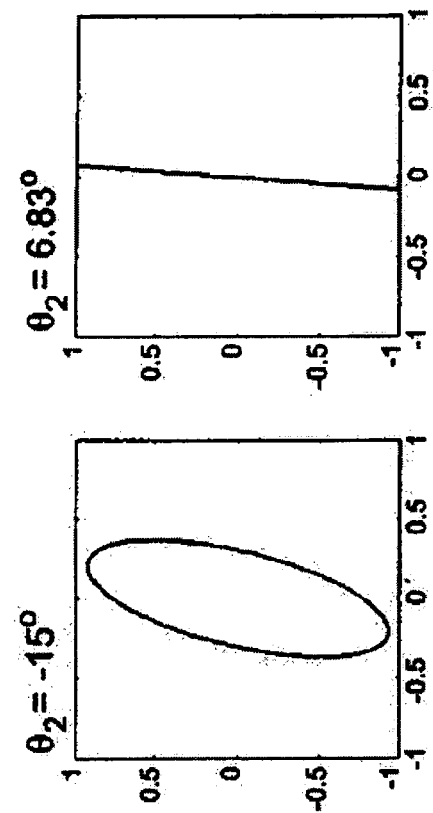
FIGS. 16A through 16G are graphs illustrating output light polarization states for various slow axes angles for the experimental setup of FIGS. 15A and 15B.
Figure 16B:
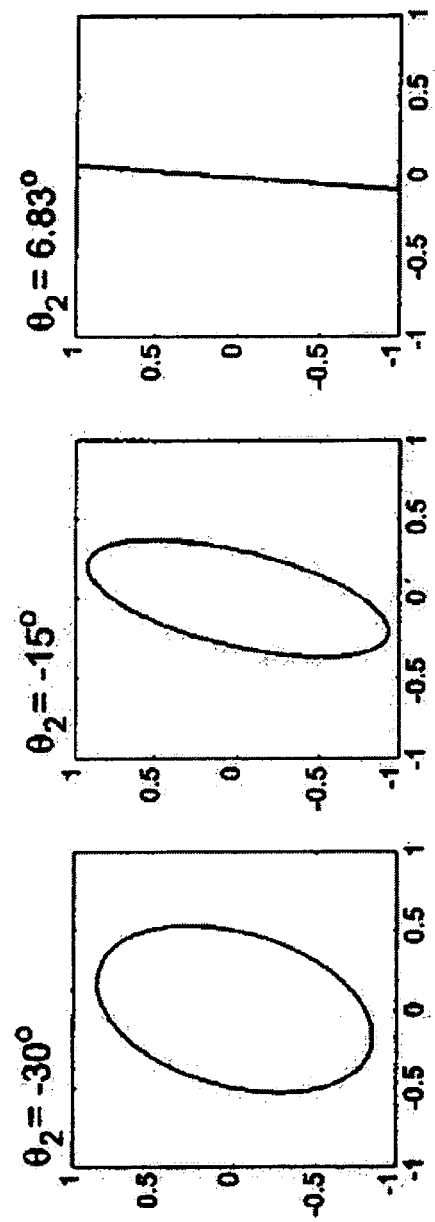
Figure 16C:
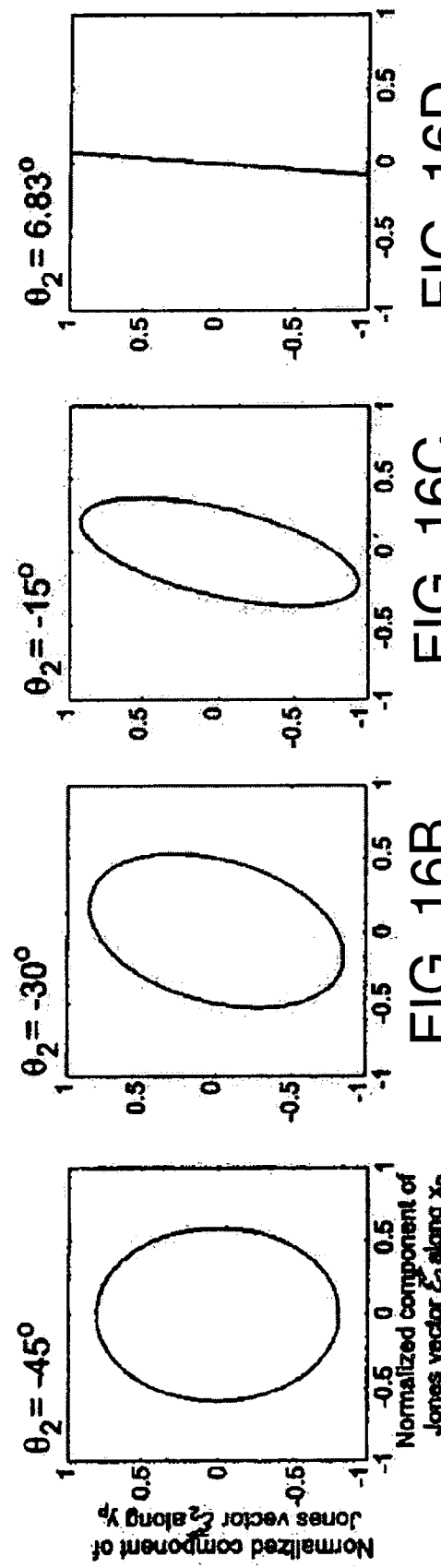
Figure 16D:
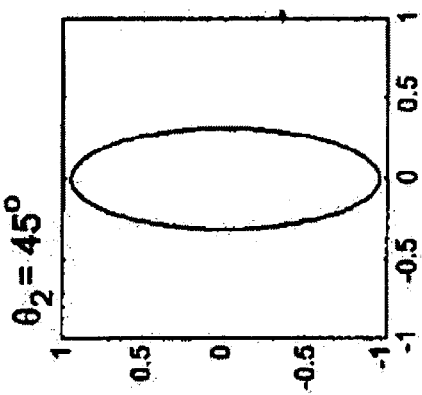
Figure 16E:
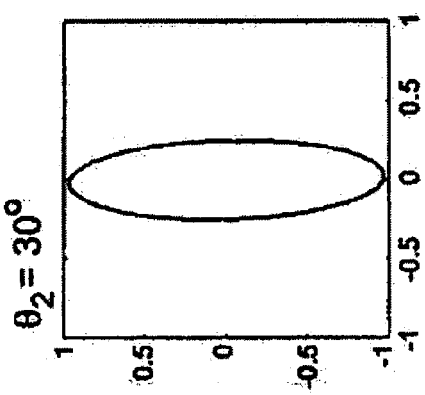
Figure 16F:
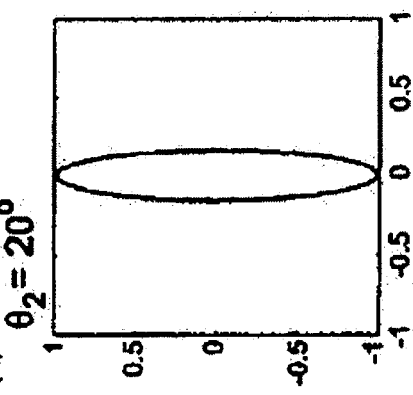
Figure 16G:
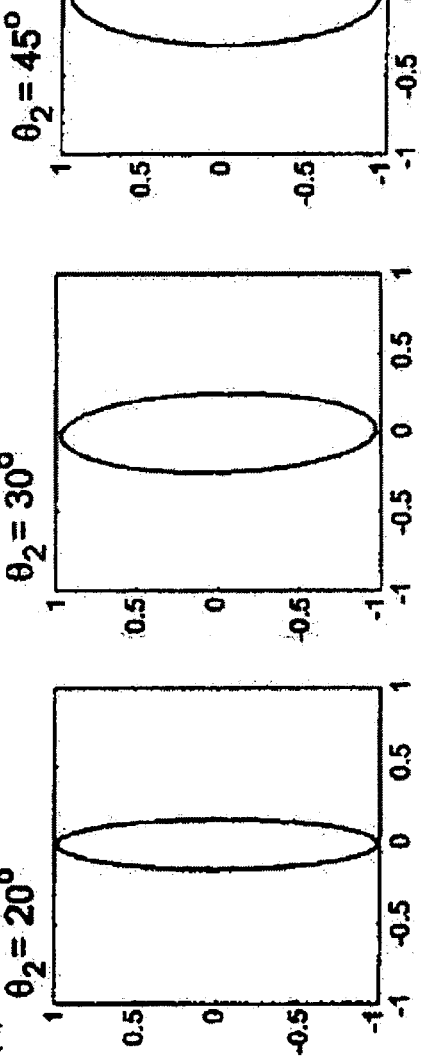

Results of a detailed study of the output light polarization are shown in FIGS. 15, 16, 17, and 18 for a sample of retardation equal to 0.15λ and a compensator of retardation equal to 0.45λ. The x-axis of the system in which the polarization states are plotted in FIGS. 16 and 18 correspond to the first polarizer transmission direction. In the TWC technique, this polarizer remains fixed. For the retardations used in this example, a linearly polarized output is produced when the sample of retardation 0.15λ is the rotating waveplate. By substituting into Eq. (49) the retardation values of the sample and compensator, the sample orientation that produces a linearly polarized output is calculated and is equal to 6.83°. The lengths of the semi-axes and the ellipticity of the output light polarization ellipse as a function of the sample orientation are plotted in FIG. 15. The linearly polarized output is produced when the semi-minor axis of the polarization ellipse is equal to zero. Over a full 360° rotation of the sample, this occurs four times and each is mathematically equivalent. It has been shown in an earlier section that $\sin 2\theta_2 = X$ has four angle solutions. Since these angles are mathematically equivalent, only one is needed for the measurement. In FIG. 16, the output light polarization is represented when the sample of retardation 0.15λ is rotated from −45° to 45°. As calculated, the linearly polarized output is produced for $\theta_2$ equal to 6.83° which is also seen in FIG. 15. When rotating the linearly polarizing waveplate from −45° to +45° the semi-minor axis of the output ellipse of polarization goes through zero. By incrementally rotating the analyzer so that its transmission direction is parallel to the semi-minor axis of the polarization ellipse as the linearly polarizing waveplate is rotated, the intensity transmitted goes through extinction when the semi-minor axis goes throughzero.

Figure 17A:
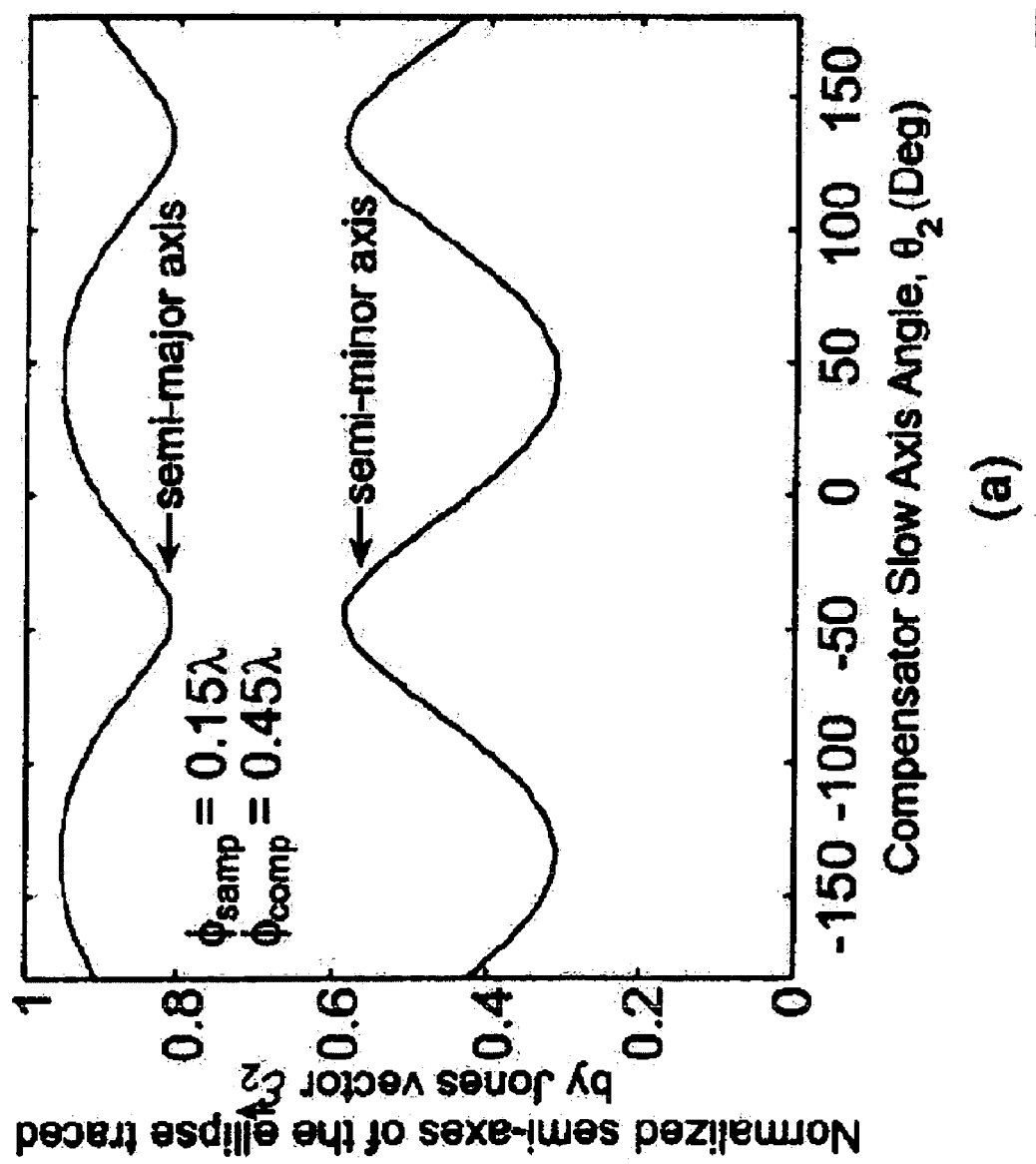
FIGS. 17A and 17B are graphs illustrating the semi-minor axis, the semi-major axis, and the ellipticity of the transmitted light polarization ellipse as a function of a compensator slow axis angle for particular experimental setup.
Figure 17B:
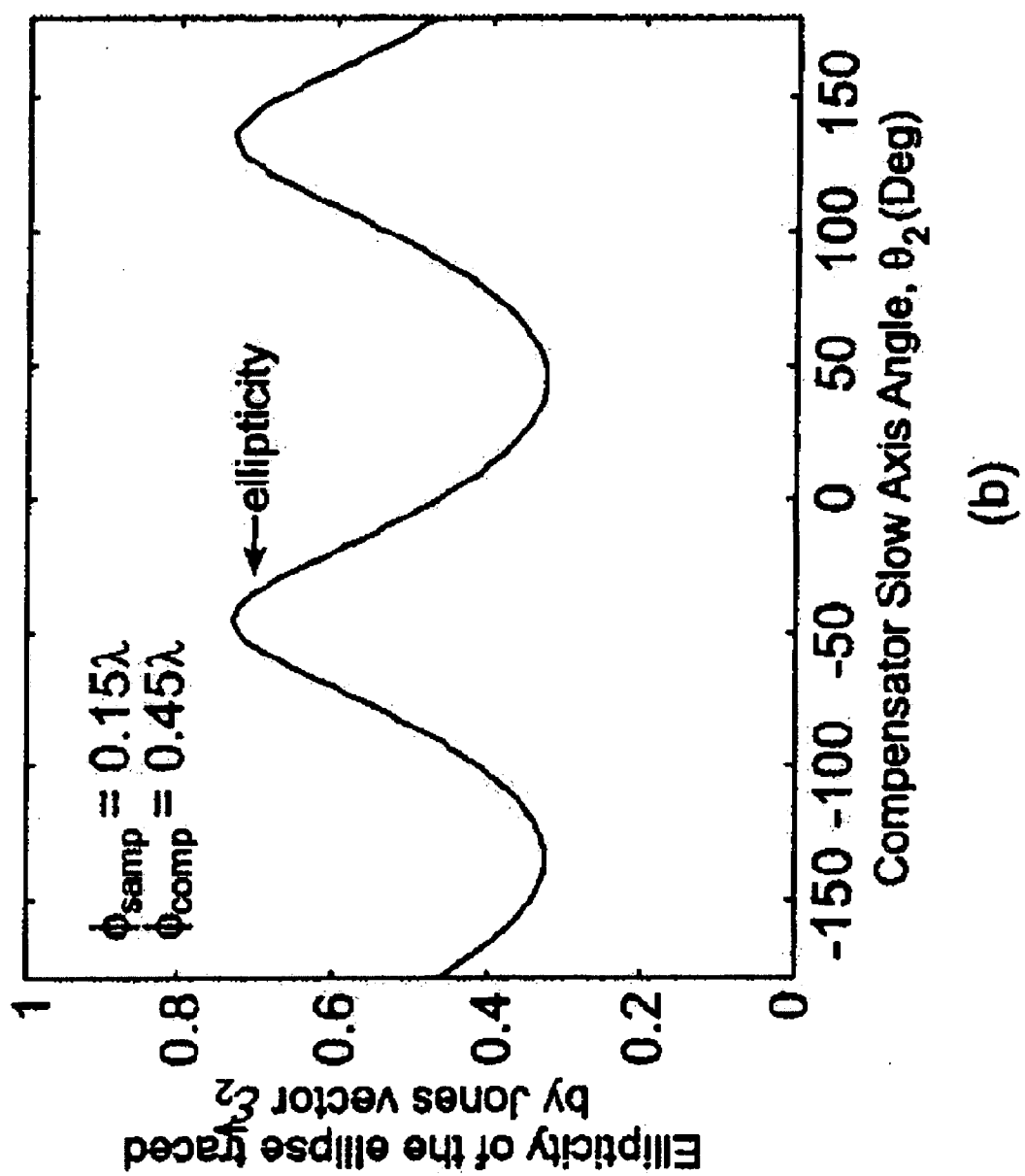
Figure 18A:
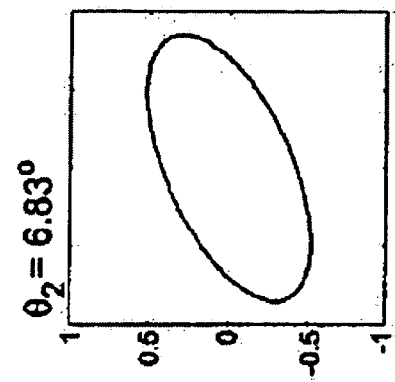
FIGS. 18A through 18G are graphs illustrating output light polarization states for various slow axes angles for the experimental setup of FIGS. 17A and 17B.
Figure 18B:
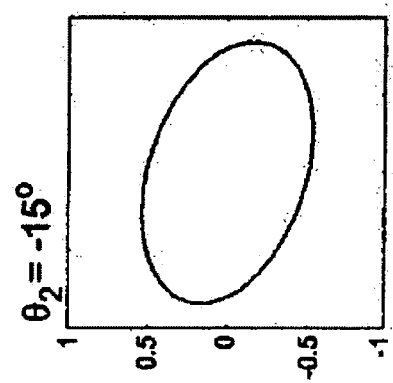
Figure 18C:
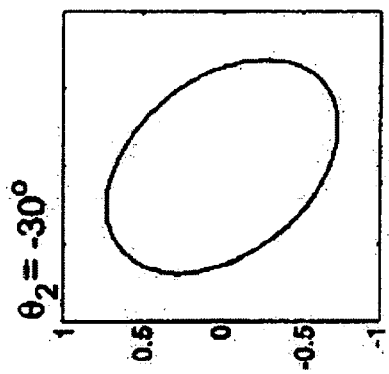
Figure 18D:
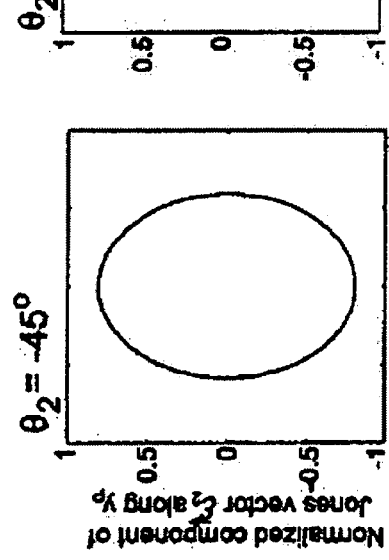
Figure 18E:
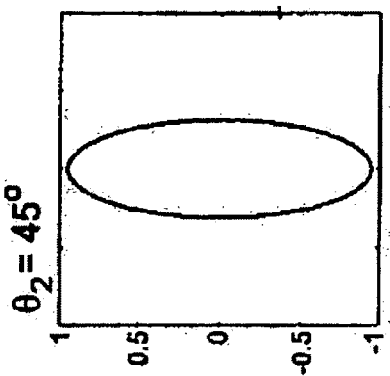
Figure 18F:
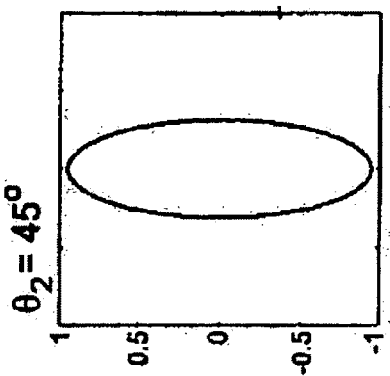
Figure 18G:
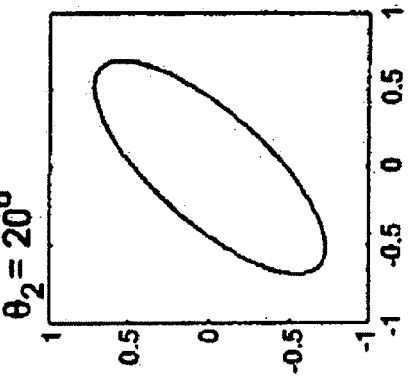

In contrast, FIGS. 17 and 18 represent the semi-axes, ellipticity, and polarization states as the compensator is rotated. In this configuration the non-linearly polarizing waveplate is rotated and no linearly polarized output is produced between −45° and +45°. The semi-minor axis of the output polarization ellipse decreases monotonically as the compensator is rotated. The actual semi-axes lengths, minor semi-axis orientation, ellipticity of the polarization states represented in FIGS. 16 and 18 are summarized in Tables 1 and 2.

TABLE 1

Semi-axes lengths, ellipticity, semi-minor axis angle of the output light polarization ellipse as a function of the sample slow axis angle $\theta_2$, $\phi_{samp} = 0.15\lambda$, $\phi_{comp} = 0.45\lambda$.

| $\theta_2$ (Deg) | Semi-Minor Axis (Normalized) | Semi-Minor Axis Angle (Deg) | Semi-Major Axis (Normalize | Ellipticity (No Dimensions) |
|---|---|---|---|---|
| −45 | 0.5878 | 0 | 0.8090 | 0.7265 |
| −30 | 0.4847 | −16.89 | 0.8746 | 0.5542 |
| −15 | 0.2965 | −13.97 | 0.9550 | 03105 |
| 6.83 | 0 | −4.40 | 1.0000 | 0 |
| 20 | 0.1585 | 0.05 | 0.9874 | 01605 |

TABLE 1-continued

Semi-axes lengths, ellipticity, semi-minor axis angle of the output light polarization ellipse as a function of the sample slow axis angle
$\theta_2, \phi_{samp} = 0.15\lambda, \phi_{comp} = 0.45\lambda.$

| $\theta_2$ (Deg) | Semi-Minor Axis (Normalized) | Semi-Minor Axis Angle (Deg) | Semi-Major Axis (Normalize) | Ellipticity (No Dimensions) |
|---|---|---|---|---|
| 30 | 0.2503 | 1.47 | 0.9682 | 0.2585 |
| 45 | 0.3090 | 0 | 09510 | 03249 |

TABLE 2

Semi-axes lengths, ellipticity, semi-minor axis angle of the output light polarization ellipse as a function of the compensator slow axis angle
$\theta_2, \phi_{samp} = 0.15\lambda, \phi_{comp} = 0.45\lambda.$

| $\theta_2$ (Deg) | Semi-Minor Axis (Normalized) | Semi-Minor Axis Angle (Deg) | Semi-Major Axis (Normalized) | Ellipticity (No Dimensions) |
|---|---|---|---|---|
| −45 | 0.5878 | 0 | 0.8090 | 0.7265 |
| −30 | 0.5587 | 40.73 | 0.8294 | 0.6736 |
| −15 | 0.4950 | 73.34 | 0.8687 | 0.5697 |
| 6.83 | 0.3955 | 113.71 | 0.9184 | 0.4306 |
| 20 | 0.3481 | 136.77 | 0.9374 | 0.3713 |
| 30 | 0.3234 | 154.09 | 0.9462 | 0.3418 |
| 45 | 0.3090 | 180 | 0.9510 | 0.3249 |

The observation of the output polarization states as the linearly-polarizing or the non-linearly-polarizing waveplate is rotated allows one to develop the experimental procedure to determine which of the sample or the compensator should be rotated to use the TWC technique. One example embodiment, among others, of the TWC technique is illustrated in FIGS. 19A through 20.

Figure 19A:
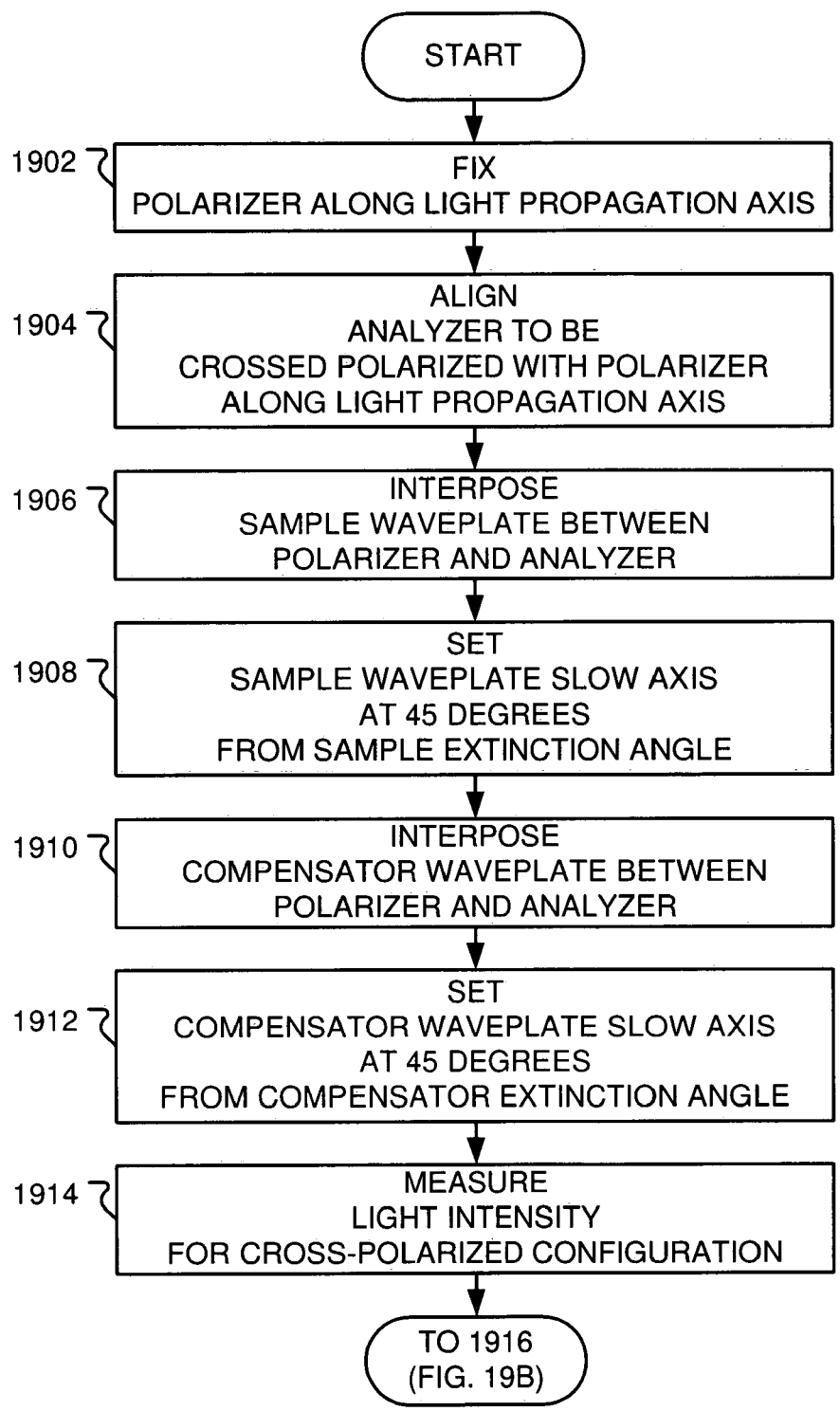
FIGS. 19A through 19D are flowcharts illustrating one embodiment, among others, of a method for measuring birefringence.
Figure 20:
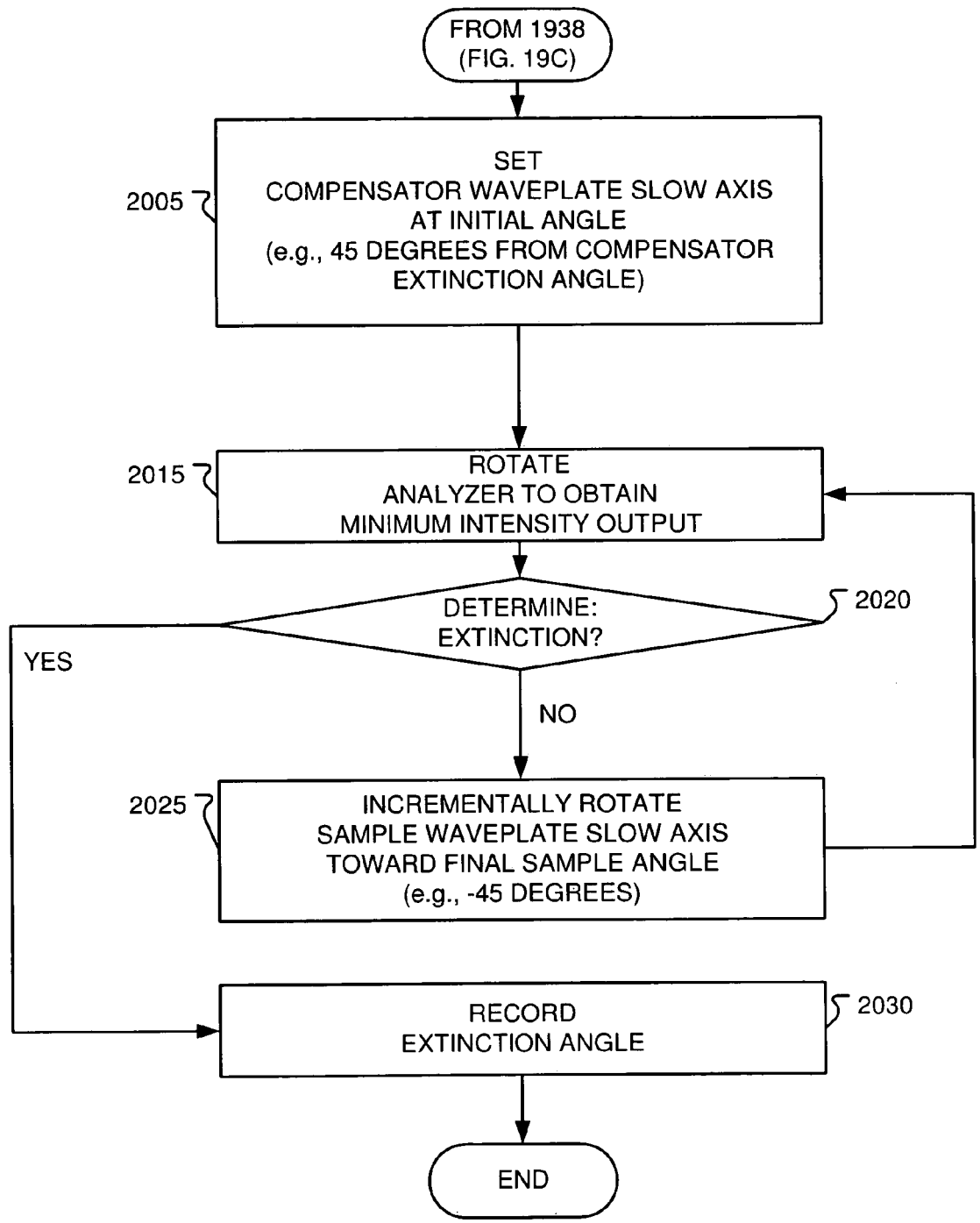
FIG. 20 is a flowchart illustrating method steps associated with an embodiment of the method for measuring birefringence.

As shown in FIG. 19A, a polarizer is fixed (1902) along the light-propagation axis. Along that light-propagation axis, a second polarizer (referred to herein as an analyzer) is oriented (1904) in crossed polarizers configuration with the fixed polarizer. A first waveplate, referred to herein as a sample waveplate, is interposed (1906) between the polarizer and the analyzer. That sample waveplate is set (1908) such that the slow axis of the sample waveplate is at 45 degrees from its extinction angle. The extinction angle can be provided in advance or, alternatively, determined experimentally. The experimental determination of the extinction angle is described in greater detail with reference to FIGS. 27A and 27B. It should, however, be appreciated that, for other embodiments, the experiment can be performed at angles other than 45 degrees, such as for the phase-stepping approach described below.

Upon setting (1908) the sample waveplate slow axis angle at 45 degrees (or other arbitrary angle for other experiments) from extinction, a second waveplate, referred to herein as a compensator waveplate, is interposed (1910) between the polarizer and the analyzer. At this point, for some embodiments, the configuration can appear similar to that shown in FIG. 1. The compensator waveplate slow axis is then set (1912) at 45 degrees from the sample extinction angle. Again, the compensator extinction angle can be experimentally determined, or, alternatively, provided a priori. Also, the compensator initial angle need not be set to 45 degrees for other configurations, such as those described below for the phase-stepping approach. Given this configuration, the light intensity is measured (1914). As noted above, the polarizer and the analyzer are in crossed polarizers configuration.

Figure 19B:
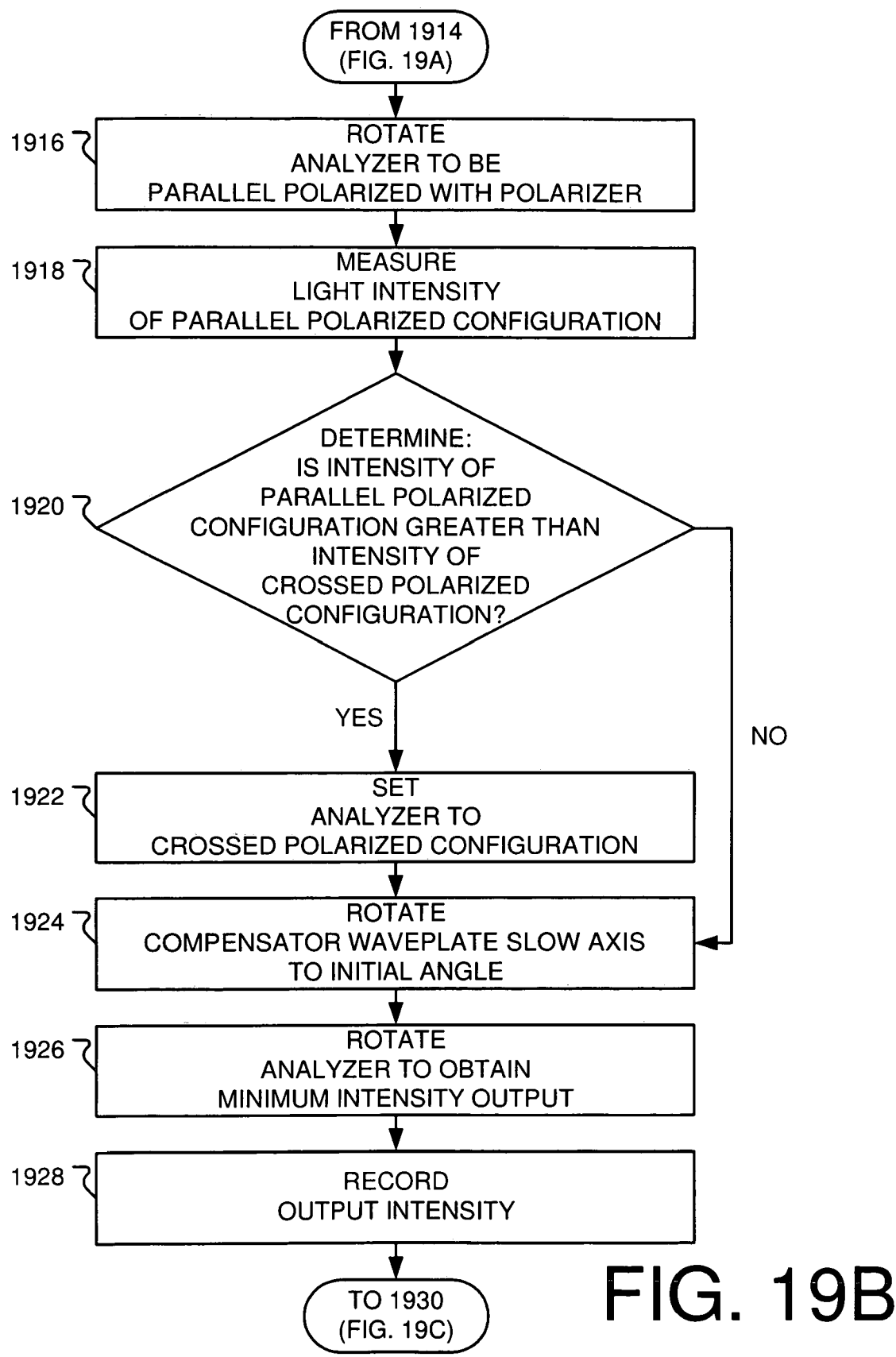

The process continues to FIG. 19B. As shown in FIG. 19B, upon measuring the transmitted light intensity for the crossed-polarizers configuration, the analyzer is rotated (1916) so that the analyzer is now in parallel polarizers configuration. The transmitted light is measured (1918) in the parallel polarizers configuration.

The measured light from the crossed-polarizers configuration and the parallel-polarizers configuration are compared to determine (1920) which of the two configurations transmits more light. If the parallel-polarizers configuration transmits more light, then the analyzer is set (1922) back to the crossed-polarizers configuration. Conversely, if the crossed-polarizers configuration transmits more light, then the analyzer is maintained in the parallel-polarizers configuration. In other words, whichever configuration transmits less light will be the proper configuration for the experimental process.

The compensator waveplate is then rotated (1924) slightly to an initial starting angle, thereby altering the orientation of the slow axis of the compensator waveplate. The initial starting angle can be arbitrarily defined or, alternatively, can be defined as a function of various measurement parameters. The analyzer is then rotated (1926) until a minimum intensity output is obtained. That output, along with the analyzer angle and the compensator waveplate angle, is then recorded (1928), and the process continues to FIG. 19C.

Figure 19C:
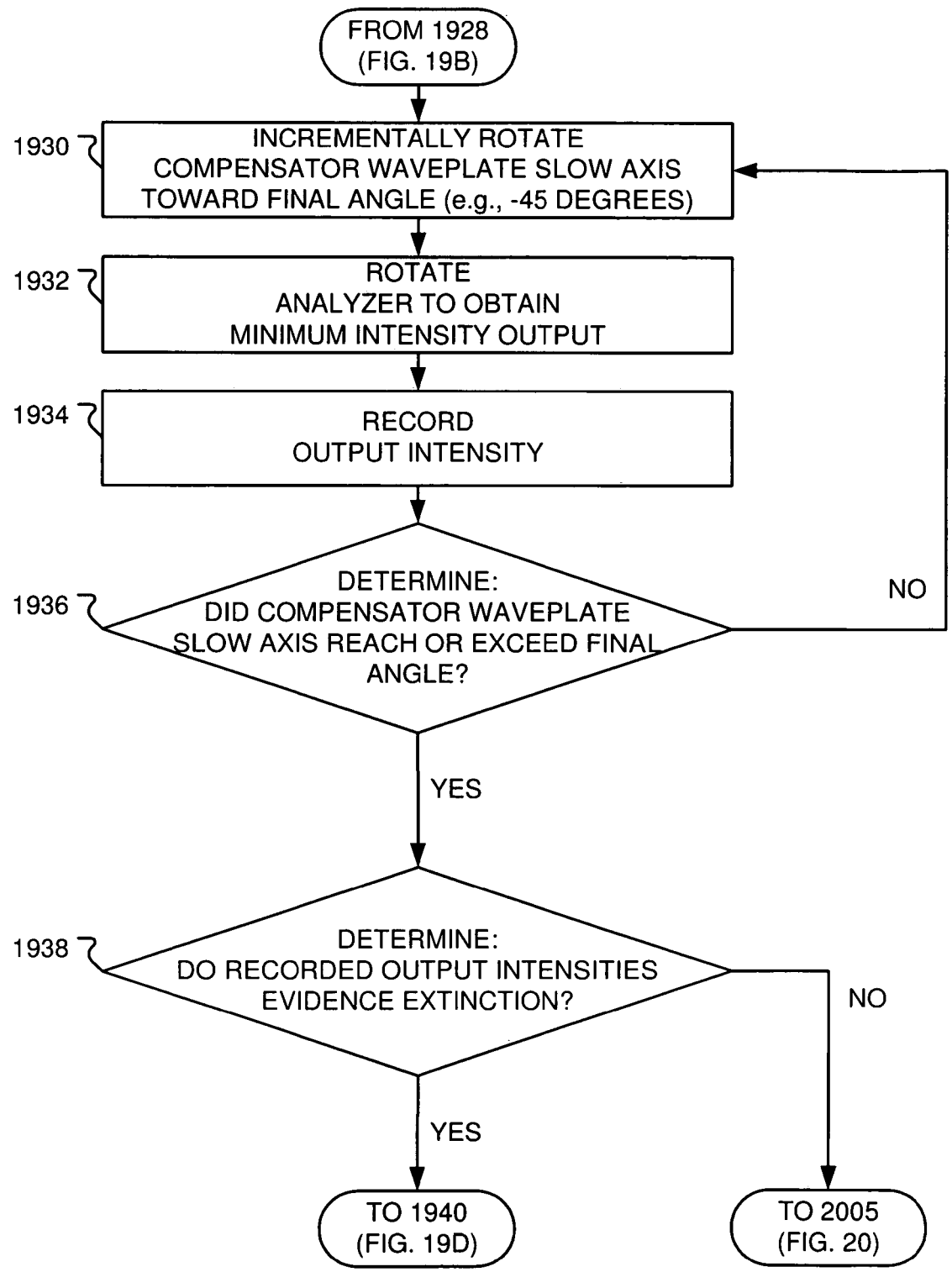

As shown in FIG. 19C, the compensator is incrementally rotated (1930) toward a final angle (e.g., −45 degrees). At that angle, the analyzer is again rotated (1932) to obtain a minimum intensity output. That analyzer angle, the compensator waveplate angle, and the intensity are again recorded (1934). Next, the process determines (1936) whether the compensator slow axis has been rotated to, or beyond, the final angle. Thus, for example, if the initial angle is 45 degrees and the final angle is −45 degrees, then the process determines whether the compensator slow axis angle has swept through a 90 degree arc. If the compensator slow axis has not swept through the 90 degree arc, then the compensator waveplate is again incrementally rotated (1930), and the process repeats until the compensator waveplate has swept through from positive 45 degrees to negative 45 degrees (or vice versa).

Once the compensator waveplate slow axis has swept through the 90 degree arc, the process determines (1938) whether any of the recorded outputs evidence extinction. In other words, the process determines whether the compensator waveplate was the correct waveplate to rotate. If the process determines (1938) that the compensator waveplate was, indeed, the correct waveplate to rotate, then the process continues to FIG. 19D. If, however, the process determines (1938) that the rotation of the compensator waveplate does not produce extinction (i.e., the compensator waveplate was the incorrect waveplate to rotate), then the process continues to FIG. 20.

Figure 19D:
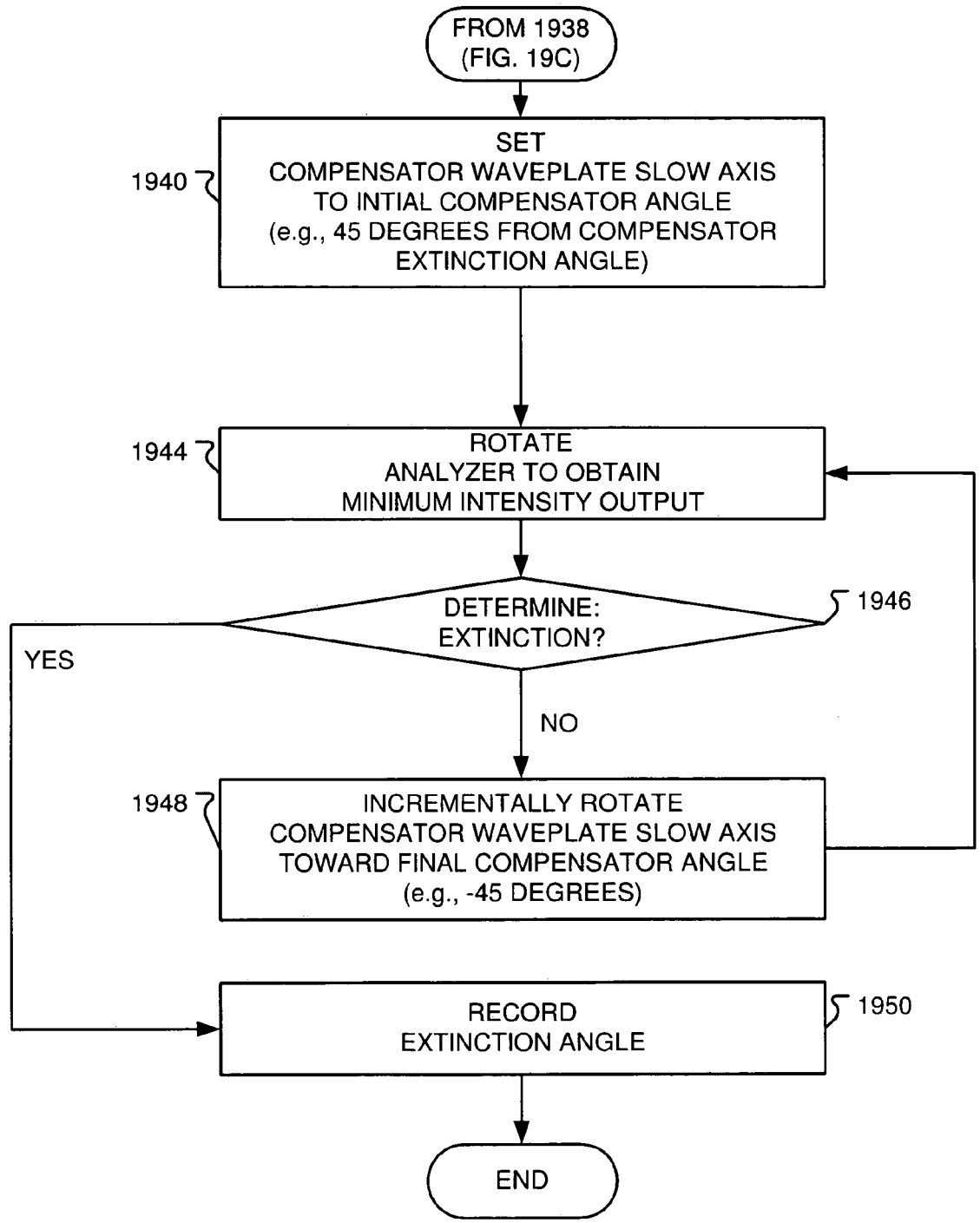

As shown in FIG. 19D, if the compensator waveplate is the correct waveplate for rotation, then the compensator slow axis is again set (1940) to its initial angle (e.g., 45 degrees from its extinction angle). Thereafter, the analyzer is rotated (1944) to obtain a minimum intensity output. The process then determines (1946) whether that minimum intensity is an extinction. If the minimum is determined to be extinction, then that extinction angle is recorded (1950), and the process ends. Conversely, if extinction is not achieved, then the compensator waveplate is incrementally rotated (1948), and the minimum output intensity is again measured by rotating (1944) the analyzer. This process is repeated until the extinction angle is determined.

As shown in FIG. 20, if the compensator waveplate is not the correct waveplate for rotation, then the compensator slow axis is again set (2005) to its initial angle (e.g., 45 degrees from its extinction angle). Thereafter, the analyzer is rotated (2015) to obtain a minimum intensity output. The process then determines (2020) whether or not that minimum intensity is an extinction. If extinction is achieved, then the extinction angle is recorded (2030), and the process ends. If, however, there is no extinction, then the process repeats by incrementally rotating (2025) the sample waveplate, and repeating the measurements until the extinction angle is determined.

The extinction angle provides a basis for calculating the birefringence of the sample and the compensator waveplates.

As shown in FIGS. 19A through 20, by rotating both the analyzer and one of the waveplates, the extinction angle can be determined without estimating the extinction angle from a measured minimum intensity. Whether the sample waveplate is to be rotated, or whether the compensator waveplate is to be rotated, can be determined experimentally, as described above. Unlike prior approaches in which only the waveplate is rotated, the TWC method of FIGS. 19A through 20 permits rotation of the analyzer, in conjunction with the rotation of one of the waveplates, thereby permitting more accurate measurements.

Eq. (49) is used to calculate the unknown $\phi_{samp}$. Two different expressions are derived to calculate the sample retardation depending if $\phi_1 = \phi_{samp}$ or $\phi_1 = \phi_{comp}$. These expressions are indicated at the end branches of the flow chart.

Figure 21:
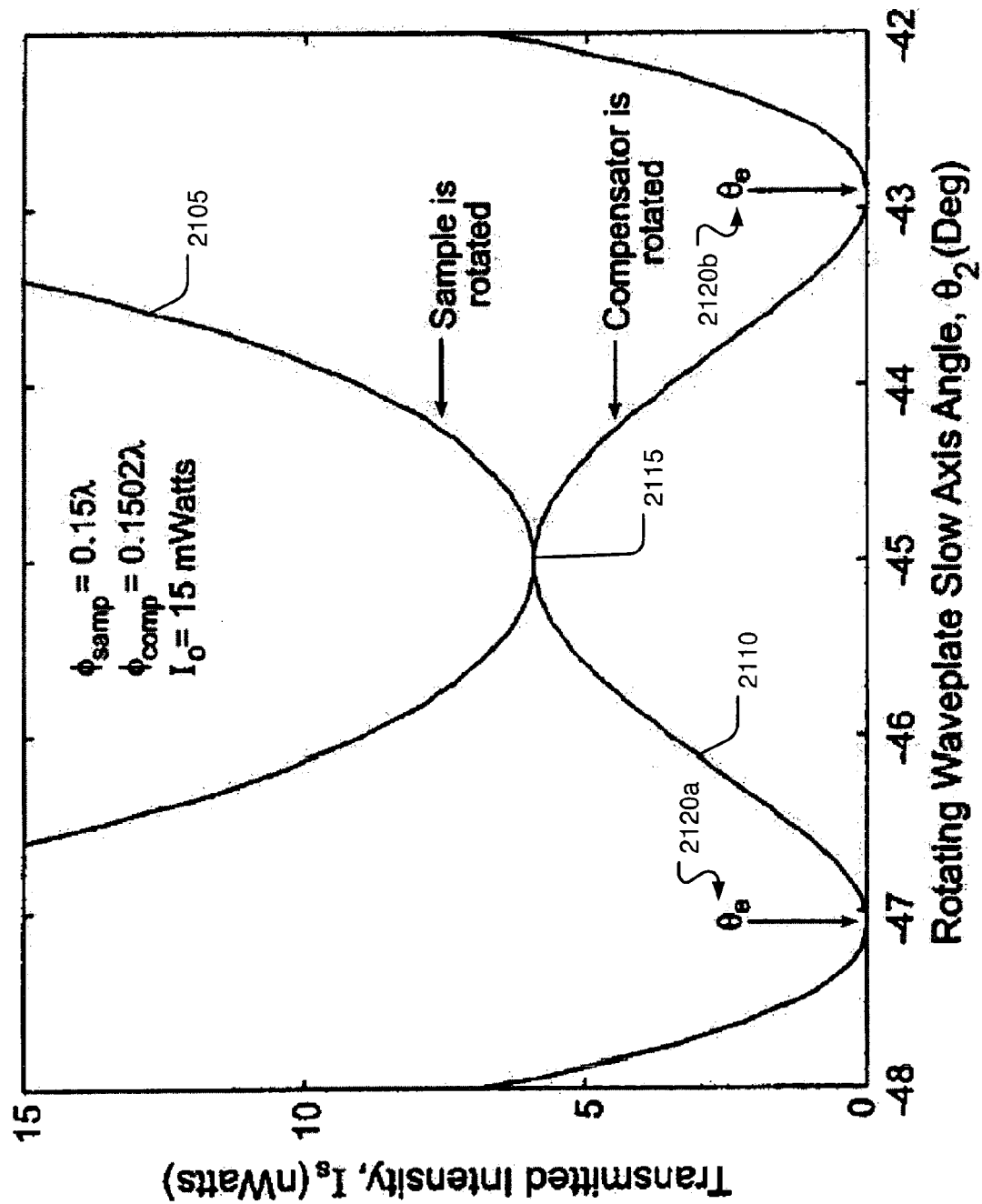
FIG. 21 is a graph illustrating intensity transmitted along the analyzer transmission direction as a function of a sample retardation for a particular experimental setup.

The applicability of the TWC technique for measuring retardation depends upon the capability of the optical system in resolving the point of extinction from the adjacent local maximum occurring for $\theta_2$ equal to +45° (FIG. 15). For the sample and compensator retardation values of FIGS. 16 and 18, the sample angle producing linearly polarized light is far enough from the adjacent maxima at +45° and −45° to be resolved. However, as the tangents of the sample and compensator retardations converge towards the same value, the angle producing linearly polarized light approaches +45° or −45° and the adjacent maximum intensity decreases which renders more difficult the distinction between the extinction and the adjacent maximum. This is illustrated in FIG. 21, where the intensity transmitted along the semi-minor axis of the output light polarization ellipse is plotted as a function of the rotating waveplate angle between −48° and −42° for a light source power $I_0$ equal to 15 mwatts, which corresponds to the power of a He—Ne laser used in experiments comparing Brace-Köhler and TWC techniques. The retardations of the sample and compensator are respectively equal to 0.15λ and 0.1502λ. In the case where the compensator is the rotating waveplate, a linearly polarized output is produced for $\theta_2$ equal to −47.08°, −42.91°, 132.92°, and 137.08°. When the compensator is rotated between −48° and −42°, extinction is produced for two of these angles shown in FIG. 21. Also shown in FIG. 21 is the intensity transmitted as the sample is rotated over the same angular range. When the sample is rotated from −45° to +45°, no linearly polarized output is produced and the semi-minor axis of the output polarization ellipse increases monotonically, similarly to that shown in FIG. 17. It will be shown later, analytically, that the intensity of the minimum produced at negative 45° when the sample is rotated, is equal to that of the local maximum produced when the compensator is rotated. This is shown in FIG. 21. The capability of the system for measuring the intensity difference between the intensity of the global minimum reached at ±45° when the non-linearly-polarizing waveplate is rotated and the intensity of the global minimum reached when the linearly-polarizing waveplate is rotated defines the resolution of the TWC technique. This depends upon the sensitivity of the system in measuring and resolving low-level intensities. In the example of FIG. 21, the minimum measurable intensity is less than 5 nwatts, in order to resolve the global minimum, when the compensator is rotated, and the local maximum, when the sample is rotated.

By deriving the exact expression for the intensity along the semi-axes of the output polarization ellipse occurring for $\theta_2$ equal to ±45°, general criteria for the resolution range of the TWC can be developed in terms of the input power $I_0$ and the minimum intensity $I_{min}$ measurable by the experimental system. Using Jones calculus, an electric field is represented with the phasor $$\vec{\varepsilon} = \begin{pmatrix} c_1 e^{j\beta_1} \\ c_2 e^{j\beta_2} \end{pmatrix} \quad (51)$$

where $c_1$ and $c_2$ are the amplitudes of the vibrations along the two polarization directions of the birefringent medium, and $\beta_1$ and $\beta_2$ the phase shifts introduced to the two vibrations upon traveling through the birefringent medium. Assuming two vibrations, respectively u(t) and v(t), along the slow and fast axes of the birefringent medium, the ellipse traced by the electric field can be represented by $$u(t) = \alpha_1 \cos \omega t \quad (52)$$

$$v(t) = \alpha_2 \cos(\omega t + \beta_2 - \beta_1) \quad (53)$$

with ωt the radian frequency. After transmission by the birefringent medium, it can be shown that the two semi-axes of the polarization ellipse traced by the electric field occur for the following radian frequencies $$\omega t_1 = -\frac{1}{2} \arctan \frac{c_2^2 \sin\{2(\beta_2 - \beta_1)\}}{c_1^2 + c_2^2 \cos\{2(\beta_2 - \beta_1)\}} \quad (54)$$

$$\omega t_2 = \omega t_2 + 90° \quad (55)$$

By substituting Eqs. (54) and (55) in Eqs. (42) through (45), the length of the semi-axes and $S_2$ of the polarization ellipse can be derived for $\theta_2$ equal to +45° and −45°

$$S_1(\theta_2 = 45°) = \cos\left(\frac{\phi_1 + \phi_2}{2}\right) \quad (56)$$

$$S_2(\theta_2 = 45°) = \sin\left(\frac{\phi_1 + \phi_2}{2}\right) \quad (57)$$

$$S_1(\theta_2 = -45°) = \cos\left(\frac{\phi_1 - \phi_2}{2}\right) \quad (58)$$

$$S_2(\theta_2 = -45°) = \sin\left(\frac{\phi_1 - \phi_2}{2}\right) \quad (59)$$

To calculate the actual intensity along the semi-axes of the polarization ellipse, we use the fact that the intensity of the electric field is given by $\vec{\epsilon} \cdot \vec{\epsilon}^*$. Therefore, the intensity $I_S$, along the semi axes of the polarization ellipse is $$I_s(\theta_2 = \pm 45°) = S_i(\pm 45°)^2 I_0 \qquad (60)$$

where i can have the value of 1 or 2 and $I_0$ is the initial light source intensity.

The intensity along the semi-axes of the output polarization ellipse is derived using Eqs. (56) through (59)

$$I_1(\theta_2 = 45°) = I_0 \cos\left(\frac{\phi_1 + \phi_2}{2}\right)^2 \qquad (61)$$

$$I_2(\theta_2 = 45°) = I_0 \sin\left(\frac{\phi_1 + \phi_2}{2}\right)^2 \qquad (62)$$

$$I_1(\theta_2 = -45°) = I_0 \cos\left(\frac{\phi_1 - \phi_2}{2}\right)^2 \qquad (63)$$

$$I_2(\theta_2 = -45°) = I_0 \sin\left(\frac{\phi_1 - \phi_2}{2}\right)^2 \qquad (64)$$

In FIG. 21, in order for the local maximum occurring for $\theta_2$ equal to $-45°$ to be resolved, its intensity should be greater than the minimum intensity $I_{min}$ measurable by the experimental system. This condition is expressed as follows in terms of the intensities above $$I_0 \cos\left(\frac{\phi_1 + \phi_2}{2}\right)^2 > I_{min} \qquad (65)$$

$$I_0 \sin\left(\frac{\phi_1 + \phi_2}{2}\right)^2 > I_{min} \qquad (66)$$

$$I_0 \cos\left(\frac{\phi_1 - \phi_2}{2}\right)^2 > I_{min} \qquad (67)$$

$$I_0 \sin\left(\frac{\phi_1 - \phi_2}{2}\right)^2 > I_{min} \qquad (68)$$

Using the four equations above, the resolvability condition in terms of the retardation values $\phi_1$ and $\phi_2$ can be stated as a function of sample and compensator retardations, the input power and the minimum measurable power $$2\arcsin\left(\sqrt{\frac{I_{min}}{I_0}}\right) < \phi_1 - \phi_2 < 2\arccos\left(\sqrt{\frac{I_{min}}{I_0}}\right) \qquad (69)$$

$$2\arcsin\left(\sqrt{\frac{I_{min}}{I_0}}\right) < \phi_1 + \phi_2 < 2\arccos\left(\sqrt{\frac{I_{min}}{I_0}}\right) \qquad (70)$$

Figure 22:
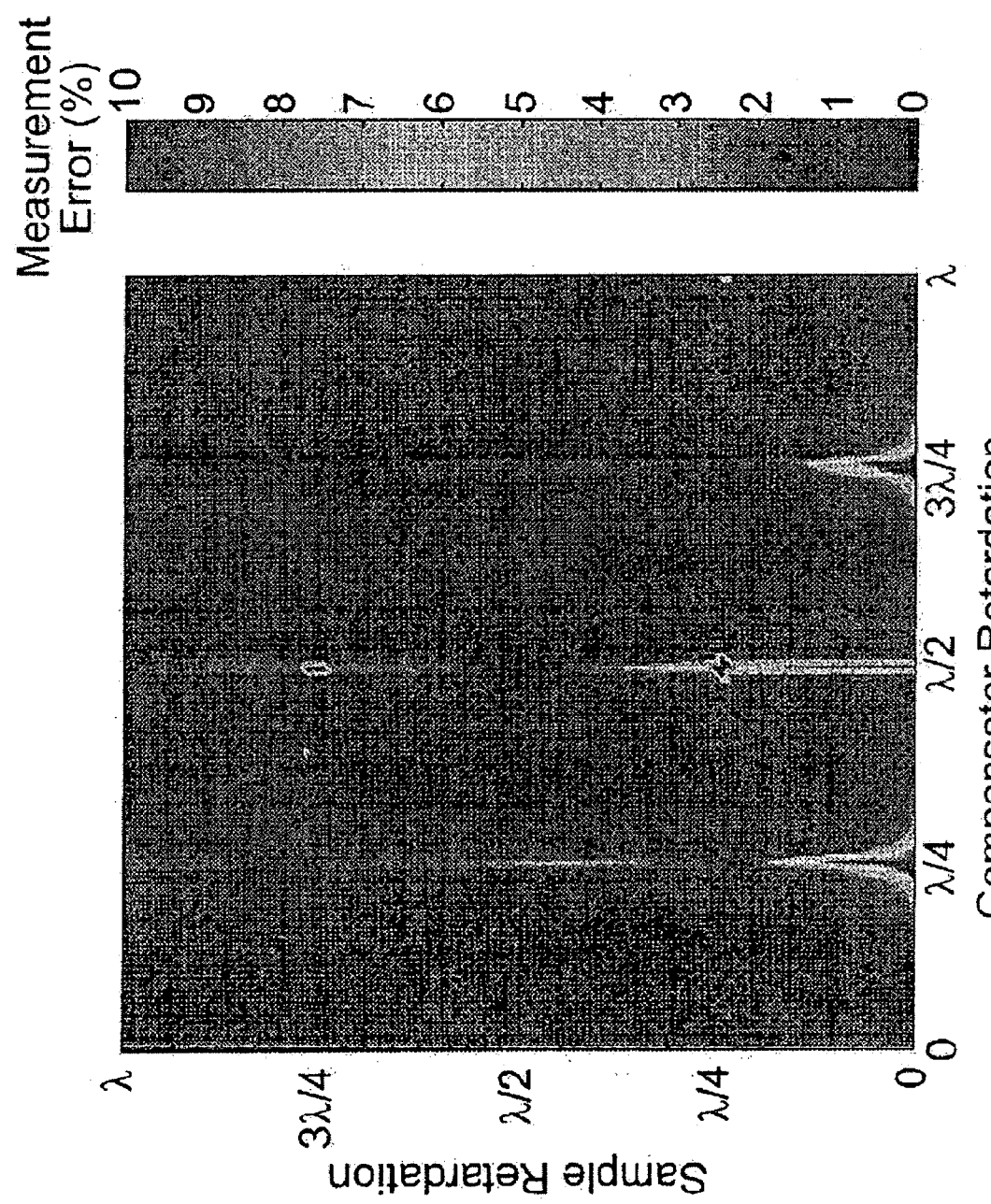
FIG. 22 is a graph illustrating measurement error for TWC for retardations ranging from 0 to $\lambda$.

The measurement error using the TWC is calculated by determining the angular measurement uncertainty, which is defined as the angular range over which the output light intensity decreases beyond the minimum measurable intensity. The corresponding measured retardations at either extreme of the angular range are calculated using the TWC formulas and compared to the actual sample retardation. FIG. 22 represents the relative measurement error for sample and compensator retardations ranging from 0 to λ. A minimum measurable intensity of 5 nwatts is considered to plot FIG. 22 which corresponds to the minimum measurable intensity of a UDT photodetector that is used at 632.8 nm to compare the accuracy of the Brace-Köhler compensator and the TWC. The relative error of the measurement remains below 2% over the entire range of sample and compensator retardations except when the compensator retardation is a multiple of a quarter-waveplate or a half-waveplate in which case the error increases beyond 10%. The error remains low however when the sample retardation is a multiple of a quarter-waveplate or a half-waveplate. When either waveplate in the two-waveplate system is a quarter-waveplate, it needs to be the rotating waveplate to satisfy the condition stated in Eq. (50). Substituting $\phi_2$ equal to 90° in Eq. (49), the angle $\phi_2$ producing linearly polarized light is $$\theta_2 = \frac{1}{2}\arcsin\left(\frac{\tan\phi_1}{\infty}\right) \qquad (71)$$

$$\theta_2 = 0 \qquad (72)$$

If the sample is the fixed waveplate and the compensator is the rotating quarter-waveplate, the sample unknown retardation is given by $$\phi_{samp} = \arctan\{\tan(90°)\sin(2\theta_2)\} \qquad (73)$$

$$= \arctan\{\infty \sin(2\theta_2)\} \qquad (74)$$

$$= 90° \qquad (75)$$

considering the angular uncertainty of the measurement which results in not measuring accurately $\theta_2$ equal to zero. When the compensator is a quarter-waveplate, the two-waveplate compensator technique determines erroneously the sample retardation as being equal to a quarter waveplate. This is the basis for the measurement error increasing in FIG. 22 when the compensator retardation approaches a multiple of a quarter-waveplate. If the sample is the rotating quarter waveplate and the compensator the fixed waveplate, the sample unknown retardation is given by $$\phi_{samp} = \arctan\left\{\frac{\tan(90°)}{\sin(2\theta_2)}\right\} \qquad (76)$$

$$= \arctan\left\{\frac{\infty}{\sin(2\theta_2)}\right\} \qquad (77)$$

$$= 90° \qquad (78)$$

When the sample is a quarter-waveplate, the TWC technique determines its retardation correctly. This is the basis for the measurement error remaining low in FIG. 22 when the sample retardation approaches a multiple of a quarter-waveplate. A similar reasoning can be applied and can show that the TWC technique determines erroneously a sample retardation when the compensator is a half-waveplate and determines correctly the sample retardation when it is a half-waveplate.

The Brace-Köhler compensator and TWC techniques have been studied thoroughly in previous sections. The following section compares their ability in measuring accurately very small retardations. The measurement error is calculated using a similar approach to the one that had been used previously to calculate the error of the TWC. In the case of the TWC, the exact angle to produce linearly polarized light is calculated for any given pair of sample and compensator retardations. The transmitted intensity along the semi-minor axis of the output ellipse is calculated for angles near the extinction angle. The angular range over which the intensity is lower than the minimum measurable intensity is thus determined. The sample retardation is computed at both ends of the angular range corresponding to the angles for which the output intensity increases beyond the minimum measurable intensity. The maximum relative deviation from the exact retardation is defined as the relative measurement error. In the case of the Brace-Köhler compensator however, this approach had to be slightly modified since the intensity minimum measured is greater than the minimum measurable intensity. Therefore, the angular uncertainty is defined as the angular range over which the intensity variation around the minimum of intensity is lower than the minimum measurable intensity change. The relative measurement error is then computed by calculating the maximum retardation deviation from the exact sample retardation similarly to what is done in the TWC case.

Figure 23:
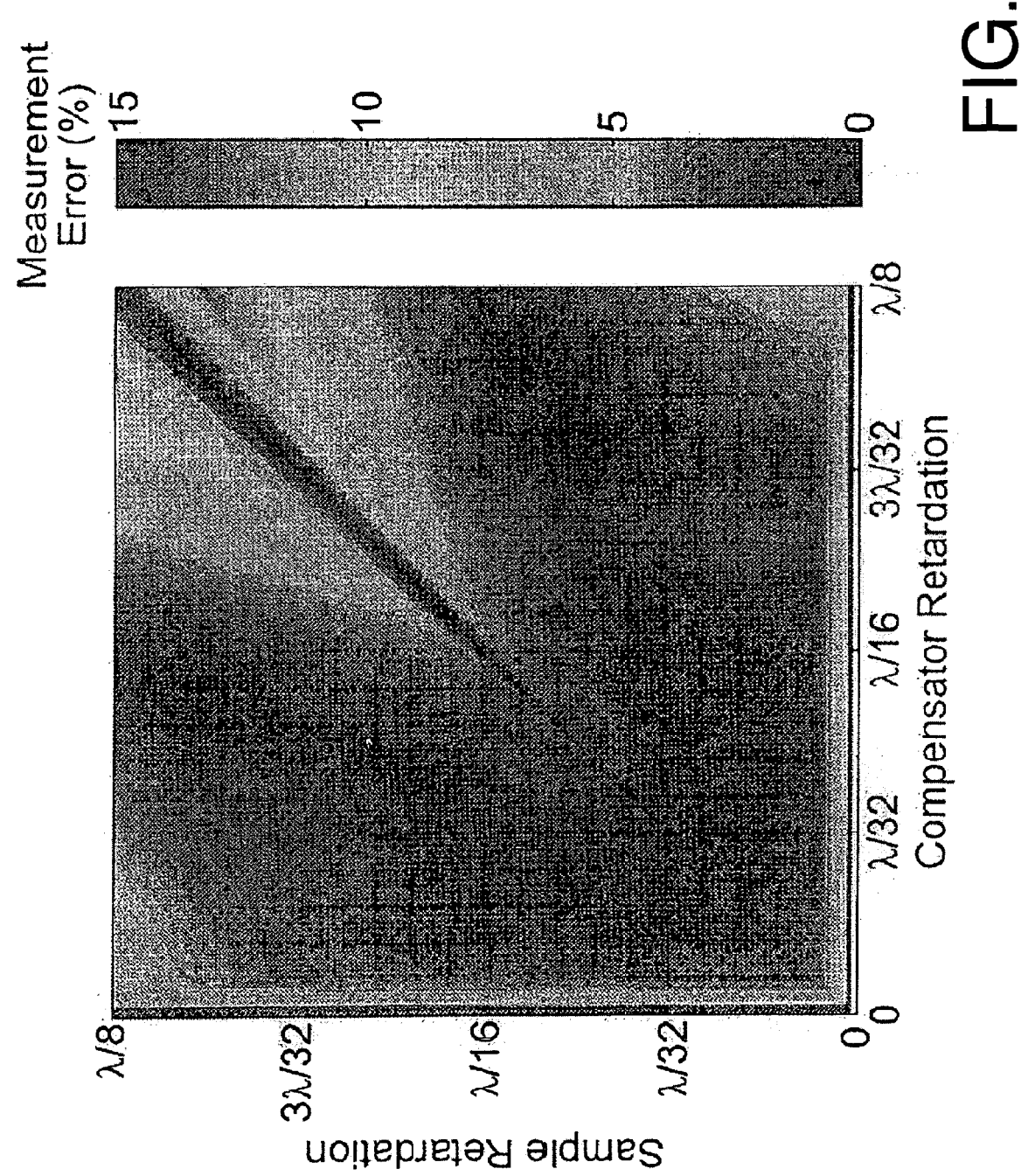
FIG. 23 is a graph illustrating measurement error in a Brace-Köhler compensator method for retardations ranging from 0 to $\lambda/8$.
Figure 24:
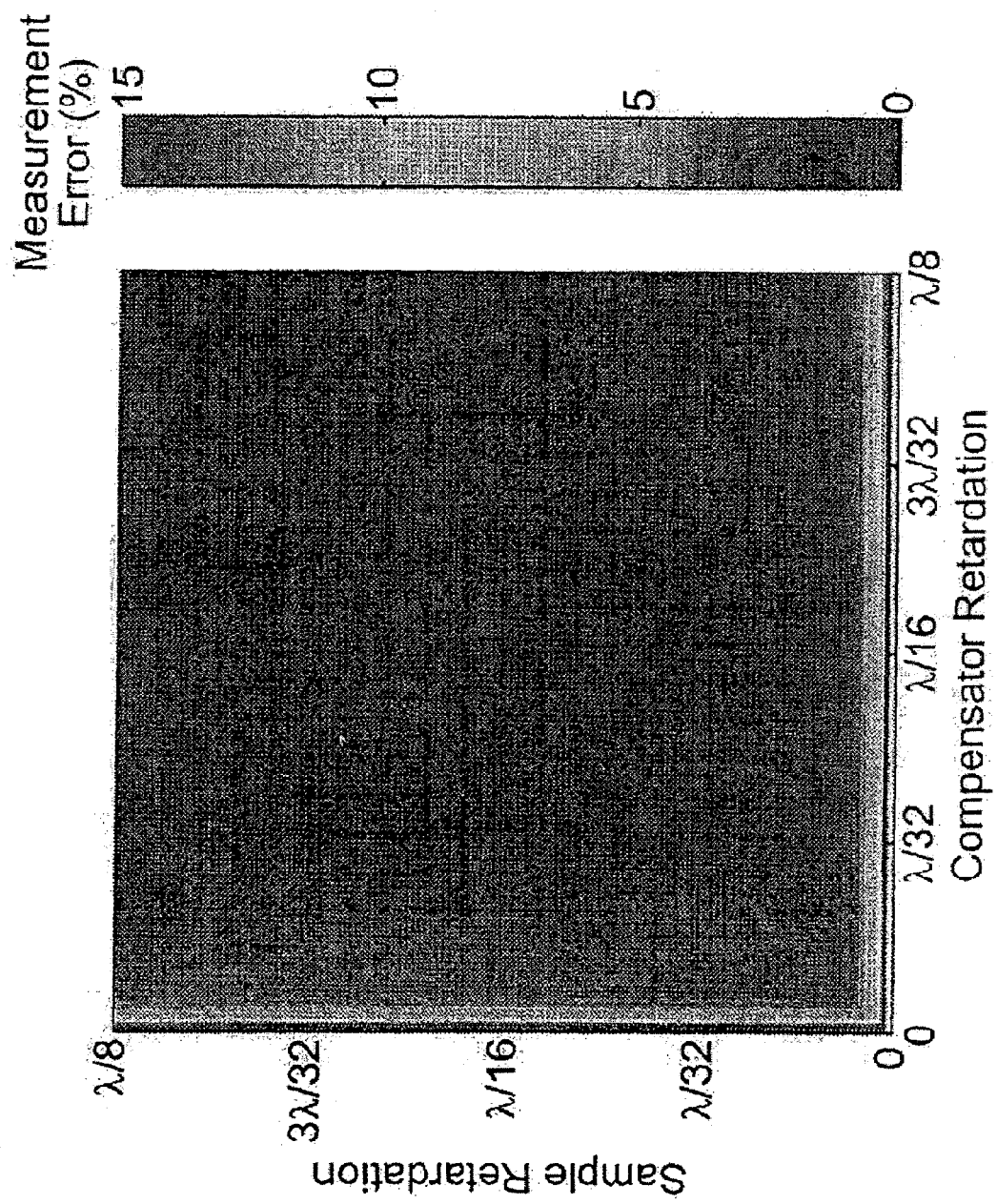
FIG. 24 is a graph illustrating measurement error for TWC approach for retardations ranging from 0 to $\lambda/8$.

The measurement error is calculated for the Brace-Köhler compensator and the TWC in FIGS. 23 and 24 for sample and compensator retardations between 0 and $$\frac{\lambda}{8}.$$

Note that in the case of the Brace-Köhler compensator, the error calculated in FIG. 23 takes into account the measurement angular uncertainty and the error due to the small retardations approximation. Both plots were generated by considering 200 retardations between 0 and $$\frac{\lambda}{8}$$

for the sample and similarly, 200 retardations for the compensator. In the TWC case, 71.41% of the total number of calculated error data used to plot FIG. 24 are less than 1% whereas only 22.125% of the total number are less than 1% in FIG. 23 for the Brace-Köhler compensator. For the latter, the error increases as sample and compensator retardations increase, due to the small retardation approximation which predominates over the error due to the uncertainty in the angle measurement. It also increases as sample and compensator retardations become very small due predominantly to the uncertainty of the angle measurement. More precisely, it increases beyond 10% for retardations less than $$\frac{\lambda}{500}.$$

At that very low level of retardation, the absolute uncertainty of the measurement is not greater than that at larger retardations. However, it becomes relatively larger compared to the retardation to be measured. The TWC error shown in FIG. 24 is due to the angular uncertainty of the measurement. Therefore, as the retardations increase, the relative error decreases, as there are no small retardations approximation. However, as retardations become very small, the relative error increases. Similar the case of the Brace-Köhler compensator, the error increases beyond 10% for retardations less than $$\frac{\lambda}{500}$$

and this is also due to the fact that the error due to the angular uncertainty becomes relatively large.

Figure 25:
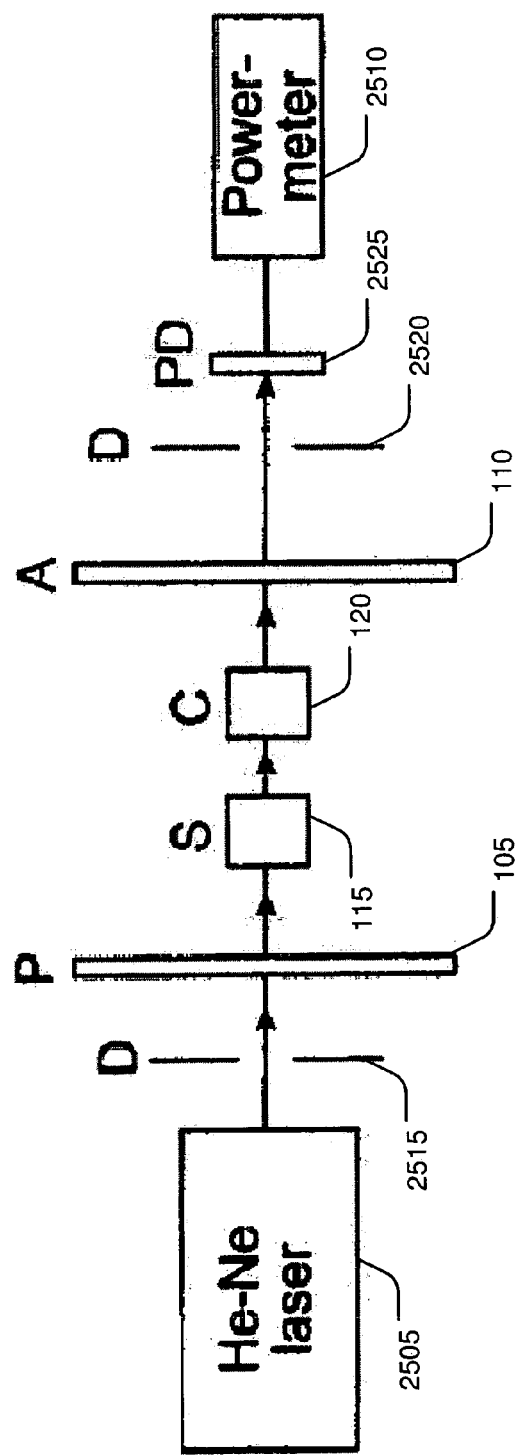
FIG. 25 is a block diagram showing an embodiment of an experimental configuration for single-point birefringence measurements.

The Brace-Köhler and TWC techniques are also compared experimentally using the configuration shown in FIG. 25. A He—Ne laser 2505 of output power approximately equal to 15 mwatts is used as a light source. The polarizers P 105 and A 110 in FIG. 25 are Glan Thompson prisms.

The extinction ratio of the polarizers is measured prior to the retardation measurements and is equal to $6.6 \times 10^{-8}$. The sample S 115 and the compensator C 120 are two Brace-Köhler compensators manufactured by Olympus, respectively U-CBR1 and U-CBR2. Their retardations are respectively equal to 59.66 nm and 21.54 nm. The compensator of lesser retardation is used as a sample, whereas the other one is used as a compensator. The extinction angles $\theta_0$ of both compensators are first measured individually between crossed polarizers. Several measurements are averaged. The sample is placed at 45 degrees from extinction, whereas the compensator is placed at extinction. For the Brace-Kohler compensator measurements, the compensator is rotated until a minimum of intensity is obtained. The average angle $\theta_{min}$ producing a minimum of intensity is used to calculate the retardation of the sample. For the TWC technique, the compensator and the analyzer are rotated successively until extinction is obtained. The average angle $\theta_e$ producing extinction is used to calculate the sample retardation. The results of these experiments are summarized in Tables 3 and 4.

TABLE 3

Retardation measurements of small retardation waveplates using Brace-Köhler compensator method.

| Waveplate Type | Manufacturer's Description | $\theta_0$ | $\theta_{min}$ | Intensity | Measured Retardation | Deviation |
|---|---|---|---|---|---|---|
| U-CBR2 | 21.54 nm | −0.15° | −10.5° | 10.17 microwatts | 21.09 nm | 2.09% |

TABLE 4

Retardation measurements of small retardation waveplates using TWC method.

| Waveplate Type | Manufacturer's Description | $\theta_0$ | $\theta_{min}$ | Intensity | Measured Retardation | Deviation |
|---|---|---|---|---|---|---|
| U-CBR2 | 21.54 nm | −0.15° | −9.52° | 194.6 nanowatts | 21.45 nm | 0.42% |

The minimum intensity measured with the Brace-Köhler technique is approximately 50 times brighter than that measured with the TWC technique. With the TWC, the compensator angle producing linearly polarized light is determined by rotating the analyzer transmission direction perpendicular to the polarization direction of the electric field. Finding a null of intensity renders the determination of the compensator angle more accurate. Conversely, in-the case of the Brace-Köhler compensator finding a minimum of intensity instead of a null renders the measurement less accurate. Further, the use of a small retardation approximation also affects the accuracy of the measurement for the Brace-Köhler compensator. This is verified experimentally as the relative deviation from the sample waveplate retardation provided by the manufacturer is only 0.42% with the TWC whereas it is 2.09% with the Brace-Köhler compensator.

In the previous sections, experimental procedures were presented using the TWC technique to measure a sample's retardation magnitude. In this section, the Automated Two-Waveplate Compensator (ATWC) technique is presented.

Previously, the sample slow axis orientation $\theta_1$ was assumed to be known and the sample was oriented at 45 degrees from extinction. For a sample whose slow axis orientation is not known, a rather simple preliminary experiment can be conducted to determine its orientation. This gives the ability of locating a sample slow axis orientation. The sample can be placed between crossed polarizers. It can then be rotated until complete extinction is obtained. This orientation corresponds to the case where the sample slow and fast axes are parallel to the crossed-polarizers transmission direction. The sample slow and fast axes are thus determined. Rotating the sample 45 degrees of extinction, and following the TWC experimental procedure previously described allows one to measure the sample retardation magnitude.

The previous experimental procedure, however, is directed to real-time reading of the intensity transmitted through the analyzer to determine the compensator angle producing linearly polarized light. This process can be automated. For single-point retardation measurement, the sample is oriented at 45 degrees of extinction. The compensator waveplate is rotated by a small angular increment from its extinction position. Keeping the compensator waveplate in this position, the analyzer is rotated 180 degrees in suitably small angular increments, and the transmitted intensity is recorded for each angle. After the analyzer has been rotated 180 degrees, it is rotated back to its initial position. The compensator waveplate is rotated to a second angle and the analyzer is rotated again like it was for the previous compensator position. The procedure is repeated until the compensator has been rotated over a range of angles depending on the order of magnitude of the retardation to be measured. The recorded intensities are then inspected to determine which of the compensator angles produced extinction. Both the angular ranges of the compensator and the analyzer can be reduced if the retardation order of magnitude is known. The ATWC technique is particularly useful for full-field retardation measurements in which case numerous image pixels need to considered. The experimental procedure for one embodiment, among others, of the ATWC technique is represented in FIGS. 27A and 27B.

Figure 27A:
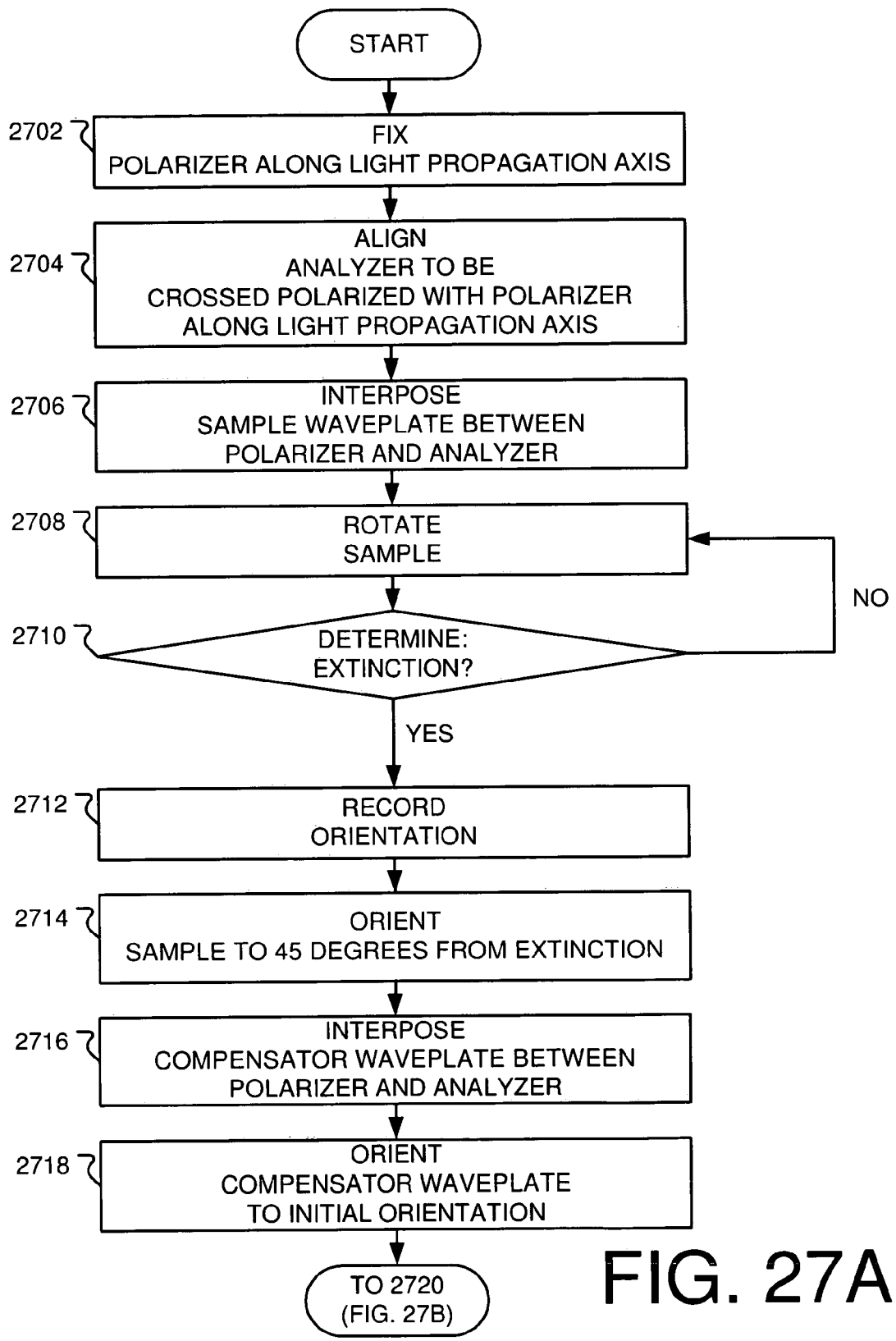

As shown in FIG. 27A, one embodiment of the process, among others, begins by fixing (2702) a polarizer along a light propagation axis. A second polarizer, which is referred to herein as an analyzer, is aligned (2704) along the light propagation axis such that the analyzer is in a crossed-polarizers configuration with the fixed polarizer. A sample waveplate is then interposed (2706) between the polarizer and the analyzer. That sample waveplate is rotated (2708). The sample is rotated until the process determines (2710) that the sample is oriented at an extinction angle. Upon achieving extinction, the orientation of the sample waveplate is recorded (2712).

The sample waveplate is then oriented (2714) at 45 degrees from extinction, thereby providing maximum light transmission. Thereafter, a compensator waveplate is interposed (2716) between the polarizer and the analyzer. At this point, in some embodiments, the setup may appear similar to that shown in FIG. 1.

The compensator waveplate is then oriented (2718) to an initial orientation. That initial orientation can be arbitrarily designated, or, alternatively, can be set in accordance with various predefined conditions. The process then continues to FIG. 27B.

As shown in FIG. 27B, the compensator is then oriented (2720) to an initial orientation, and, also, the analyzer is oriented (2722) to an initial orientation. Similar to the compensator waveplate orientation, the analyzer initial orientation can be arbitrarily designated. Given this configuration, an image (or intensity) is recorded (2724).

The process incrementally rotates (2728) the analyzer and records (2724) the image at each incremental angle of the analyzer, until the process determines (2726) that all analyzer angles have been examined for that given compensator waveplate. When images for all analyzer angles for a given compensator waveplate have been recorded, then the compensator waveplate is incrementally rotated (2732), and the analyzer again sweeps through the various angles. This process is repeated until images have been obtained for all desired angles for both the compensator waveplate and all desired angles for the analyzer.

Once all images have been recorded, the process retrieves (2734) the recorded images (or intensities), and inspects (2736) the images (or intensities) for extinction. This, for some embodiments, can be done on a pixel-by-pixel basis, thereby providing a robust method for obtaining spatially-resolved extinction-angle images. This information can be used to obtain birefringence information.

Figure 26:
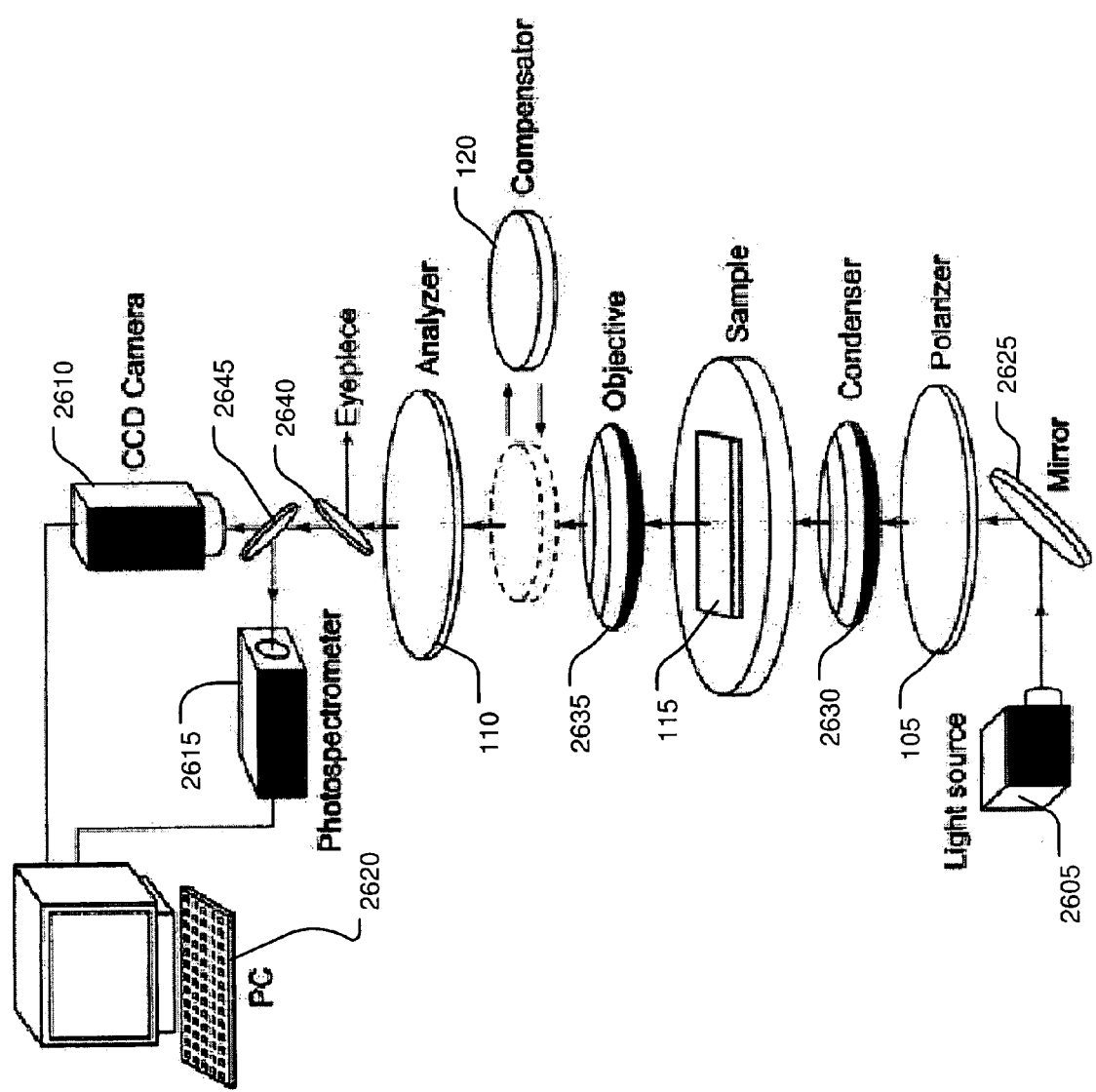
FIG. 26 is a block diagram showing another embodiment of an experimental configuration for full-field birefringence measurements.

The experimental configuration used to implement ATWC for full-field measurements is shown in FIG. 26. A sample is placed on the microscope stage and the experimental procedure described in FIGS. 27A and 27B is applied to all pixels or groups of pixels in the image. The sample being placed on the microscope stage between crossed polarizers, it is rotated and an image is recorded for each angle. Using an image processing software, the angle producing extinction is determined for each pixel or group of pixels in the image. This allows the computation of the retardation orientation at all points. The microscope stage is then rotated so each pixel or group of pixels is at 45 degrees from extinction. The compensator and analyzer are rotated as is shown in FIGS. 27A and 27B to determine which compensator orientation produces linearly polarized light. This allows the computation of the retardation magnitude at all points.

The intensity expressions derived earlier can be used to construct systems of equations that may be helpful in retrieving the retardation magnitude and orientation of a sample.

The expression of the intensity transmitted through the analyzer has been derived and is given by Eq. (6)

$$I_A = \varepsilon_{Ax}\varepsilon_{Ax}^* \quad (79)$$

$$= \sin^2\theta_2 \left\{ \cos^2\theta_2 \cos^2\frac{\phi_1}{2} + \cos^2(2\theta_1 - \theta_2)\sin^2\frac{\phi_1}{2} \right\} +$$

$$\cos^2\theta_2 \left\{ \sin^2\theta_2 \cos^2\frac{\phi_1}{2} + \sin^2(2\theta_1 - \theta_2)\sin^2\frac{\phi_1}{2} \right\} -$$

$$\frac{1}{2}\sin 2\theta_2 \{\sin 2\theta_2 \cos^2\frac{\phi_1}{2}\cos\theta_2 - \sin(4\theta_1 - 2\theta_2)\cos\phi_2\sin^2\frac{\phi_1}{2} -$$
$$\sin 2\theta_1 \sin\phi_1 \sin\phi_2\} \qquad (5)$$

The Brace-Köhler compensator technique assumes that the sample slow axis orientation $\theta_1$ is equal to 45 degrees. This method therefore measures the sample retardation magnitude $\phi_1$. Two intensity equations are used to determine the sample retardation magnitude and orientation. In the above system, the intensity depends on four variables $\phi_1$, $\phi_2$, $\theta_1$, and $\theta_2$. The unknowns are $\phi_1$ and $\theta_1$. The retardation magnitude of the second waveplate $\phi_2$ is fixed and known. By varying the compensator angle $\theta_2$, enough intensity equations can be generated in order to determine the unknowns $\phi_1$ and $\theta_1$. Substituting $\theta_2$ to equal to 0, 45°, and −45° in Eq. (6), three intensity equations are generated $$I_1(\theta_2 = 0) = \sin^2\frac{\phi_1}{2} \qquad (80)$$

$$I_2 = (\theta_2 = 45°) = \sin^2\frac{\phi_2}{2} + \sin(2\theta_1)\sin^2\frac{\phi_1}{2}\cos\theta_2 + \qquad (81)$$
$$\frac{1}{2}\sin(2\theta_1)\sin\phi_1\sin\phi_2$$

$$I_3(\theta_2 = -45°) = \sin^2\frac{\phi_2}{2} + \sin^2(2\theta_1)\sin^2\frac{\phi_1}{2}\cos\theta_2 - \qquad (82)$$
$$\frac{1}{2}\sin(2\theta_1)\sin\phi_1\sin_2$$

The system of intensity equations above can be solved for $\phi_1$ and $\theta_1$ provided that the transmitted intensities $I_1$, $I_2$, and $I_3$ are known. Using $I_1$ and $I_2$, the sample retardation magnitude and orientation are given by $$\phi_1 = 2\arccos\left\{\frac{I_2 - \sin^2\frac{\phi_2}{2} - I_1\cos\phi_2}{\sin\phi_2\sqrt{I_1}}\right\} \qquad (83)$$

$$\theta_1 = \frac{1}{2}\arcsin\left\{\frac{\sqrt{I_1}}{\sin\frac{\phi_1}{2}}\right\} \qquad (84)$$

Using $I_2$ and $I_3$ $$\phi_1 = 2\arccos\left\{\frac{1}{\sqrt{2}}\frac{(I_2 - I_3)\sqrt{\cos\phi_2}}{\sin\phi_2\sqrt{I_2 + I_3 - \sin^2\frac{\phi_2}{2}}}\right\} \qquad (85)$$

$$\theta_1 = \frac{1}{2}\arcsin\left\{\frac{I_2 - I_3}{\sin\phi_1\sin\phi_2}\right\} \qquad (86)$$

This constitutes the basis for a new retardation measurement technique, the Phase-Stepping Two-Waveplate Retarder (PSTWR). Different retardation biases are generated by rotating the compensator at different angles. Measuring the intensities allow to solve systems of intensity equations for the sample retardation magnitude and orientation $\phi_1$ and $\theta_1$. This method can be implemented for single-point or full-field retardation measurements.

Eq. (6) can also be further developed so the PSTWR can be applied for any bias angles $\theta_2$. Using trigonometric relationships, the variables $\theta_1$ and $\theta_2$ are decoupled $$I_A = \frac{1}{2}A(\theta_2) + \frac{1}{2}A(\theta_2)\cos\phi_1 - \qquad (87)$$
$$\frac{1}{2}\sin 4\theta_2\sin^2\frac{\phi_2}{2}\sin 2\theta_1\cos 2\theta_1 + \frac{1}{2}A(\theta_2) - A(\theta_2)\sin^2\theta_1 +$$
$$\frac{1}{2}\sin 4\theta_2\sin^2\frac{\phi_2}{2}\sin 2\theta_1\cos 2\theta_1 - \frac{1}{2}A(\theta_2)\cos\phi_1 +$$
$$A(\theta_2)\sin^2 2\theta_1\cos\phi_1 + \frac{1}{2}\sin^2 2\theta_1 - \frac{1}{2}\cos\phi_1\sin^2 2\theta_1 +$$
$$\frac{1}{2}\sin 2\theta_2\sin\phi_2\sin 2\theta_1\sin\phi_1$$

with $$A(\theta_2) = \sin^2 2\theta_2\sin^2\frac{\phi_2}{2} \qquad (88)$$

Successively factoring by $$A(\theta_2) - \frac{1}{2} \text{ and } (\cos\phi_1 - 1)$$

leads to $$I_A = A(\theta_2) - \frac{1}{2}\sin 4\theta_2\sin^2\frac{\phi_2}{2}\sin 2\theta_1\cos 2\theta_1(\cos\phi_1 - 1) + \qquad (89)$$
$$\left\{A(\theta_2) - \frac{1}{2}\right\}\sin^2 2\theta_1(\cos\phi_1 - 1) +$$
$$\frac{1}{2}\sin 2\theta_2\sin\phi_2\sin 2\theta_1\sin\phi_1$$

Subtracting $A(\theta_2)$ on both sides of the equation, $$I_A - A(\theta_2) = -\sin 4\theta_2\sin^2\frac{\phi_2}{2}\sin 2\theta_1\cos 2\theta_1\sin^2\frac{\phi_1}{2} - \qquad (90)$$
$$2\left\{A(\theta_2) - \frac{1}{2}\right\}\sin^2 2\theta_1\sin^2\frac{\phi_1}{2} +$$
$$\frac{1}{2}\sin 2\theta_2\sin\phi_2\sin 2\theta_1\sin\phi_1$$

The unknowns in the above equation are $$X_1 = \sin 2\theta_1\cos 2\theta_1\sin^2\frac{\phi_1}{2} \qquad (91)$$

$$X_2 = \sin^2 2\theta_1\sin^2\frac{\phi_1}{2} \qquad (92)$$

$$X_3 = \sin 2\theta_1\sin\phi_1 \qquad (93)$$

Assuming $$a(\theta_{2,i}) = -\sin 4\theta_{2,i}\sin^2\frac{\phi_2}{2} \qquad (94)$$

$$b(\theta_{2,i}) = 1 - 2A(\theta_{2,i}) \qquad (95)$$

$$c(\theta_{2,i}) = \frac{1}{2}\sin 2\theta_{2,i}\sin\phi_2 \qquad (96)$$

where i denotes the ith bias angle, the following matrix equation is obtained $$\begin{pmatrix} a(\theta_{2,1}) & b(\theta_{2,1}) & c(\theta_{2,1}) \\ a(\theta_{2,2}) & b(\theta_{2,2}) & c(\theta_{2,2}) \\ a(\theta_{2,3}) & b(\theta_{2,3}) & c(\theta_{2,3}) \end{pmatrix}\begin{pmatrix} X_1 \\ X_2 \\ X_3 \end{pmatrix} = \begin{pmatrix} I_{A,1} - A(\theta_{2,1}) \\ I_{A,2} - A(\theta_{2,2}) \\ I_{A,3} - A(\theta_{2,3}) \end{pmatrix} \qquad (97)$$

$$TX = J \qquad (98)$$

where the matrix T is obtained by calculating $a(\theta_{2,i})$, $b(\theta_{2,i})$, and $c(\theta_{2,i})$ for the various bias angles $\theta_{2,i}$, and the matrix J is obtained by measuring the transmitted intensities at each bias angle and calculating $A(\theta_{2,i})$ Solving the matrix equation for X $$X = T^{-1}J \qquad (99)$$

Using the expressions of $X_1$, $X_2$, and $X_3$ $$\tan 2\theta_1 = \frac{X_2}{X_1} \qquad (100)$$

$$\cos\phi_1 = \frac{X_3^2}{2X_2} - 1 \qquad (101)$$

This constitutes the basis for the 3-step PSTWR method. Three bias angles $\theta_2$ are used to solve the system of intensity equations for $X_1$, $X_2$, and $X_3$.

Eq. (97) is a system of 3 intensity equations with 3 unknowns $X_1$, $X_2$, and $X_3$ which are functions of $\phi_1$ and $\theta_1$. The system can be resolved with at least 3 intensities measured for 3 bias angles $\theta_2$. However, intensities might not be measured accurately and more measurements might minimize the measurement error. This is the basis for the N-Step PSTWR method. When N intensity measurements are made for N different bias angles, the system will have N equations with 3 unknowns. The system is overspecified and the best solution is found by minimizing the squared error e defined as $$e = TX - J \qquad (102)$$

where the matrix T is obtained by calculating $a(\theta_{2,i})$, $b(\theta_{2,i})$, and $c(\theta_{2,i})$ for the various bias angles $\theta_{2,i}$ and the matrix J is obtained by measuring the transmitted intensities at each bias angle and calculating $A(\theta_{2,i})$. It can be shown that the solution minimizing the squared error e is given by $$X = (T^T T)^{-1} T^T J \qquad (103)$$

This is the solution for the 3 unknowns $X_1$, $X_2$, and $X_3$ given the N intensity measurements J.

The N-step PSTWR technique can be used for single-point and full-field retardation measurement. The experimental configuration shown in FIG. 26 is used to implement the method for full-field evaluation. The sample is placed on the microscope stage. N images are recorded for N various compensator orientations. An image processing software and computer codes are used to solve Eq. (103) for each pixel or group of pixels. The retardation magnitude and orientation is thus determined over the entire sample.

As shown here, the PSTWR technique can be used to determine the normalized transmission intensity curve without directly measuring a minimum intensity. In that regard, the PSTWR technique is distinguishable from the Brace-Köhler compensator method. Also, being only limited by the signal-to-noise ratio of the system, the PSTWR technique can provide an approach to measuring retardation or birefringence (both the orientation and the magnitude) without directly measuring extinction, as described in the other embodiments. Additionally, it should be noted that, in the PSTWR technique, neither the compensator nor the sample would need to have its slow axis oriented at 45 degrees (or negative 45 degrees) from extinction, since the PSTWR technique provides a parametric mathematical approach.

As shown through FIGS. 1 through 27B, the various systems and methods, described above, provide an approach to measuring retardation of materials. The above-described systems and methods provide a more accurate measurement approach than Brace-Köhler compensator methods, which are currently the standard in the industry.

The automated approach may be implemented by incorporating the relevant equations, above, into a mathematical model, and using hardware, software, firmware, or a combination thereof to solve for various parameters of the model. In the preferred embodiment(s), the automated approach is implemented in software or firmware that is stored in a memory and that is executed by a suitable instruction execution system. If implemented in hardware, as in an alternative embodiment, the automated approach can be implemented with any or a combination of the following technologies, which are all well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Any process descriptions or blocks in flow charts should be understood as representing modules, segments, or portions of code which include one or more executable instructions for implementing specific logical functions or steps in the process, and alternate implementations are included within the scope of the preferred embodiment of the present invention in which functions may be executed out of order from that shown or discussed, including substantially concurrently or in reverse order, depending on the functionality involved, as would be understood by those reasonably skilled in the art of the present invention.

If the various methods, described above, are implemented in a computer program, which comprises an ordered listing of executable instructions for implementing logical functions, then that program can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can contain, store, communicate, propagate, or transport the program for use by or in connection with the instruction execution system, apparatus, or device. The computer-readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM or Flash memory) (electronic), an optical fiber (optical), and a portable compact disc read-only memory (CDROM) (optical). Note that the computer-readable medium could even be paper or another suitable medium upon which the program is printed, as the program can be electronically captured via, for instance, optical scanning of the paper or other medium, then compiled, interpreted or otherwise processed in a suitable manner if necessary, and then stored in a computer memory.

Although exemplary embodiments have been shown and described, it will be clear to those of ordinary skill in the art that a number of changes, modifications, or alterations to the invention as described may be made. For example, it should be appreciated that the incremental rotation of both the waveplate and the analyzer can be predefined, or, alternatively, defined through a trial-and-error type of approach. Similarly, while various experimental conditions have been described above with great specificity, it should be appreciated that the above-described systems and methods can be implemented on other waveplates with differing properties. It should also be appreciated that, while the two polarizers have been designated as a polarizer and an analyzer in order to avoid ambiguity, the first polarizer can be designated as the analyzer without adversely affecting the operation of disclosed embodiments. Also, while the waveplates have been designated as a sample and a compensator in order to avoid confusion, it should be appreciated that these designations can readily be reversed without adversely affecting the scope of the disclosure.

Also, while the detailed description recites specific angles, such as, for example, 45 degrees and negative 45 degrees, it should be appreciated that this is simply a shorthand for "approximately 45 degrees" and "approximately negative 45 degrees." In that regard, the numbers represented within this disclosure are not intended to be limiting, but, rather, a reasonable approximate range of numbers is contemplated for each represented number.

All such changes, modifications, and alterations should therefore be seen as within the scope of the disclosure.

What is claimed is:

1. A method for measuring retardation of materials, the method comprising the steps of:
    providing a light source for transmitting light along a light transmission axis;
    fixing a polarizer along the light transmission axis in the path of the transmitted light, the polarizer having a polarization transmission direction substantially perpendicular to the light transmission axis;
    positioning an analyzer along the light transmission axis, the analyzer having a polarization transmission direction substantially perpendicular to the light transmission axis;
    interposing a first waveplate between the polarizer and the analyzer, the first waveplate being located along the light transmission axis, the first waveplate having a slow axis, the slow axis of the first waveplate being substantially perpendicular to the light transmission axis;
    determining a first waveplate extinction angle, the first waveplate extinction angle being an angle defined by the slow axis of the first waveplate and the polarization transmission direction of the polarizer, the first waveplate extinction angle being an angle at which extinction of the transmitted light occurs for the first waveplate;
    orienting the slow axis of the first waveplate at approximately forty-five degrees from the first waveplate extinction angle;
    interposing a second waveplate between the polarizer and the analyzer, the second waveplate being located along the light transmission axis, the second waveplate having a slow axis, the slow axis of the second waveplate being substantially perpendicular to the light transmission axis;
    determining a second waveplate extinction angle, the second waveplate extinction angle being an angle defined by the slow axis of the second waveplate and the polarization transmission direction of the polarizer, the second waveplate extinction angle being an angle at which extinction of the transmitted light occurs for the second waveplate;
    orienting the slow axis of the second waveplate at approximately forty-five degrees from the second waveplate extinction angle;
    recursively rotating the first waveplate about the light transmission axis, the first waveplate being recursively rotated in predefined angular increments, the recursive rotating of the first waveplate resulting in the slow axis of the first waveplate being at different angles with reference to the polarization transmission direction of the polarizer; and
    recursively rotating the analyzer about the light transmission axis to substantially minimize light being transmitted through the analyzer, the analyzer being recursively rotated in predefined angular increments, the analyzer being recursively rotated for each of the different angles of the slow axis of the first waveplate.

2. The method of claim 1, further comprising the steps of:
    re-orienting the slow axis of the first waveplate at approximately forty-five degrees from the first waveplate extinction angle;
    recursively rotating the second waveplate about the light transmission axis, the second waveplate being recursively rotated in predefined angular increments, the recursive rotating of the second waveplate resulting in the slow axis of the second waveplate being at different angles with reference to the polarization transmission direction of the polarizer;
    recursively rotating the analyzer about the light transmission axis to substantially minimize light being transmitted through the analyzer, the analyzer being recursively rotated in predefined angular increments, the analyzer being recursively rotated for each of the different angles of the slow axis of the first waveplate; and
    determining whether the recursive rotation of the second waveplate in combination with the recursive rotation of the analyzer results in extinction.

3. The method of claim 1, further comprising the step of:
    determining whether the recursive rotation of the first waveplate in combination with the recursive rotation of the analyzer results in extinction.

4. A method comprising the steps of:
    positioning a polarizer along a light transmission axis, the polarizer having a polarization transmission direction substantially perpendicular to the light transmission axis;

positioning an analyzer along the light transmission axis, the analyzer having a polarization transmission direction substantially perpendicular to the light transmission axis;

interposing a first waveplate between the polarizer and the analyzer, the first waveplate being located along the light transmission axis, the first waveplate having a slow axis, the slow axis of the first waveplate being substantially perpendicular to the light transmission axis;

interposing a second waveplate between the polarizer and the analyzer, the second waveplate being located along the light transmission axis, the second waveplate having a slow axis, the slow axis of the second waveplate being substantially perpendicular to the light transmission axis;

rotating the first waveplate about the light transmission axis, the rotating of the first waveplate resulting in the slow axis of the first waveplate being at an angle with reference to the polarization transmission direction of the polarizer; and rotating the analyzer about the light transmission axis to substantially minimize light being transmitted through the analyzer.

5. The method of claim 4, further comprising the step of detecting light transmitted along the light transmission axis.

6. The method of claim 4, the step of interposing the first waveplate comprising the step of orienting the slow axis of the first waveplate at approximately forty-five degrees from extinction.

7. The method of claim 4, the step of interposing the second waveplate comprising the step of orienting the slow axis of the second waveplate at approximately forty-five degrees from extinction.

8. The method of claim 4, the step of rotating the first waveplate comprising the step of recursively rotating the first waveplate about the light transmission axis, the recursive rotating of the first waveplate resulting in the slow axis of the first waveplate being at different angles with reference to the polarization transmission direction of the polarizer.

9. The method of claim 8, the step of recursively rotating the first waveplate comprising the step of rotating the first waveplate at predefined angular increments, the first waveplate being rotated about the light transmission axis.

10. A system comprising:

a polarizer located along a light transmission axis, the polarizer having a polarization transmission direction substantially perpendicular to the light transmission axis;

an analyzer located along the light transmission axis, the analyzer having a polarization transmission direction substantially perpendicular to the light transmission axis, the analyzer being configured to rotate about the light transmission axis;

a first waveplate interposed between the polarizer and the analyzer, the first waveplate being located along the light transmission axis, the first waveplate having a slow axis, the slow axis of the first waveplate being substantially perpendicular to the light transmission axis, the first waveplate being configured to rotate about the light transmission axis, the combination of the rotating of the first waveplate and the rotating of the analyzer resulting in extinction of light being transmitted through the analyzer; and a second waveplate interposed between the polarizer and the analyzer, the second waveplate being located along the light transmission axis, the second waveplate having a slow axis, the slow axis of the second waveplate being substantially perpendicular to the light transmission axis.

11. The system of claim 10, further comprising:

a light source configured to transmit light along the light transmission axis.

12. The system of claim 10, further comprising:

a detector configured to detect light transmitted along the light transmission axis.

13. The system of claim 10, further comprising:

means for detecting light transmitted along the light transmission axis.

* * * * *